US008017779B2

(12) United States Patent
Merrill et al.

(10) Patent No.: US 8,017,779 B2
(45) Date of Patent: *Sep. 13, 2011

(54) NITROGEN CONTAINING HETEROCYCLYL SUBSTITUTED IMIDAZOQUINOLINES AND IMIDAZONAPHTHYRIDINES

(75) Inventors: Bryon A. Merrill, River Falls, WI (US); Chad A. Haraldson, Apple Valley, MN (US); Tushar A. Kshirsagar, Woodbury, MN (US); Shri Niwas, Maple Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1231 days.

This patent is subject to a terminal disclaimer.

(21) Appl. No.: 11/570,611

(22) PCT Filed: Jun. 15, 2005

(86) PCT No.: PCT/US2005/020912
§ 371 (c)(1),
(2), (4) Date: Dec. 14, 2006

(87) PCT Pub. No.: WO2005/123080
PCT Pub. Date: Dec. 29, 2005

(65) Prior Publication Data
US 2007/0213356 A1    Sep. 13, 2007

Related U.S. Application Data

(60) Provisional application No. 60/579,829, filed on Jun. 15, 2004.

(51) Int. Cl.
C07D 471/02 (2006.01)
A61K 31/437 (2006.01)
(52) U.S. Cl. .................... 546/82; 546/83; 514/293
(58) Field of Classification Search .......... 546/82, 546/83; 514/293
See application file for complete search history.

(56) References Cited

U.S. PATENT DOCUMENTS

| | | | |
|---|---|---|---|
| 3,314,941 A | 4/1967 | Littell et al. |
| 3,450,693 A | 6/1969 | Suzuki et al. |
| 3,670,086 A | 6/1972 | Pryor et al. |
| 3,692,907 A | 9/1972 | Fleming et al. |
| 3,891,660 A | 6/1975 | Denzel et al. |
| 3,899,508 A | 8/1975 | Wikel |
| 3,917,624 A | 11/1975 | Abu El-Haj et al. |
| 4,006,237 A | 2/1977 | Buckle et al. |
| 4,053,588 A | 10/1977 | Konig et al. |
| 4,381,344 A | 4/1983 | Rideout et al. |
| 4,552,874 A | 11/1985 | Mardin et al. |
| 4,563,525 A | 1/1986 | Campbell, Jr. |
| 4,593,821 A | 6/1986 | Brule |
| 4,668,686 A | 5/1987 | Meanwell et al. |
| 4,689,338 A | 8/1987 | Gerster |
| 4,690,930 A | 9/1987 | Takada et al. |
| 4,698,346 A | 10/1987 | Musser et al. |
| 4,698,348 A | 10/1987 | Gerster |
| 4,753,951 A | 6/1988 | Takada et al. |
| 4,758,574 A | 7/1988 | Robertson et al. |
| 4,774,339 A | 9/1988 | Haugland et al. |
| 4,775,674 A | 10/1988 | Meanwell et al. |
| 4,800,206 A | 1/1989 | Alig et al. |
| 4,826,830 A | 5/1989 | Han et al. |
| 4,837,378 A | 6/1989 | Borgman |
| 4,880,779 A | 11/1989 | Gallaher |
| 4,904,669 A | 2/1990 | Knoll et al. |
| 4,929,624 A | 5/1990 | Gerster et al. |
| 4,988,714 A | 1/1991 | Alig et al. |
| 4,988,815 A | 1/1991 | Andre et al. |
| 5,037,986 A | 8/1991 | Gerster |
| 5,175,296 A | 12/1992 | Gerster |
| 5,187,288 A | 2/1993 | Kang et al. |
| 5,225,183 A | 7/1993 | Purewal et al. |
| 5,238,944 A | 8/1993 | Wick et al. |
| 5,248,782 A | 9/1993 | Haugland et al. |
| 5,266,575 A | 11/1993 | Gerster |
| 5,268,376 A | 12/1993 | Gester |
| 5,274,113 A | 12/1993 | Kang et al. |
| 5,346,905 A | 9/1994 | Gerster |
| 5,352,680 A | 10/1994 | Portoghese et al. |
| 5,352,784 A | 10/1994 | Nikolaides et al. |
| 5,367,076 A | 11/1994 | Gerster |
| 5,376,501 A | 12/1994 | Marien et al. |
| 5,378,848 A | 1/1995 | Takada et al. |
| 5,389,640 A | 2/1995 | Gerster et al. |

(Continued)

FOREIGN PATENT DOCUMENTS

AU         2004220534 A1    9/2004

(Continued)

OTHER PUBLICATIONS

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983. Brennan at al., "Automated Bioassay of Interferons in Micro-test Plates.", *Biotechniques*, Jun./Jul. 78, 1983.
Testerman et al., "Cytokine Induction by the Immunomodulators Imiquimod and S-27609.", *Journal of Leukocyte Biology*, vol. 58, pp. 365-372, Sep. 1995.
Bachman et al., "Synthesis of Substituted Quinolylamines. Derivatives of 4-Amino-7- Chloroquinoline.", *J. Org. Chem*, 15, pp. 1278-1284 (1950).
Jain at al., "Chemical and Pharmacological Investigations of Some ω-Substituted Alkylamino-3-aminopyridines.", *J. Med. Chem.*, 11, pp. 87-92 (1968).
Baranov at al., "Pyrazoles, Imidazoles, and Other 5-Membered Rings.", *Chem. Abs.* 85, 94362, (1976).

(Continued)

*Primary Examiner* — Rita Desai
(74) *Attorney, Agent, or Firm* — Kathleen B. Gross; Dean A. Ersfeld

(57) ABSTRACT

Imidazoquinoline and imidazonaphthyridine compounds having a nitrogen-containing heterocyclyl substituent at the 5-, 6-, 7-, or 8-position, pharmaceutical compositions containing the compounds, intermediates, and methods of making and methods of use of these compounds as immunomodulators, for modulating cytokine biosynthesis in animals and in the treatment of diseases including viral and neoplastic diseases are disclosed.

14 Claims, No Drawings

U.S. PATENT DOCUMENTS

| | | |
|---|---|---|
| 5,395,937 A | 3/1995 | Nikolaides et al. |
| 5,444,065 A | 8/1995 | Nikolaides et al. |
| 5,446,153 A | 8/1995 | Lindstrom et al. |
| 5,446,160 A | 8/1995 | Stucky et al. |
| 5,482,936 A | 1/1996 | Lindstrom |
| 5,494,916 A | 2/1996 | Lindstrom et al. |
| 5,500,228 A | 3/1996 | Lawter et al. |
| 5,525,612 A | 6/1996 | Gerster |
| 5,530,114 A | 6/1996 | Bennett et al. |
| 5,569,450 A | 10/1996 | Duan et al. |
| 5,571,819 A | 11/1996 | Sabb et al. |
| 5,578,727 A | 11/1996 | Andre et al. |
| 5,585,612 A | 12/1996 | Harp, Jr. |
| 5,602,256 A | 2/1997 | Andre et al. |
| 5,605,899 A | 2/1997 | Gerster et al. |
| 5,612,377 A | 3/1997 | Crooks et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,731,193 A | 3/1998 | Mori et al. |
| 5,736,553 A | 4/1998 | Wick et al. |
| 5,741,908 A | 4/1998 | Gerster et al. |
| 5,741,909 A | 4/1998 | Gerster et al. |
| 5,750,134 A | 5/1998 | Scholz et al. |
| 5,756,747 A | 5/1998 | Gerster et al. |
| 5,776,432 A | 7/1998 | Schultz et al. |
| 5,780,045 A | 7/1998 | McQuinn et al. |
| 5,837,809 A | 11/1998 | Grandy et al. |
| 5,840,744 A | 11/1998 | Borgman |
| 5,854,257 A | 12/1998 | Armitage et al. |
| 5,861,268 A | 1/1999 | Tang et al. |
| 5,886,006 A | 3/1999 | Nikolaides et al. |
| 5,939,047 A | 8/1999 | Jernberg |
| 5,939,090 A | 8/1999 | Beaurline et al. |
| 5,962,479 A | 10/1999 | Chen |
| 5,962,636 A | 10/1999 | Bachmaier et al. |
| 5,977,366 A | 11/1999 | Gerster et al. |
| 6,028,076 A | 2/2000 | Hirota et al. |
| 6,039,969 A | 3/2000 | Tomai et al. |
| 6,057,371 A | 5/2000 | Glennon |
| 6,069,140 A | 5/2000 | Sessler et al. |
| 6,069,149 A | 5/2000 | Nanba et al. |
| 6,071,949 A | 6/2000 | Mulshine et al. |
| 6,077,349 A | 6/2000 | Kikuchi |
| 6,083,505 A | 7/2000 | Miller et al. |
| 6,110,929 A | 8/2000 | Gerster et al. |
| 6,113,918 A | 9/2000 | Johnson et al. |
| 6,121,323 A | 9/2000 | Merrill |
| 6,123,957 A | 9/2000 | Jernberg |
| 6,126,938 A | 10/2000 | Guy et al. |
| 6,194,388 B1 | 2/2001 | Krieg et al. |
| 6,194,425 B1 | 2/2001 | Gerster et al. |
| 6,200,592 B1 | 3/2001 | Tomai et al. |
| 6,207,646 B1 | 3/2001 | Krieg et al. |
| 6,239,116 B1 | 5/2001 | Krieg et al. |
| 6,245,776 B1 | 6/2001 | Skwierczynski et al. |
| 6,294,271 B1 | 9/2001 | Sumita et al. |
| 6,303,347 B1 | 10/2001 | Johnson et al. |
| 6,309,623 B1 | 10/2001 | Weers et al. |
| 6,315,985 B1 | 11/2001 | Wu et al. |
| 6,323,200 B1 | 11/2001 | Gerster et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,348,462 B1 | 2/2002 | Gerster et al. |
| 6,365,166 B2 | 4/2002 | Beaurline et al. |
| 6,376,501 B1 | 4/2002 | Isobe et al. |
| 6,376,669 B1 | 4/2002 | Rice et al. |
| 6,387,383 B1 | 5/2002 | Dow et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,440,992 B1 | 8/2002 | Gerster et al. |
| 6,451,485 B1 | 9/2002 | James et al. |
| 6,451,810 B1 | 9/2002 | Coleman et al. |
| 6,465,654 B2 | 10/2002 | Gerster et al. |
| 6,476,000 B1 | 11/2002 | Agrawal |
| 6,486,168 B1 | 11/2002 | Skwierczynski et al. |
| 6,486,186 B2 | 11/2002 | Fowler et al. |
| 6,511,485 B2 | 1/2003 | Hirt et al. |
| 6,514,985 B1 | 2/2003 | Gerster et al. |
| 6,518,239 B1 | 2/2003 | Kuo et al. |
| 6,518,265 B1 | 2/2003 | Kato et al. |
| 6,518,280 B2 | 2/2003 | Gerster et al. |
| 6,525,028 B1 | 2/2003 | Johnson et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,582,957 B1 | 6/2003 | Turner, Jr. et al. |
| 6,610,319 B2 | 8/2003 | Tomai et al. |
| 6,627,638 B2 | 9/2003 | Gerster et al. |
| 6,627,639 B2 | 9/2003 | Stack et al. |
| 6,627,640 B2 | 9/2003 | Gerster et al. |
| 6,630,588 B2 | 10/2003 | Rice et al. |
| 6,638,944 B2 | 10/2003 | Mickelson |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,334 B2 | 1/2004 | Gerster et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,780,873 B2 | 8/2004 | Crooks et al. |
| 6,784,188 B2 | 8/2004 | Crooks et al. |
| 6,790,961 B2 | 9/2004 | Gerster et al. |
| 6,797,718 B2 | 9/2004 | Dellaria et al. |
| 6,800,624 B2 | 10/2004 | Crooks et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,855,217 B2 | 2/2005 | Suzuki |
| 6,855,350 B2 | 2/2005 | Lu |
| 6,878,719 B2 | 4/2005 | Lindstrom et al. |
| 6,888,000 B2 | 5/2005 | Crooks et al. |
| 6,894,060 B2 | 5/2005 | Slade |
| 6,894,165 B2 | 5/2005 | Gerster et al. |
| 6,897,221 B2 | 5/2005 | Crooks et al. |
| 6,900,016 B1 | 5/2005 | Venter et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,240 B2 | 9/2005 | Bauer et al. |
| 6,943,255 B2 | 9/2005 | Lindstrom et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,253 B2 | 7/2006 | Brunner et al. |
| 7,078,523 B2 | 7/2006 | Crooks et al. |

| Patent/Publication | Date | Inventors |
|---|---|---|
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,544,697 B2 | 6/2009 | Hays et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 2001/0046968 A1 | 11/2001 | Zagon et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2002/0110840 A1 | 8/2002 | Tomai et al. |
| 2002/0137101 A1 | 9/2002 | Meyers |
| 2002/0173655 A1 | 11/2002 | Dellaria et al. |
| 2002/0193729 A1 | 12/2002 | Cormier et al. |
| 2003/0022302 A1 | 1/2003 | Lewis et al. |
| 2003/0044429 A1 | 3/2003 | Aderem et al. |
| 2003/0082108 A1 | 5/2003 | Mulshine et al. |
| 2003/0088102 A1 | 5/2003 | Matsubara et al. |
| 2003/0096835 A1 | 5/2003 | Crooks et al. |
| 2003/0096998 A1 | 5/2003 | Gerster et al. |
| 2003/0130299 A1 | 7/2003 | Crooks et al. |
| 2003/0133733 A1 | 7/2003 | Korhonen |
| 2003/0133913 A1 | 7/2003 | Tomai et al. |
| 2003/0139364 A1 | 7/2003 | Krieg et al. |
| 2003/0144283 A1 | 7/2003 | Coleman et al. |
| 2003/0144286 A1 | 7/2003 | Frenkel et al. |
| 2003/0158192 A1 | 8/2003 | Crooks et al. |
| 2003/0161797 A1 | 8/2003 | Miller et al. |
| 2003/0172391 A1 | 9/2003 | Turner et al. |
| 2003/0185835 A1 | 10/2003 | Braun |
| 2003/0187016 A1 | 10/2003 | Crooks et al. |
| 2003/0199461 A1 | 10/2003 | Averett et al. |
| 2003/0199538 A1 | 10/2003 | Skwierczynski et al. |
| 2003/0212092 A1 | 11/2003 | Heppner et al. |
| 2003/0216481 A1 | 11/2003 | Jia |
| 2003/0232074 A1 | 12/2003 | Lipford et al. |
| 2003/0232763 A1 | 12/2003 | Jia |
| 2003/0232852 A1 | 12/2003 | Lindstrom et al. |
| 2004/0010007 A1 | 1/2004 | Dellaria et al. |
| 2004/0014779 A1 | 1/2004 | Gorden et al. |
| 2004/0023870 A1 | 2/2004 | Dedera et al. |
| 2004/0067975 A1 | 4/2004 | Crooks et al. |
| 2004/0072858 A1 | 4/2004 | Charles et al. |
| 2004/0076633 A1 | 4/2004 | Thomsen et al. |
| 2004/0091491 A1 | 5/2004 | Kedl et al. |
| 2004/0092545 A1 | 5/2004 | Crooks et al. |
| 2004/0097542 A1 | 5/2004 | Crooks et al. |
| 2004/0106638 A1 | 6/2004 | Lindstrom |
| 2004/0132079 A1 | 7/2004 | Gupta et al. |
| 2004/0132748 A1 | 7/2004 | Isobe et al. |
| 2004/0132766 A1 | 7/2004 | Griesgraber |
| 2004/0141950 A1 | 7/2004 | Noelle et al. |
| 2004/0147543 A1 | 7/2004 | Hays et al. |
| 2004/0157874 A1 | 8/2004 | Crooks et al. |
| 2004/0162309 A1 | 8/2004 | Gorden et al. |
| 2004/0167157 A1 | 8/2004 | Masui et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Lee et al. |
| 2004/0181130 A1 | 9/2004 | Fox et al. |
| 2004/0181211 A1 | 9/2004 | Elliott et al. |
| 2004/0191833 A1 | 9/2004 | Fink et al. |
| 2004/0192585 A1 | 9/2004 | Fox et al. |
| 2004/0197865 A1 | 10/2004 | Gupta et al. |
| 2004/0202720 A1 | 10/2004 | Wightman et al. |
| 2004/0204436 A1 | 10/2004 | Gerster et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0009858 A1 | 1/2005 | Martinez-Colon et al. |
| 2005/0032829 A1 | 2/2005 | Lindstrom et al. |
| 2005/0048072 A1 | 3/2005 | Kedl et al. |
| 2005/0054590 A1 | 3/2005 | Averett |
| 2005/0054640 A1 | 3/2005 | Griesgraber et al. |
| 2005/0054665 A1 | 3/2005 | Miller et al. |
| 2005/0059072 A1 | 3/2005 | Birmachu et al. |
| 2005/0070460 A1 | 3/2005 | Hammerbeck et al. |
| 2005/0085500 A1 | 4/2005 | Gutman et al. |
| 2005/0096259 A1 | 5/2005 | Tomai et al. |
| 2005/0119273 A1 | 6/2005 | Lipford et al. |
| 2005/0136065 A1 | 6/2005 | Valiante |
| 2005/0148620 A1 | 7/2005 | Crooks et al. |
| 2005/0158325 A1 | 7/2005 | Hammerbeck et al. |
| 2005/0165236 A1 | 7/2005 | Colombo et al. |
| 2005/0171072 A1 | 8/2005 | Tomai et al. |
| 2005/0226878 A1 | 10/2005 | Tomai et al. |
| 2005/0234088 A1 | 10/2005 | Griesgraber |
| 2005/0239733 A1 | 10/2005 | Jurk et al. |
| 2005/0239735 A1 | 10/2005 | Miller et al. |
| 2005/0245562 A1 | 11/2005 | Garcia-Echeverria et al. |
| 2005/0267145 A1 | 12/2005 | Merrill et al. |
| 2005/0281813 A1 | 12/2005 | Dedera et al. |
| 2006/0009482 A1 | 1/2006 | Tomai et al. |
| 2006/0100229 A1 | 5/2006 | Hays et al. |
| 2006/0106052 A1 | 5/2006 | Crooks et al. |
| 2006/0188913 A1 | 8/2006 | Krieg et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0155767 A1 | 7/2007 | Radmer et al. |
| 2007/0166384 A1 | 7/2007 | Zarraga |
| 2007/0167476 A1 | 7/2007 | Kshirsagar et al. |
| 2007/0208052 A1 | 9/2007 | Prince et al. |
| 2007/0219196 A1 | 9/2007 | Krepski et al. |
| 2007/0219228 A1 | 9/2007 | Niwas et al. |
| 2007/0259881 A1 | 11/2007 | Dellaria et al. |
| 2007/0259907 A1 | 11/2007 | Prince |
| 2007/0287725 A1 | 12/2007 | Miser et al. |
| 2007/0292456 A1 | 12/2007 | Hammerbeck et al. |
| 2008/0015184 A1 | 1/2008 | Kshirsagar et al. |
| 2008/0070907 A1 | 3/2008 | Griesgraber et al. |
| 2008/0085895 A1 | 4/2008 | Griesgraber et al. |
| 2008/0114019 A1 | 5/2008 | Kshirsagar et al. |
| 2008/0119508 A1 | 5/2008 | Slade et al. |
| 2008/0207674 A1 | 8/2008 | Stoesz et al. |
| 2008/0269192 A1 | 10/2008 | Griesgraber et al. |
| 2008/0306252 A1 | 12/2008 | Crooks et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0018122 A1 | 1/2009 | Lindstrom et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0042925 A1 | 2/2009 | Kshirsagar et al. |
| 2009/0062272 A1 | 3/2009 | Bonk et al. |
| 2009/0062328 A1 | 3/2009 | Kshirsagar et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0240055 A1 | 9/2009 | Krepski et al. |

| | | | |
|---|---|---|---|
| 2009/0253695 A1 | 10/2009 | Kshirsagar et al. | |
| 2009/0270443 A1 | 10/2009 | Stoermer et al. | |
| 2009/0318435 A1 | 12/2009 | Hays et al. | |
| 2010/0113565 A1 | 5/2010 | Gorden et al. | |
| 2010/0240693 A1 | 9/2010 | Lundquist, Jr. et al. | |

FOREIGN PATENT DOCUMENTS

| | | |
|---|---|---|
| AU | 2004229478 A1 | 10/2004 |
| AU | 2004264336 A1 | 2/2005 |
| AU | 2004268625 A1 | 3/2005 |
| AU | 2002239547 B2 | 11/2006 |
| CA | 2044087 A1 | 12/1991 |
| CA | 2158996 A1 | 10/1994 |
| CN | 1354663 A | 6/2002 |
| EP | 0 145 340 A2 | 6/1985 |
| EP | 0 223 420 A1 | 5/1987 |
| EP | 0 310 950 A1 | 4/1989 |
| EP | 0 385 630 A2 | 9/1990 |
| EP | 0 389 302 A1 | 9/1990 |
| EP | 0 394 026 | 10/1990 |
| EP | 0 425 306 A2 | 5/1991 |
| EP | 0 510 260 A2 | 10/1992 |
| EP | 0 556 008 A1 | 8/1993 |
| EP | 0 645 389 A1 | 3/1995 |
| EP | 0 778 277 A1 | 6/1997 |
| EP | 0 894 797 A1 | 2/1999 |
| EP | 1 082 960 A2 | 3/2001 |
| EP | 1 097 709 A2 | 5/2001 |
| EP | 1 104 764 | 6/2001 |
| EP | 1 145 340 A2 | 10/2001 |
| EP | 1 256 582 A1 | 11/2002 |
| EP | 1 341 791 A2 | 9/2003 |
| EP | 1 495 758 A2 | 1/2005 |
| HU | 34479 A2 | 3/1985 |
| HU | 210051 A2 | 6/1991 |
| HU | 218950 A2 | 9/1995 |
| IL | 73534 A | 12/1990 |
| JP | 53050197 A | 5/1978 |
| JP | 63010787 A | 1/1988 |
| JP | 4066571 A | 3/1992 |
| JP | 4327587 A | 11/1992 |
| JP | 5286973 A | 11/1993 |
| JP | 9-208584 | 8/1997 |
| JP | 11-080156 A | 3/1999 |
| JP | 11-222432 | 8/1999 |
| JP | 2000-247884 | 9/2000 |
| NZ | 545412 A | 12/2008 |
| RU | 2076105 C1 | 3/1997 |
| RU | 2127273 C1 | 3/1999 |
| RU | 2221798 C2 | 1/2004 |
| WO | WO-91/06682 A1 | 5/1991 |
| WO | WO-92/06093 A1 | 4/1992 |
| WO | WO-92/15581 A1 | 9/1992 |
| WO | WO-92/15582 A1 | 9/1992 |
| WO | WO-93/05042 A1 | 3/1993 |
| WO | WO-93/09119 A1 | 5/1993 |
| WO | WO-93/20847 A1 | 10/1993 |
| WO | WO-94/10171 A1 | 5/1994 |
| WO | WO-95/02597 A1 | 1/1995 |
| WO | WO-95/02598 A1 | 1/1995 |
| WO | WO-96/11199 A1 | 4/1996 |
| WO | WO-96/21663 A1 | 7/1996 |
| WO | WO-97/48703 A1 | 12/1997 |
| WO | WO-97/48704 A1 | 12/1997 |
| WO | WO-98/17279 A1 | 4/1998 |
| WO | WO-98/30562 A1 | 7/1998 |
| WO | WO-98/48805 A1 | 11/1998 |
| WO | WO-98/50547 A2 | 11/1998 |
| WO | WO-98/54226 A1 | 12/1998 |
| WO | WO-99/18105 A1 | 4/1999 |
| WO | WO-99/29693 A1 | 6/1999 |
| WO | WO-00/06577 A1 | 2/2000 |
| WO | WO-00/09506 A1 | 2/2000 |
| WO | WO-00/19987 A1 | 4/2000 |
| WO | WO-00/40228 A2 | 7/2000 |
| WO | WO-00/47719 A2 | 8/2000 |
| WO | WO-00/75304 A1 | 12/2000 |
| WO | WO-00/76505 A1 | 12/2000 |
| WO | WO-00/76518 A1 | 12/2000 |
| WO | WO-00/76519 A1 | 12/2000 |
| WO | WO-01/34709 A1 | 5/2001 |
| WO | WO-01/51486 A2 | 7/2001 |
| WO | WO-01/55439 A1 | 8/2001 |
| WO | WO-01/58900 A1 | 8/2001 |
| WO | WO-01/74343 A2 | 10/2001 |
| WO | WO-01/74821 A1 | 10/2001 |
| WO | WO-02/07725 A1 | 1/2002 |
| WO | WO-02/22809 A2 | 3/2002 |
| WO | WO-02/24225 A1 | 3/2002 |
| WO | WO 02/36592 | 5/2002 |
| WO | WO-02/46188 A2 | 6/2002 |
| WO | WO-02/46189 A2 | 6/2002 |
| WO | WO-02/46190 A2 | 6/2002 |
| WO | WO-02/46191 A2 | 6/2002 |
| WO | WO-02/46192 A2 | 6/2002 |
| WO | WO-02/46193 A2 | 6/2002 |
| WO | WO-02/46194 A2 | 6/2002 |
| WO | WO-02/46749 A2 | 6/2002 |
| WO | WO-02/085905 A1 | 10/2002 |
| WO | WO-02/102377 A1 | 12/2002 |
| WO | WO-03/008421 A1 | 1/2003 |
| WO | WO-03/009852 A1 | 2/2003 |
| WO | WO-03/020889 A2 | 3/2003 |
| WO | WO-03/043572 A2 | 5/2003 |
| WO | WO-03/045391 A1 | 6/2003 |
| WO | WO-03/045494 A2 | 6/2003 |
| WO | WO-03/045929 A1 | 6/2003 |
| WO | WO-03/050117 A1 | 6/2003 |
| WO | WO-03/050118 A1 | 6/2003 |
| WO | WO-03/050119 A2 | 6/2003 |
| WO | WO-03/050121 A1 | 6/2003 |
| WO | WO-03/077944 A1 | 9/2003 |
| WO | WO-03/080114 A1 | 10/2003 |
| WO | WO-03/086280 A2 | 10/2003 |
| WO | WO-03/086350 A1 | 10/2003 |
| WO | WO-03/089602 A2 | 10/2003 |
| WO | WO-03/097641 A2 | 11/2003 |
| WO | WO-03/101949 A1 | 12/2003 |
| WO | WO-03/103584 A2 | 12/2003 |
| WO | WO-2004/009593 A1 | 1/2004 |
| WO | WO-2004/028539 A2 | 4/2004 |
| WO | WO-2004/041285 A1 | 5/2004 |
| WO | WO-2004/043913 A2 | 5/2004 |
| WO | WO-2004/053057 A2 | 6/2004 |
| WO | WO-2004/053452 A2 | 6/2004 |
| WO | WO-2004/058759 A1 | 7/2004 |
| WO | WO-2004/071459 A2 | 8/2004 |
| WO | WO-2004/075865 A2 | 9/2004 |
| WO | WO-2004/080398 A2 | 9/2004 |
| WO | WO-2004/091500 A2 | 10/2004 |
| WO | WO-2004/096144 A2 | 11/2004 |
| WO | WO-2004/110991 A2 | 12/2004 |
| WO | WO-2004/110992 A2 | 12/2004 |
| WO | WO-2005/003064 A2 | 1/2005 |
| WO | WO-2005/003065 A2 | 1/2005 |
| WO | WO-2005/016273 A2 | 2/2005 |
| WO | WO-2005/016275 A2 | 2/2005 |
| WO | WO 2005/018551 | 3/2005 |
| WO | WO 2005/018555 | 3/2005 |
| WO | WO 2005/018556 | 3/2005 |
| WO | WO 2005/020999 | 3/2005 |
| WO | WO-2005/023190 A2 | 3/2005 |
| WO | WO-2005/025614 A3 | 3/2005 |
| WO | WO-2005/029037 A2 | 3/2005 |
| WO | WO 2005/032484 | 4/2005 |
| WO | WO-2005/041891 A2 | 5/2005 |
| WO | WO 2005/048933 | 6/2005 |
| WO | WO 2005/048945 | 6/2005 |
| WO | WO-2005/049076 A1 | 6/2005 |
| WO | WO 2005/051317 | 6/2005 |
| WO | WO 2005/051324 | 6/2005 |
| WO | WO 2005/054237 | 6/2005 |
| WO | WO 2005/054238 | 6/2005 |
| WO | WO-2005/065678 A1 | 7/2005 |
| WO | WO 2005/066169 | 7/2005 |
| WO | WO 2005/066170 | 7/2005 |
| WO | WO 2005/066172 | 7/2005 |
| WO | WO-2005/067500 A2 | 7/2005 |

| | | |
|---|---|---|
| WO | WO 2005/076783 | 8/2005 |
| WO | WO 2005/079195 | 9/2005 |
| WO | WO 2005/094531 | 10/2005 |
| WO | WO-2005/110013 A2 | 11/2005 |
| WO | WO 2005/123079 | 12/2005 |
| WO | WO 2005/123080 | 12/2005 |
| WO | WO 2006/009826 | 1/2006 |
| WO | WO 2006/009832 | 1/2006 |
| WO | WO 2006/026760 | 3/2006 |
| WO | WO 2006/028451 | 3/2006 |
| WO | WO 2006/028545 | 3/2006 |
| WO | WO 2006/028962 | 3/2006 |
| WO | WO 2006/029115 | 3/2006 |
| WO | WO 2006/031878 | 3/2006 |
| WO | WO 2006/038923 | 4/2006 |
| WO | WO-2006/038923 A2 | 4/2006 |
| WO | WO-2006/063072 A2 | 6/2006 |
| WO | WO-2006/063152 A2 | 6/2006 |
| WO | WO 2006/065280 | 6/2006 |
| WO | WO-2006/073940 A2 | 7/2006 |
| WO | WO 2006/074003 | 7/2006 |
| WO | WO-2006/074045 A2 | 7/2006 |
| WO | WO 2006/004737 | 8/2006 |
| WO | WO 2006/083400 | 8/2006 |
| WO | WO 2006/083440 | 8/2006 |
| WO | WO-2006/084251 A2 | 8/2006 |
| WO | WO 2006/086449 | 8/2006 |
| WO | WO 2006/086633 | 8/2006 |
| WO | WO-2006/086634 A2 | 8/2006 |
| WO | WO 2006/091394 | 8/2006 |
| WO | WO 2006/091567 | 8/2006 |
| WO | WO 2006/091568 | 8/2006 |
| WO | WO 2006/091647 | 8/2006 |
| WO | WO-2006/093514 A2 | 9/2006 |
| WO | WO 2006/098852 | 9/2006 |
| WO | WO-2006/107753 A2 | 10/2006 |
| WO | WO 2006/107771 | 10/2006 |
| WO | WO 2006/107851 | 10/2006 |
| WO | WO 2006/107853 | 10/2006 |
| WO | WO 2006/121528 | 11/2006 |
| WO | WO-2006/122806 A2 | 11/2006 |
| WO | WO-2007/028129 A1 | 3/2007 |
| WO | WO-2007/030775 A2 | 3/2007 |
| WO | WO-2007/030777 A2 | 3/2007 |
| WO | WO-2007/035935 A1 | 3/2007 |
| WO | WO-2007/056112 A2 | 5/2007 |
| WO | WO-2007/062043 A1 | 5/2007 |
| WO | WO-2007/075468 A1 | 7/2007 |
| WO | WO-2007/079086 A1 | 7/2007 |
| WO | WO-2007/079146 A1 | 7/2007 |
| WO | WO-2007/079169 A2 | 7/2007 |
| WO | WO-2007/079171 A2 | 7/2007 |
| WO | WO-2007/079202 A2 | 7/2007 |
| WO | WO-2007/079203 A2 | 7/2007 |
| WO | WO-2007/092641 A2 | 8/2007 |
| WO | WO-2007/106852 A2 | 9/2007 |
| WO | WO-2007/106854 A2 | 9/2007 |
| WO | WO-2007/120121 A2 | 10/2007 |
| WO | WO-2007/143526 A2 | 12/2007 |
| WO | WO-2008/008432 A2 | 1/2008 |
| WO | WO-2008/030511 A2 | 3/2008 |
| WO | WO-2008/036312 A1 | 3/2008 |
| WO | WO-2008/045543 A1 | 4/2008 |

OTHER PUBLICATIONS

Berényi et al., "Ring Transformation of Condensed Dihydro-astriazines.", *J. Heterocyclic Chem.*, 18, pp. 1537-1540 (1981).
Chollet et al., "Development of a Topically Active Imiquimod Formulation.", *Pharmaceutical Development and Technology*, 4(1), pp. 35-43 (1999).
Izumi et al., "1H-Imidazo[4,5-c]quinoline Derivatives as Novel Potent TNF-α Suppressors: Synthesis and Structure-Activity Relationship of 1-, 2- and 4-Substituted 1H-imidazo[4,5-c]pyridines.", *Bioorganic & Medicinal Chemistry*, 11, pp. 2541-2550 (2003).
International Search Report and Written Opinion for PCT/US2005/020912 mailed Mar. 29, 2006.
International Preliminary Report on Patentability for PCT/US2005/020912 mailed Dec. 20, 2006.
[No Author Listed] "Comparative Tests." Filed Apr. 8, 2005 during prosecution for EP 00938205.2, EP 00950215.4 and EP 00938211.0 in the name of 3M Innovative Properties Co.
[No Author Listed] Chemical Abstracts. 1964;61(1):6060g.
[No Author Listed] Encyclopedia of Pharmaceutical Technology. 2nd Ed. Marcel Dekker, Inc. 2002:856-60.
Agrawal et al., Synthetic agonists of Toll-like receptors 7, 8 and 9. Biochem Soc Trans. Dec. 2007;35(Pt 6):1461-7.
Ahmed et al., A new rapid and simple non-radioactive assay to monitor and determine the proliferation of lymphocytes: an alternative to [3H]thymidine incorporation assay. J Immunol Methods. Apr. 15, 1994;170(2):211-24.
Akira et al., Recognition of pathogen-associated molecular patterns by TLR family. Immunol Lett. 2003;85:85-95.
Akira et al., Toll-like receptors: critical proteins linking innate and acquired immunity. Nature Immunol. 2001;2(8):675-80.
Alexopoulou et al., Recognition of double-stranded RNA and activation of NF-kappaB by Toll-like receptor 3. Nature. Oct. 18, 2001;413(6857):732-8.
Assuma et al., IL-1 and TNF Antagonists Inhibit the Inflammatory Response and Bone Loss in Experimental Periodontitis. J Immunol. 2000;160:403-09.
Au et al., Virus-mediated induction of interferon a gene requires cooperation between multiple binding factors in the interferon alpha promoter region. J Biol Chem. Nov. 15, 1993;268(32):24032-40.
Auerbach et al., Erythema nodosum following a jellyfish sting. J Emerg Med. Nov.-Dec. 1987;5(6):487-91.
Auwers, [Uber die Isomerie-Verhaltnisse in der Pyrazol-Reihe. Berichte. VI.] 1926;601-607. German.
Baffis et al., Use of interferon for prevention of hepatocellular carcinoma in cirrhotic patients with hepatitis B or hepatitis C virus infection. Ann Intern Med. Nov. 2, 1999;131(9):696-701.
Baker et al., Oral infection with Porphyromonas gingivalis and induced alveolar bone loss in immunocompetent and severe combined immunodeficient mice. Arch Oral Biol. Dec. 1994;39(12):1035-40.
Baldwin et al., Amino Acid Synthesis via Ring Opening of N-Sulphonyl Aziridine-2-Carboxylate Esters with Organometallic Reagents. Tetrahedron. 1993;49:6309-30.
Bártová et al., Th1 and Th2 cytokine profile in patients with early onset periodontitis and their healthy siblings. Mediators Inflamm. 2000;9(2):115-20.
Beck et al., Dental Infections and Atherosclerosis. Am Heart J. 1999;13:528-33.
Beckett et al., Configurational Studies in Synthetic Analgesics: the Synthesis of (−)-Methadone from D-(−)- Alanine. J Chem Soc. 1957;1:858-61.
Beilman et al., Experimental brown spider bite in the guinea pig: Results of treatment with dapsone or hyperbaric oxygen. J Wilderness Medicine. 1994;5:287-94.
Belikov, Abbreviated Guide to Synthetic and Natural Medications. Pharmaceutical Chemistry. Higher School. 1993;1:43-47. Russian.
Beltrami et al., Some Methylhydrazonium Salts; An Improved Synthesis of Tetramethylhydrazine. J Am Chem Soc. 1956;78:2467-68.
Bernstein et al., Daily or weekly therapy with resiquimod (R-848) reduces genital recurrences in herpes simplex virus-infected guinea pigs during and after treatment. J Infect Dis. Mar. 15, 2001;183(6):844-9. Epub Feb. 13, 2001.
Bertino et al., Principles of Cancer Therapy. Cecil Textbook of Medicine. Goldman et al., eds. 21th Ed. W.B. Saunders Company. 2000:1:1060-74.
Beutler et al., Tumor necrosis factor in the pathogenesis of infectious diseases. Crit Care Med. Oct. 1993;21(10 Suppl):S423-35.
Beutner et al., Therapeutic response of basal cell carcinoma to the immune response modifier imiquimod 5% cream. J Am Acad Dermatol. Dec. 1999;41(6):1002-7.
Beutner et al., Treatment of genital warts with an immune-response modifier (imiquimod). J Am Acad Dermatol. Feb. 1998;38(2 Pt 1):230-9.
Binder, Acute arthropod envenomation. Incidence, clinical features and management. Med Toxicol Adverse Drug Exp. May-Jun. 1989;4(3):163-73.

Bishop et al., Molecular mechanisms of B lymphocyte activation by the immune response modifier R-848. J Immunol. Nov. 15, 2000;165(10):5552-7.

Bitterman-Deutsch et al., [Brown spider bite]. Harefuah. Sep. 1990;119(5-6):137-9. Hebrew.

Booth et al., Dapsone suppresses integrin-mediated neutrophil adherence function. J Invest Dermatol. Feb. 1992;98(2):135-40.

Borkan et al., An outbreak of venomous spider bites in a citrus grove. Am J Trop Med Hyg. Mar. 1995;52(3):228-30.

Bourke et al., The toll-like receptor repertoire of human B lymphocytes: inducible and selective expression of TLR9 and TLR10 in normal and transformed cells. Blood. Aug. 1, 2003;102(3):956-63. Epub Apr. 10, 2003.

Brants, The Distribution of Tobacco Mosaic Virus (TMV) in Excised Tomato Roots Cultivated in Vitro. Tijdschr Plantenziekten, 1962;68:198-207.

Brassard et al., Interferon-α as an immunotherapeutic protein. J Leukoc Biol. Apr. 2002;71(4):565-81.

Breathnach, Azelaic acid: potential as a general antitumoural agent. Med Hypotheses. Mar. 1999;52(3):221-6.

Broughton, Management of the brown recluse spider bite to the glans penis. Mil Med. Oct. 1996;161(10):627-9.

Buckle et al., 4-hydroxy-3-nitro-2-quinolones and related compounds as inhibitors of allergic reactions. J Med Chem. Jul. 1975;18(7):726-32.

Buisson et al., Preparation and use of (S)-O-acetyllactyl chloride (Mosandl's reagent) as a chiral derivatizing agent. Tetrahedron Assym. 1999;10:2997-3002.

Bulut et al., Cooperation of Toll-like receptor 2 and 6 for cellular activation by soluble tuberculosis factor and Borrelia burgdorferi outer surface protein A lipoprotein: role of Toll-interacting protein and IL-1 receptor signaling molecules in Toll-like receptor 2 signaling. J Immunol. Jul. 15, 2001;167(2):987-94.

Burleson, Chapter 14. Influenza Virus Host Resistance Model for Assessment of Immunostimulation, and Antiviral Compounds. Methods in Immunology. 1995;2:181-202.

Buschle et al., Interferon γ inhibits apoptotic cell death in B cell chronic lymphocytic leukemia. J Exp Med. Jan. 1, 1993;177(1):213-8.

Cai et al., Evaluation of trifluoroacetic acid as an ion-pair reagent in the separation of small ionizable molecules by reversed-phase liquid chromatography. Analytica Chmica Acta. 1999;399:249-258.

Cantell et al., IFN-γ Enhances Production of IFN-α in Human Macrophages but Not in Monocytes. J Interferon and Cytokine Res. 1996;16:461-63.

Carceller et al., Design, synthesis, and structure-activity relationship studies of novel 1-[(1-acyl-4-piperidyl)methyl]-1H-2-methylimidazo[4,5-c]pyridine derivatives as potent, orally active platelet-activating factor antagonists. J Med Chem. Jan. 19, 1996;39(2):487-93.

Carrigan et al., Synthesis and in vitro pharmacology of substituted quinoline-2,4-dicarboxylic acids as inhibitors of vesicular glutamate transport. J Med Chem. May 23, 2002;45(11):2260-76.

Catarzi et al., Tricyclic heteroaromatic systems. Pyrazolo[3,4-c]quinolin-4-ones and pyrazolo[3,4-c]quinoline-1,4-diones: synthesis and benzodiazepine receptor activity. Arch Pharm (Weinheim). Dec. 1997;330(12):383-6.

Cheson et al., National Cancer Institute-sponsored Working Group guidelines for chronic lymphocytic leukemia: revised guidelines for diagnosis and treatment. Blood. Jun. 15, 1996;87(12):4990-7.

Chuang et al., Toll-like receptor 9 mediates CpG-DNA signaling. J Leukoc Biol. Mar. 2002;71(3):538-44.

Claisen, [Uber α-Methyl-isoxazol.] Berichte. 1909;42:59-69. German.

Cohen et al., Cytokine function: a study in biologic diversity. Am J Clin Pathol. May 1996;105(5):589-98.

Cole et al., Brown recluse spider envenomation of the eyelid: an animal model. Ophthal Plast Reconstr Surg. Sep. 1995;11(3):153-64.

Colotta et al., Synthesis and structure-activity relationships of a new set of 2-arylpyrazolo[3,4-c]quinoline derivatives as adenosine receptor antagonists. J Med Chem. Aug. 10, 2000;43(16):3118-24.

Cristalli et al., Adenosine deaminase inhibitors: synthesis and structure-activity relationships of imidazole analogues of erythro-9-(2-hydroxy-3-nonyl)adenine. J Med Chem. Mar. 1991;34(3):1187-92.

Dai et al., Synthesis of a novel C2-symmetric thiourea and its application in the Pd-catalyzed cross-coupling reactions with arenediazonium salts under aerobic conditions. Org Lett. Jan. 22, 2004;6(2):221-4.

Davis, Current therapy for chronic hepatitis C. Gastroenterology. Feb. 2000;118(2 Suppl 1):S104-14.

Davis et al., Heterocyclic Syntheses with Malonyl Chloride. Part VI. 3-Substituted Pyridine Derivatives from α-Methylene-nitriles. J Chem Soc. 1962:3638-44.

Davis et al., Self-administered topical imiquimod treatment of vulvar intraepithelial neoplasia. A report of four cases. J Reprod Med. Aug. 2000;45(8):619-23.

De et al., Structure-activity relationships for antiplasmodial activity among 7-substituted 4-aminoquinolines. J Med Chem. Dec. 3, 1998;41(25):4918-26.

Debol et al., Anti-inflammatory action of dapsone: inhibition of neutrophil adherence is associated with inhibition of chemoattractant-induced signal transduction. J Leukoc Biol. Dec. 1997;62(6):827-36.

De Clerq, Synthetic interferon inducers. Top Curr Chem. 1974;52:173-208.

Decker et al., Immunostimulatory CpG-oligonucleotides cause proliferation, cytokine production, and an immunogenic phenotype in chronic lymphocytic leukemia B cells. Blood. Feb. 1, 2000;95(3):999-1006.

Decker et al., Immunostimulatory CpG-oligonucleotides induce functional high affinity IL-2 receptors on B-CLL cells: costimulation with IL-2 results in a highly immunogenic phenotype. Exp Hematol. May 2000;28(5):558-68.

Delgado, Textbook of Organic Medicinal and Pharmaceutical Chemistry, Ninth Edition, Remers, ed., 1991:30-1.

Denzel et al. Imidazo [4,5-c]- and [4,5-b]pyridines. J. Heterocyclic Chem. 1977;14:813-821.

Diaz-Arrastia et al., Clinical and molecular responses in high-grade intraepithelial neoplasia treated with topical imiquimod 5%. Clin Cancer Res. Oct. 2001;7(10):3031-3.

Di Carlo et al., Neutrophils in anti-cancer immunological strategies: old players in new games. J Hematother Stem Cell Res. Dec. 2001;10(6):739-48.

Dicken et al., Reactions at High Pressures. [3+2] Dipolar Cycloaddition of Nitrones with Vinyl Ethers. J Org Chem. 1982;47:2047-51.

Dockrell et al., Imiquimod and resiquimod as novel immunomodulators. J Antimicrob Chemother. Dec. 2001;48(6):751-5.

Dorwald, "Preface." Side Reactions in Organic Synthesis. A Guide to Successful Synthesis Design. Wiley-VCH. 2005: IX.

Douglas, Introduction to Viral Diseases. In: Cecil Textbook of Medicine. Bennet et al., eds. 20th Ed. W.B. Saunders Company. 1996:2:1739-47.

Doyle et al., Toll-like receptor 3 mediates a more potent antiviral response than Toll-like receptor 4. J Immunol. Apr. 1, 2003;170(7):3565-71.

Drexler et al., Bryostatin 1 induces differentiation of B-chronic lymphocytic leukemia cells. Blood. Oct. 1989;74(5):1747-57.

Dzionek et al. BDCA-2, BDCA-3, and BDCA-4: three markers for distinct subsets of dendritic cells in human peripheral blood. J Immunol. Dec. 1, 2000;165(11):6037-46.

Edwards et al., Toll-like receptor expression in murine DC subsets: lack of TLR7 expression by CD8 alpha+DC correlates with unresponsiveness to imidazoquinolines. Eur J Immunol. Apr. 2003;33(4):827-33.

Eriks et al., Histamine H2-receptor agonists. Synthesis, in vitro pharmacology, and qualitative structure-activity relationships of substituted 4- and 5-(2-aminoethyl)thiazoles. J Med Chem. Aug. 21, 1992;35(17):3239-46.

Fecci et al., The history, evolution, and clinical use of dendritic cell-based immunization strategies in the therapy of brain tumors. J Neurooncol. Aug.-Sep. 2003;64(1-2):161-76.

Fitzgerald-Bocarsly et al., Virally-Responsive IFN-α Producing Cells in Human Blood and Tonsil Are CD11C/CD123+ Cells Identical to Precursors of Type Two Dendritic Cells (pDC2). J Interferon Cytokine Res. 1999;19(1):S117. Abstract P81.

Flo et al., Involvement of toll-like receptor (TLR) 2 and TLR4 in cell activation by mannuronic acid polymers. J Biol Chem. Sep. 20, 2002;277(38):35489-95. Epub Jun. 27, 2002.

Fonteneau et al., Human Immunodeficiency Virus Type 1 Activates Plasmacytoid Dendritic Cells and Concomitantly Induces the Bystander Maturation of Myeloid Dendritic Cells. J Virol. 2004;78(10):5223-32.

Frankel et al., The Preparation of N-Disubstituted Formamides. Tetrahedron Lett. 1959;7:5-7.

Frantz et al., Toll4 (TLR4) expression in cardiac myocytes in normal and failing myocardium. J Clin Invest. Aug. 1999;104(3):271-80.

Fu et al., Regioselective Catalytic Hydrogenation of Polycyclic Aromatic Hydocarbons under Mild conditions. J Org Chem. 1980;45:2979-803.

Fuchsberger et al., Priming Interferon-a 1 or Interferon-a 2 Enhances the Production of Both Subtypes Simultaneously. J Interferon and Cytokine Res. 1995;15:637-39.

Galose, Dapsone (diaminodiphenylsulphone DDS). Clinical Toxicology Review. 1999;21(9). 3 pages.

Gendron, Loxosceles ignali Envenomation. Am J Emerg Med. Jan. 1990;8(1):51-4.

Genevois-Borella et al., Synthesis of 1-(3-R-Amino-4-Hydroxy Butyl)thymine Acyclonucleoside. Analogs as Potential Anti-AIDS Drugs. Tetrahdron Lett. 1990;31:4879-82.

Giannini et al., Influence of the Mucosal Epithelium Microenvironment on Langerhans Cells: Implications for the Development of Squamous Intraepithelial Lesions of the Cervix. Int J Cancer. 2002;97:654-59.

Gibson et al., Cellular requirements for cytokine production in response to the immunomodulators imiquimod and S-27609. J Interferon Cytokine Res. Jun. 1995;15(6):537- 45.

Gibson et al., Plasmacytoid dendritic cells produce cytokines and mature in response to the TLR7 agonists, imiquimod and resiquimod. Cell Immunol. Jul.-Aug. 2002;218(1-2):74-86.

Gitelson et al., Chronic lymphocytic leukemia-reactive T cells during disease progression and after autologous tumor cell vaccines. Clin Cancer Res. May 2003;9(5):1656-65.

Gomez et al., Intradermal anti-loxosceles Fab fragments attenuate dermonecrotic arachnidism. Acad Emerg Med. 1999;6:1195-202.

Gorden et al., Synthetic TLR agonists reveal functional differences between human TLR7 and TLR8. J Immunol. Feb. 1, 2005;174(3):1259-68.

Gordon, Pattern recognition receptors: doubling up for the innate immune response. Cell. Dec. 27, 2002;111(7):927-30.

Gunning et al., Chemoprevention by lipoxygenase and leukotriene pathway inhibitors of vinyl carbamate-induced lung tumors in mice. Cancer Res. Aug. 1, 2002;62(15):4199-201.

Gürsel et al., Differential and competitive activation of human immune cells by distinct classes of CpG oligodeoxynucleotide. J Leukoc Biol. May 2002;71(5):813-20.

Hart, Napthyridines Hydroxynaphthyridies, Journal of Chemical Society, 1956;Part III:212-4.

Hartmann et al., Rational design of new CpG oligonucleotides that combine B cell activation with high IFN-alpha induction in plasmacytoid dendritic cells. Eur J Immunol. Jun. 2003;33(6):1633-41.

Hayashi Toll-like receptors stimulate human neutrophil function. Blood. Oct. 1, 2003;102(7):2660-69. Epub Jun. 26, 2003.

Hayes et al., Regulation of Interferon Production by Human Monocytes: Requirements for Priming for Lipopolysaccharide-Induced Production. J Leukocyte Biol. 1991;50:176-81.

Heil et al., Species-specific recognition of single-stranded RNA via toll-like receptor 7 and 8. Science. Mar. 5, 2004;303(5663):1526-9. Epub Feb. 19, 2004.

Heil et al., Synthetic immunostimulatory compounds activate immune cells via TLR7 and TLR8. 33th Annual Meeting of the Deutsche Gessellschaft Mr Immunologie, Marburg 2002, Abstract C.6.

Hemmi et al., Small anti-viral compounds activate immune cells via the TLR7 MyD88-dependent signaling pathway. Nat Immunol. Feb. 2002;3(2):196-200. Epub Jan. 22, 2002.

Hobbs et al., Comparison of hyperbaric oxygen and dapsone therapy for loxosceles envenomation. Acad Emerg Med. Aug. 1996;3(8):758-61.

Hoffman et al., Conformational requirements for histamine H2-receptor inhibitors: a structure-activity study of phenylene analogues related to cimetidine and tiotidine. J Med Chem. Feb. 1983;26(2):140-4.

Hofmanová et al., Lipoxygenase inhibitors induce arrest of tumor cells in S-phase of the cell cycle. Neoplasma. 2002;49(6):362-7.

Holladay et al., Structure-activity studies related to ABT-594, a potent nonopioid analgesic agent: effect of pyridine and azetidine ring substitutions on nicotinic acetylcholine receptor binding affinity and analgesic activity in mice. Bioorg Med Chem Lett. Oct. 6, 1998;8(19):2797-802.

Horng et al., The adaptor molecule TIRAP provides signaling specificity for Toll-like receptors. Nature. Nov. 21, 2002;420(6913):329-33.

Hornung et al., Quantitative Expression of Toll-Like Receptor 1-10 mRNA in Cellular Subsets of Human Peripheral Blood Mononuclear Cells and Sensitivity to CpG Oligodeoxynucleotides. Journal of Immunol. 2002;168:4531-37.

Houben-Weyl, Quinoline and Isoquinoline. Methoden der Organischen Chemie. 1980:271-79. German.

Houston et al., Potential inhibitors of S-adenosylmethionine-dependent methyltransferases. 8. Molecular dissections of carbocyclic 3-deazaadenosine as inhibitors of S-adenosylhomocysteine hydrolase. J Med Chem. Apr. 1985;28(4):467-71.

Huppatz, Systemic fungicides. The synthesis of certain pyrazole analogues of carboxin. Aust J Chem. 1983;36:135-47.

Iino et al., Treatment of Chronic Hepatitis C With High-Dose Interferon α-2b. Multicenter Study. Dig Dis Sci. 1993;38(4):612-18.

Ito et al., Interferon-alpha and interleukin-12 are induced differentially by Toll-like receptor 7 ligands in human blood dendritic cell subsets. J Exp Med. Jun. 3, 2002;195(11):1507-12.

Iwashita et al., Syntheses of Isoretronecanol and Lupinine. J Org Chem. 1982;47:230-33.

Jacobs, Chapter 1. The Synthesis of Acetylenes. In: Organic Reactions. New York: Wiley & Sons, Inc., 1949. vol. 5. 1-78.

Jahnsen et al., Extensive recruitment of IL-3Rαhigh dendritic-cell precursors to allergic nasal mucosa during allergen challenge. Immunology Lett. 1999;69(1):123. Abstract #32.2.

Jurk et al. Human TLR7 and TLR8 independently confer responsiveness to the antiviral compound R-848. Nat Immunol. Jun. 2002;3(6):499.

Juweid, Radioimmunotherapy of B-Cell Non-Hodgkin's Lymphoma: From Clinical Trials to Clinical Practice. J Nuclear Med. 2002;43(11):1507-29.

Katritsky et al., Comprehensive Heterocyclic Chemistry: The Structure, Reactions, Synthesis and Uses of Heterocyclic Compounds. 1984;2:586-587.

Keating et al., Long-term follow-up of patients with chronic lymphocytic leukemia treated with fludarabine as a single agent. Blood. Jun. 1, 1993;81(11):2878-84.

Kerkmann et al., Activation with CpG-A and CpG-B oligonucleotides reveals two distinct regulatory pathways of type I IFN synthesis in human plasmacytoid dendritic cells. J Immunol. May 1, 2003;170(9):4465-74.

Klausen et al., Two complementary methods of assessing periodontal bone level in rats. Scand J Dent Res. Dec. 1989;97(6):494-9.

Klinman, Immunotherapeutic uses of CpG oligodeoxynucleotides. Nat Rev Immunol. Apr. 2004;4(4):249-58.

Kloek et al., An improved method for the synthesis of stabilized primary enamines and imines. J Org Chem. 1978;43:1460-62.

Kloetzel, Reactions of nitroparaffins. I. Synthesis and reduction of some σ-nitrokenes. J Am Chem Soc. 1947;69:2271-2275.

Kornman, Host modulation as a therapeutic strategy in the treatment of periodontal disease. Clin Infect Dis. Mar. 1999;28(3):520-6.

Kourafalos et al., Synthesis of 7-aminopyrazolo[3,4-c]pyridine as a probe for the preparation of compounds of pharmacological interest. Heterocycles. 2002;57(12):2335-2343.

Krause et al., Autoimmune aspects of cytokine and anticytokine therapies. Am J Med. Oct. 1, 2003;115(5):390-7.

Krenitsky et al., Imidazo[4,5-c]pyridines (3-deazapurines) and their nucleosides as immunosuppressive and anti-inflammatory agents. J Med Chem. Jan. 1986;29(1):138-43.

Kurt-Jones et al., Role of toll-like receptor 2 (TLR2) in neutrophil activation: GM-CSF enhances TLR2 expression and TLR2-mediated interleukin 8 responses in neutrophils. Blood. Sep. 1, 2002;100(5):1860-8.

Lall et al., Serine and threonine beta-lactones: a new class of hepatitis A virus 3C cysteine proteinase inhibitors. J Org Chem. Mar. 8, 2002;67(5):1536-47.

Lee et al., p38 mitogen-activated protein kinase inhibitors—mechanisms and therapeutic potentials. Pharmacol Ther. 1999;82:389-97.

Lee et al., Saturated fatty acid activates but polyunsaturated fatty acid inhibits Toll-like receptor 2 dimerized with Toll-like receptor 6 or 1. J Biol Chem. Apr. 23, 2004;279(17):16971-9. Epub Feb. 13, 2004.

Lehner et al., The role of γΦ cells and β-chemokines in mucosal protection against SIV infection. Immunology Lett. 1999;69:25-192. Abstract 2.1.

Levy et al., Unique efficacy of Toll-like receptor 8 agonists in activating human neonatal antigen-presenting cells. Blood. Aug. 15, 2006;108(4):1284-90. Epub Apr. 25, 2006.

Leynadier et al., Allergic reactions to North African scorpion venom evaluated by skin test and specific IgE. J Allergy Clin Immunol. Jun. 1997;99(6 Pt 1):851-3. 4 pages.

Li et al., An improved protocol for the preparation of 3-pyridyl- and some arylboronic acids. J Org Chem. Jul. 26, 2002;67(15):5394-7.

Li et al., Solubility behavior of imiquimod in alkanoic acids. Pharmaceutical Research. 1997 American Association of Pharmaceutical Scientists Annual Meeting. Poster Presentation, Boston, MA, Nov. 2-6, 1997;S475:Abstract 3029.

Li et al, Synthesis, CoMFA analysis, and receptor docking of 3,5-diacyl-2, 4-dialkylpyridine derivatives as selective A3 adenosine receptor antagonists. J Med Chem. Feb. 25, 1999;42(4):706-21.

Litt et al., Mucosal delivery of vaccine antigens displayed on the surface of Lactococous lactis. Immunology Lett. 1999:69(1):61. Abstract #11.26.

Liu et al., Synthesis of halogen-substituted 3-deazaadenosine and 3-deazaguanosine analogues as potential antitumor/antiviral agents. Nucleosides Nucleotides Nucleic Acids. Dec. 2001; 20(12):1975-2000.

Loesche et al., Treatment paradigms in periodontal disease. Compend Contin Educ Dent. Mar. 1997;18(3):221-6, 228-30, 232 passim; quiz 234. Review.

Luger et al., Evidence for an epidermal cytokine network. J Invest Dermatol. Dec. 1990;95(6 Suppl):100S-104S.

Luskin et al., Olefinic Derivatives of 2,4-Diamino-s-triazines. J Org Chem. 1958;23:1032-37.

Macchia et al., Synthesis and antiviral properties of 9-[(2-methyleneaminoxyethoxy)methyl]guanine derivatives as novel Acyclovir analogues. Farmaco. Feb. 2000;55(2):104-8.

Majeski et al., Action of venom from the brown recluse spider (Loxosceles reclusa) on human neutrophils. Toxicon. 1977;15(5):423-7.

Makarenkova et al., Identification of delta- and mu- type opioid receptors on human and murine dendritic cells. J Neuroimmunol. 2001;117:68-77.

Male et al., Introduction to the Immune System. In: Immunology. Elsevier. 2006:6-7.

Masihi, Progress on novel immunomodulatory agents for HIV-1 infection and other infectious diseases. Expert Opin Ther Patents. 2003;13(6):867-82.

Masiukiewicz et al, Scalable Syntheses of $N^{\alpha}$-Benzyloxycarbonyl-$_L$-Ornithine and of $N^{\alpha}$-(9-Fluorenylmethoxy)Carbonyl-$_L$-Ornithine. Org Prep Proced Int. 2002;34:531-37.

Mataka et al., Condensation reaction of 3,4-Dibenzoyl-1-methyl-2,5-diphenylpyrrole and -1-phenylpyrazole with methylamine derivatives affording pyrrolo [3,4-c] pyridine and 2H-pyrazolo[3,4-c]- and [4,3-c]pyridines. Journal of Heterocyclic Chemistry. 1981;18(6):1073-5.

Mathur et al., Cell-mediated immune system regulation in periodontal diseases. Crit Rev Oral Biol Med. 1997;8(1):76-89.

Maynor et al., Brown recluse spider envenomation: a prospective trial of hyperbaric oxygen therapy. Acad Emerg Med. Mar. 1997;4(3):184-92.

Mbow et al., Small molecule and biologic modulators of the immune response to hepatitis C virus. Mini Rev Med Chem. May 2006;6(5):527-31.

McCarthy et al., Opioids, opioid receptors, and the immune response. Drug & Alcohol Dependence. 2001;62:111-23.

McKennon et al., A Convenient Reduction of Amino Acids and Their Derivatives. J Org Chem. 1993;58:3568-71.

McLaughlin et al., Opioid growth factor (OGF) inhibits the progression of human squamous cell carcinoma of the head and neck transplanted into nude mice. Cancer Lett. 2003;199:209-17.

Medzhitov, Toll-Like Receptors and Innate Immunity. Nature Rev Immunol. 2001;1:135-45.

Mee et al., Stille coupling made easier—the synergic effect of copper(I) salts and the fluoride ion. Angew Chem. 2004;116:1152-56.

Merigian et al., Envenomation From the Brown Recluse Spider: Review of Mechanism and Treatment Options. Am J Ther. Oct. 1996;3(10):724-734.

Miller et al., Imiquimod applied topically: a novel immune response modifier and new class of drug. Int J Immunopharmacol. Jan. 1999;21(1):1-14.

Minakawa et al., Nucleosides and Nucleotides. 184. Synthesis and Conformational Investigation of Anti-Fixed 3-Deaza-3-halopurine Ribonucleosides. J Org Chem. 1999;64:7158-72.

Moebius et al., The mysteries of sigma receptors: new family members reveal a role in cholesterol synthesis. Trends Pharmacol Sci. Mar. 1997;18(3):67-70.

Moldoveanu et al., Poly-L-lysine as a potential mucosal adjuvant. Immunology Lett. 1999;69(1):62. Abstract #11.28.

Mollick et al., MUC1-like tandem repeat proteins are broadly immunogenic in cancer patients. Cancer Immun. Mar. 17, 2003;3:3. 17 pages.

Moody et al., Lipoxygenase inhibitors prevent lung carcinogenesis and inhibit non-small cell lung cancer growth. Exp Lung Res. Jul.-Aug. 1998;24(4):617-28.

Moraczewski et al., Using Hydrogen Bonding to Control Carbamate C-N Rotamer Equilibria. Org Chem. Oct. 16, 1998;63(21):7258-7262.

Mosbech et al., [Allergy to insect stings] Ugeskr Laeger. Oct. 28, 1991;153(44):3067-71. Danish.

Muche et al., Imiquimod treatment of cutaneous T cell lymphoma. Journal of Investigative Dermatology. Jul. 2003;121(1):0975. Joint Meeting of the European Society for Dermatologi; Miami Beach, Florida, USA. Apr. 30-May 4, 2003. Abstract 0975.

Muller et al., An improved one-pot procedure for the synthesis of alkynes from aldehydes. Synlett. 1996;6:521-522.

Mutschler et al., 9.2 Anti-infectives. In: Drug Actions: Basic Principles and Therapeutic Aspects. 1995:515-80.

Muzio et al., Differential expression and regulation of toll-like receptors (TLR) in human leukocytes: selective expression of TLR3 in dendritic cells. J Immunol. Jun. 1, 2000;164(11):5998-6004.

Nagarajan et al., Condensed heterotricycles: synthesis of pyrazolo[3,4-c]quinoline derivatives. Indian Journal of Chemistry. 1992;31B:316-321.

Nagase et al., Expression and function of Toll-like receptors in eosinophils: activation by Toll-like receptor 7 ligand. J Immunol. Oct. 15, 2003;171(8):3977-82.

Nanjappan et al., An efficient synthesis of some 6-substituted 4,8-diaza-3,3,9,9-tetramethylundeca-2,10-dione dioximes (propylene amine oximes, PnAOs): Ligands for 99mTc complexes used in structure distribution relationship (SDR) studies. Tetrahedron. 1994;50(29):8617-32.

Ohana et al., Differential effect of adenosine on tumor and normal cell growth: focus on the A3 adenosine receptor. Journal of Cellular Physiology. Jan. 2001;186(1):19-23. Review.

O'Mahony et al., New patient-applied therapy for anogenital warts is rated favourably by patients. Intl J STD & AIDS. 2001;12:565-70.

Osol et al., Chapter 27: Structure-Activtiy Relationship and Drug Design. In: Remington's Pharmaceutical Sciences. 16th Ed. Mach Publishing. 1980:420-35.

Ottonello et al., Sulphonamides as anti-inflammatory agents: old drugs for new therapeutic strategies in neutrophilic inflammation? Clin Sci (Lond). Mar. 1995;88(3):331-6.

Ozinsky et al., The repertoire for pattern recognition of pathogens by the innate immune system is defined by cooperation between Toll-like receptors. Proc. Nat. Acad. Sci. 2000; 97(25):13766-71.

Page et al., Advances in the pathogenesis of periodontitis: summary of developments, clinical implications and future directions. Periodontol 2000. Jun. 1997;14:216-48.

Park et al., Immunotherapy Cancer Treatment. Reprinted from Supportive Cancer Care, Rosenbaum et al. 2001. Available at http://www.cancersupportivecare.com/immunotherapy.html. Last accessed Jul. 13, 2010. 3 pages.

Park et al., Sodium Dithionite Reduction of Nitroarenes Using Viologen as an Electron Phase-Transfer Catalyst. Tetrahedron Lett. 1993;34(46):7445-46.

Patel et al., The necrotic venom of the brown recluse spider induces dysregulated endothelial cell-dependent neutrophil activation. Differential induction of GM-CSF, IL-8, and E-selectin expression. J Clin Invest. Aug. 1994;94(2):631-42.

Patrick et al., Paragraph 10.3: Drug optimization: strategies in drug design. In: An Introduction to Medicinal Chemistry. Oxford: Oxford University Press. Jan. 2005. 200-218.

Pavletic et al., Outcome of allogeneic stem cell transplantation for B cell chronic lymphocytic leukemia. Bone Marrow Transplant. Apr. 2000;25(7):717-22.

Pawlas et al., Novel anionic annelation tactics for construction of fused heteroaromatic frameworks. 1. Synthesis of 4-substituted pyrazolo[3,4-c]quinolines, 9-substituted pyrazolo[3,4-c]quinolines, and 1,4-dihydrochromeno[4,3-c]pyrazoles. Org Chem. Jun. 15, 2001;66(12):4214-9.

Payvandi et al., Exogenous and Endogenous IL-10 Regulate IFN-α Production by Peripheral Blood Mononuclear Cells in Response to Viral Stimulation. J Immunol. 1998;160:5861-68.

Peschke et al., Synthesis and in vitro characterization of new growth hormone secretagogues derived from ipamorelin with dipeptidomimetic N-terminals. Eur J Med Chem. 1999;34:363-380.

Peterson et al., The opioid-cytokine connection. J Neuroimmunol. 1998;83:63-69.

Phillips et al., Therapy of brown spider envenomation: a controlled trial of hyperbaric oxygen, dapsone, and cyproheptadine. Ann Emerg Med. Mar. 1995;25(3):363-8.

Pickersgill et al., Preparation of functionalized, conformationally constrained DTPA analogues from L- or D-serine and trans-4-hydroxy-L-proline. Hydroxymethyl substituents on the central acetic acid and on the backbone. J Org Chem. Jun. 30, 2000;65(13):4048-57.

Poljakovic et al., iNOS and COX-2 immunoreactivity in the mice bladder and kidney after bacterial instillation. Immunology Lett. 1999;69(1):122. Abstract #31.5.

Powell et al., Compendium of excipients for parenteral formulations. PDA J Pharm Sci Technol. Sep.-Oct. 1998;52(5):238-311.

Prelog et al., Cycloalkeno-pyridine. Helv Chem Acta. 1945;28:1684-93. German.

Rees et al., Brown recluse spider bites. A comparison of early surgical excision versus dapsone and delayed surgical excision. Ann Surg. Nov. 1985;202(5):659-63.

Regan et al., Activation of p38 MAPK by feline infectious peritonitis virus regulates pro-inflammatory cytokine production in primary blood-derived feline mononuclear cells. Virology. Feb. 5, 2009;384(1):135-43. Epub Dec. 5, 2008.

Rhodes, Discovery of immunopotentiatory drugs: current and future strategies. Clin Exp Immunol. Dec. 2002;130(3):363-9.

Ribera et al., "Spontaneous" complete remissions in chronic lymphocytic leukemia: report of three cases and review of the literature. Blood Cells. 1987;12(2):471-79.

Ritter et al., A new reaction of nitriles; amides from alkenes and mononitriles. J Am Chem Soc. Dec. 1948;70(12):4045-8.

Rocca et al., Carbolines. Part VII. Ansidines, Convenient tools to synthesize fficien-β-carbolines. J Heterocyclic Chem. 1995;32:1171-1175.

Rocca et al., Connection between metalation and cross-coupling strategies. Anew convergent route to azacarbazoles. Tetrahedron. 1993;49(1):49-64.

Rollins, Chemokines. Blood. Aug. 1, 1997;90(3):909-28. Review.

Rosenberg et al., Treatment of 283 consecutive patients with metastatic melanoma or renal cell cancer using high-dose bolus interleukin 2. JAMA. Mar. 23-30, 1994;271(12):907-13.

Rothel et al., The use of recombinant ovine IL-1beta and TNF-alpha as natural adjuvants and their physiological effects in vivo. Immunol Cell Biol. Apr. 1998;76(2):167-72.

Roy et al., QSAR of adenosine receptor antagonists II: exploring physicochemical requirements for selective binding of 2-arlypyrazolo[3,4-c] quinoline derivatives with adenosine A1 and A3 receptor subtypes. QSAR & Comb Sci. 2003;22:614-621.

Royals et al., Studies in mixed ester condensations. IV. Acylations with methyl dimethoxyacetate. J Am Chem Soc. 1956;78:4161-4164.

Rozman et al., Chronic lymphocytic leukemia. N Engl J Med. Oct. 19, 1995;333(16):1052-7.

Sakthivel et al. Direct SnAr amination of fluorinated imizazo[4,5-c]pyridine nucleosides: efficient synthesis of 3-fluoro-3-3-deazaadenosine analogs. Tetrahedron Letters. May 2005;46(22):3883-3887.

Salaun et al., TLR3 Can Directly Trigger Apoptosis in Human Cancer Cells. J of Immunology. 2006;176:4894-901.

Salemink, Uber 2-Propyl-1- Und 2-Propyl-Desaza-Adenin. Recueil. 1961;80:545-55. German.

Sambhi et al., Local production of tumor necrosis factor encoded by recombinant vaccinia virus is effective in controlling viral replication in vivo. Proc Natl Acad Sci U S A. May 1, 1991;88(9):4025-9.

Sams et al., Necrotic arachnidism. J Am Acad Dermatol. Apr. 2001;44(4):561-73; quiz 573-6.

Sauder et al., Randomized, Single-Blind, Placebo-Controlled Study of Topical Application of the Immune Response Modulator Resiquimod in Healthy Adults. Antimicrobial Agents Chemo. 2003;47(12):3846-52.

Scheerlinck, Genetic adjuvants for DNA vaccines. Vaccine. Mar. 21, 2001;19(17-19):2647-56.

Scheuer et al., Application of the Ritter reaction to mesityl oxide and chalcone. J Am Chem Soc. 1957;22:674-676.

Schofield et al., Reply. Low-Dose Interferon-alpha in Chronic Myeloid Leukemia. Ann Internal Med. 1995;122(9):728-29. 1 page.

Schwandner et al., Peptidoglycan- and lipoteichoic acid-induced cell activation is mediated by toll-like receptor 2. J Biol Chem. Jun. 18, 1999;274(25):17406-9.

Seeman et al., Steric and Conformational Effects in Nicotine Chemistry. J Org Chem. 1981;46:3040-48.

Serrat et al., A highly efficient and straightforward stereoselective synthesis of novel chiral α-acetylenic ketones. Tetrahedron: Assymmetry. 1999;10:3417-30.

Severa et al., Sensitization to TLR7 agonist in IFN-beta-preactivated dendritic cells. J Immunol. May 15, 2007;178(10):6208-16.

Seymour et al., Cellular immunity and hypersensitivity as components of periodontal destruction. Oral Dis. Mar. 1996;2(1):96-101. Review.

Shelburne et al., Quantitation of Bacteroids forsythus in subgingival plaque comparison on immunoassay and quantitative polymerase chain reaction. J Microbiol Methods. 2000;39:97-107.

Sidky et al., Inhibition of murine tumor growth by an interferon-inducing imidazoquinolinamine. Cancer Res. Jul. 1, 1992;52(13):3528-33.

Siegal et al., The nature of the principal type 1 interferon-producing cells in human blood. Science. Jun. 11, 1999;284(5421):1835-7.

Sletzinger et al., The Synthesis of Isomethadone. J Am Chem Soc. 1952;74:5619-20.

Smith et al., The role of polymorphonuclear leukocytes in the lesion caused by the venom of the brown spider, Loxosceles reclusa. Lab Invest. Jan. 1970;22(1):90-3.

Sofina et al., C: Possibility of Predicting the Spectrum of Antitumor Effect of Drugs on the Basis of Experimental Data. Experimental evaluation of antitumor drugs in the USA and USSR and clinical correlations. NCI Monograph 55. NIH Publication No. 80-1933. 1980:76-8.

Sommer et al., Recent Findings on How Proinflammatory Cytokines Cause Pain: Peripheral Mechanisms in Inflammatory and Neuropathic Hyperalgesia. Neurosci Letts. 2004;361:184-87.

Sonogashira et al., A convenient synthesis of acetylenes: catalytic substitutions of acetylenic hydrogen with bromoalkenes, Iodoarenes, and bromopyridines. Tetrahedron Letts. 1975;50:4467-4470.

Soria et al., Effect of food on the pharmacokinetics and bioavailability of oral imiquimod relative to a subcutaneous dose. Int J Clin Pharmacol Ther. Oct. 2000;38(10):476-81.

Spaner et al., A phase I/II trial of TLR-7 agonist immunotherapy in chronic lymphocytic leukemia. Leukemia. 2010; 24:222-26.

Spaner et al., Immunomodulatory effects of Toll-like receptor-7 activation on chronic lymphocytic leukemia cells. Leukemia. Feb. 2006;20(2):286-95.

Spaner et al., Toll-like receptor agonists in the treatment of chronic lymphocytic leukemia. Leukemia. Jan. 2007;21(1):53-60. Epub Oct. 26, 2006.

Spivey et al., Configurationally stable biaryl analogues of 4-(dimethylamino)pyridine: A novel class of chiral nucleophilic catalysts. J Org Chem. 1999;64:9430-9443.

Spruance et al., Application of a topical immune response modifier, resiquimod gel, to modify the recurrence rate of recurrent genital herpes: a pilot study. J Infect Dis. Jul. 15, 2001;184(2):196-200. Epub Jun. 8, 2001.

Stack, Images in clinical medicine. Latrodectus mactans. N Engl J Med. Jun. 5, 1997;336(23):1649.

Stanley, Imiquimod and the imidazoquinolones: mechanism of action and therapeutic potential. Clin Exp Dermatol. Oct. 2002;27(7):571-7. Review.

Stashenko et al., Periapical inflammatory responses and their modulation. Crit Rev Oral Biol Med. 1998;9(4):498-521.

Steele et al., Lipoxygenase inhibitors as potential cancer chemopreventives. Cancer Epidemiol Biomarkers Prev. May 1999;8(5):467-83.

Steele et al., Potential use of lipoxygenase inhibitors for cancer chemoprevention. Expert Opin Investig Drugs. Sep. 2000;9(9):2121-38.

Steinmann et al., Topical imiquimod treatment of a cutaneous melanoma metastasis. J Am Acad Dermatol. Sep. 2000;43(3):555-6.

Stewart et al., Synthesis of a Carba-analog of S-Acetyl Coenzyme A, Acetonyl-dethio Coenzyme A; an Effective Inhibitor of Citrate Synthase. Liebigs Ann Chem. 1978:57-65.

Stillings et al., Substituted 1,3,4-thiadiazoles with anticonvulsant activity. 2. Aminoalkyl derivatives. J Med Chem. Nov. 1986;29(11):2280-4.

Strandtmann et al., Reaction of cyclic β-diketones with 3,4-dihydroisoquinolines and related compounds. Preparation and anticancer activity of 2-substituted 1,3-cyclohexanediones. J Med Chem. Nov. 1967;10(6):1063-5.

Stringfellow, Induction of interferon with low molecular weight compounds: fluorenone esters, ethers (tilorone), and pyrimidinones. Methods Enzymol. 1981;78(Pt A):262-84.

Ströher et al., Progress towards the treatment of Ebola haemorrhagic fever. Expert Opin Investig Drugs. Dec. 2006;15(12):1523-35.

Sugisaka et al., The Physicochemical properties of imiquimod, the first imidazoquinoline immune response modifier. Pharmaceutical Research. 1997 American Association of Pharmaceutical Scientists Annual Meeting. Poster Presentation, Boston, MA, Nov. 2-6, 1997;S475. Abstract 3030.

Surrey et al., The Synthesis of Some 3-Nitro- and 3-Amino-4-dialkylaminoalkylaminoquinoline Derivatives. J Am Chem Soc. 1951;73:2413-16.

Takeichi et al., Cytokine profiles of T-lymphocytes from gingival tissues with pathological pocketing. J Dent Res. Aug. 2000;79(8):1548-55.

Takeshita et al., Signal transduction pathways mediated by the interaction of CpG DNA with Toll-like receptor 9. Semin Immunol. Feb. 2004;16(1):17-22.

Takeuchi et al., Discrimination of bacterial lipoproteins by Toll-like receptor 6. Int Immunol. Jul. 2001;13(7):933-40.

Temple, Antimitotic agents: synthesis of imidazo[4,5-c]pyridin-6-ylcarbamates and imidazo[4,5-b]pyridin-5-ylcarbamates. J Med Chem. Feb. 1990;33(2):656-61.

Temple et al., Potential anticancer agents: 5-(N-substituted-aminocarbonyl)- and 5-(N-substituted-aminothiocarbonyl)-5,6,7,8-tetrahydrofolic acids. J Med Chem. Mar. 1988;31(3):697-700.

Thesing et al., [Darstellung und Eigenschaften des $\Delta^1$-Pyrrolin-$N$-oxyds.]. Chem Ber. 1959;92:1748-55. German.

Thiruvikraman et al., Synthesis and reactions of pyrazolo-[3,4-c]quinoline derivatives. Indian Journal of Chemistry. 1987;26B:695-696.

Tomai et al., Imiquimod: in vivo and in vitro characteristics and toxicology. In: Cutaneous Infection and Therapy. Aly et al., eds. Marcel Dekkar, Inc., New York. 1997:405-15.

Tomic et al., Sensitization of IL-2 Signaling through TLR-7 Enhances B Lymphoma Cell Immunogenicity. J Immunol. 2006;176:3830-39.

Tomioka et al., Asymmetric Alkylation of α-Alkyl β-Keto Esters. J Am Chem Soc. 1984;106:2718-19.

Totterman et al., Phorbol ester-induced differentiation of chronic lymphocytic leukaemia cells. Nature. Nov. 13, 1980;288(5787):176-8.

Tracy et al., Studies in the Pyridine Series. II. Synthesis of 2-Methyl-3-(β-Hydroxyethyl)pyridine and of the Pyridine Analog of Thiamine (Vitamin B2). J Org Chem. 1941;6:54-62.

Uno et al., TNF-related apoptosis-inducing ligand (TRAIL) frequently induces apoptosis in Philadelphia chromosome-positive leukemia cells. Blood. May 1, 2003;101(9):3658-67. Epub Dec. 27, 2002.

Urosevic et al., Imiquimod treatment induces expression of opioid growth factor receptor: a novel tumor antigen induced by interferon-alpha? Clin Cancer Res. Aug. 1, 2004;10(15):4959-70.

Van De Kerhof, New Immunomodulatory Drugs. In: Skin and Environment: Perception and Protection. Ring et al., eds., 10th EADV Congress, Oct. 10-14, Munich, Germany. 2001:1:343-48.

Vasilakos et al., Adjuvant Activities of Immune Response Modifier R-848: Comparison with CoG ODN. Cell Immunol. 2000;204:64-74.

Vieweg et al., Tumor vaccines: from gene therapy to dendritic cells—the emerging frontier. Urol Clin North Am. Aug. 2003;30(3):633-43.

Vilcek, The cytokines: An overview. In: The Cytokine Handbook, Fourth Ed. M. Lotze and A.W. Thompson (eds.), 2003;1:3-14.

Volhardt, 18-5. Amides: The Least-Reactive Carboxylic Acid Derivatives. Organic Chemistry. 1987:813.

Vollmer et al., Highly immunostimulatory CpG-free oligodeoxynucleotides for activation of human leukocytes. Antisense Nucleic Acid Drug Dev. Jun. 2002;12(3):165-75.

Wagner et al., Induction of cytokines in cynomolgus monkeys by the immune response modifiers, imiquimod, S-27609 and S-28463. Cytokine. Nov. 1997;9(11):837-45.

Wagner et al., Modulation of TH1 and TH2 Cytokine Production with the Immune Response Modifiers, R-848 and Imiguimod. Cellular Immunology. 1999;191:10-19.

Wang, Structure and Chemistry of 4-Hydroxy-6-methyl-2-pyridone. J Heterocyclic Chem. 1970;7:389-92.

Warren et al., Macrophage Growth Factor CSF-1 Stimulates Human Monocyte Production of Interferon, Tumor Necrosis Factor, and Colony Stimulating Activity. J Immunol. 1986;137(7):2281-85.

Wasserman et al., Loxoscelism and necrotic arachnidism. J Toxicol Clin Toxicol. 1983-1984;21(4-5):451-72.

Wedlock et al., Physiological effects and adjuvanticity of recombinant brushtail possum TNF-alpha. Immunol Cell Biol. Feb. 1999;77(1):28-33.

Wells, Additivity of Mutational Effects in Proteins. Biochemistry. 1990;29(37):8509-17.

Wermuth, Molecular Variations Based on Isosteric Replacements. Practice of Medicinal Chemistry.1996:203-37.

Wexler et al., Accurate identification of experimental pulmonary metastases. J Natl Cancer Inst. Apr. 1966;36(4):641-5.

Wibaut et al., Syntheses of 3,4-Dimethylpyridine, 2,3-Dimethylpridine and 2-Methyl-3-Ethylpyridine. Rec Trav Chim. 1944;63:231-38.

Wierda et al., CD40-ligand (CD154) gene therapy for chronic lymphocytic leukemia. Blood. Nov. 1, 2000;96(9):2917-24.

Wieseler-Frank et al., Central proinflammatory cytokines and pain enhancement. Neurosignals. 2005;14(4):166-74.

Williams et al., Grignard Reactions to Chiral Oxazolidine Aldehydes. Tetrahedron. 1996;52:11673-94.

Wilson et al., Spiders and spider bites. Dermatol Clin. Apr. 1990;8(2):277-86.

Wright et al., Clinical presentation and outcome of brown recluse spider bite. Ann Emerg Med. Jul. 1997;30(1):28-32.

Wu et al., Murine B16 melanoma vaccination-induced tumor immunity: identification of specific immune cells and functions involved. J Interferon Cytokine Res. Dec. 2001;21(12):1117-27.

Yamamoto et al., Essential role for TIRAP in activation of the signalling cascade shared by TLR2 and TLR4. Nature. Nov. 21, 2002;420(6913):324-9.

Yeung-Yue et al., The management of herpes simplex virus infections. Curr Opin Infect Dis. Apr. 2002;15(2):115-22.

Yutilov et al., Synthesis and some reactions of 4-nitroimidazo[4-5-c]pyridin-2-ones. CAPLUS English Abstract DN 91:175261. VINITI.1978:1193-78. Abstract Only.

Zagon et al., Immunoelectron microscopic localization of the opioid growth factor receptor (OGFr) and OGF in the cornea. Brain Res. 2003;967:37-47.

Zagon et al., Opioids and the apoptotic pathway in human cancer cells. Neuropeptides. 2003;37:79-88.

Zagon et al., The biology of the opioid growth factor receptor (OGFr). Brain Res Rev. Feb. 2002;38(3):351-76. Review.

Zagon et al., The expression and function of the OGF-OGFr axis—a tonically active negative regulator of growth—in COS cells. Neuropeptides. Oct. 2003;37(5):290-7.

Zambon, Periodontal diseases: microbial factors. Ann Periodontol. Nov. 1996;1(1):879-925.

Zarubin et al., Theoretical Study of Antagonists and Inhibitors of Mammalian Adenosine Deaminase: I. Adenosine and Its Aza- and Deazaanalogues. Russ J Bioorg Chem. 2002;28(4):284-92.

Zhang et al., Structural features of azidopyridinyl neonicotinoid probes conferring high affinity and selectivity for mammalian alpha4beta2 and Drosophila nicotinic receptors. J Med Chem. Jun. 20, 2002;45(13):2832-40.

Zhu et al., Inhibition of murine dendritic cell activation by synthetic phosphorothioate oligodeoxynucleotides. J Leukoc Biol. Dec. 2002;72(6):1154-63.

Zhu et al., Inhibition of murine macrophage nitric oxide production by synthetic oligonucleotides. J Leukoc Biol. Apr. 2002;71(4):686-94.

Ziegler-Heitbrock et al., Favorable response of early stage B CLL patients to treatment with IFN-alpha 2. Blood. May 1, 1989;73(6):1426-30.

Zyryanov et al., Heterocyclization of 1-(2'-Carbethoxyphenyl)-5-Methyltetrazole. Chemistry of Heterocylic Compounds. English Edition. 1981;16(12):1286-88.

NITROGEN CONTAINING HETEROCYCLYL SUBSTITUTED IMIDAZOQUINOLINES AND IMIDAZONAPHTHYRIDINES

CROSS-REFERENCE TO RELATED APPLICATIONS

This application is the National Stage of International Application No. PCT/US2005/020912, filed Jun. 15, 2005, which claims priority to U.S. Provisional Application Ser. No. 60/579,829, filed on Jun. 15, 2004 which is incorporated herein by reference in its entirety.

BACKGROUND

In the 1950's the 1H-imidazo[4,5-c]quinoline ring system was developed and 1-(6-568-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers, rendering them useful in the treatment of a variety of disorders.

There continues to be interest in and a need for compounds that have the ability to modulate the immune response, by induction of cytokine biosynthesis or other mechanisms.

SUMMARY OF THE INVENTION

It has now been found that certain nitrogen-containing heterocyclyl substituted imidazoquinoline and imidazonaphthyridine compounds modulate cytokine biosynthesis. Such compounds are of the following Formula I:

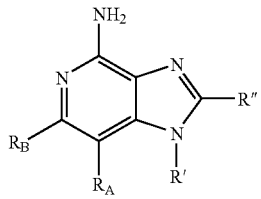

I wherein $R_A$, $R_B$, R', and R" are as defined below; and pharmaceutically acceptable salts thereof.

The compounds of Formula I are useful, for example, as immune response modifiers (IRMs) due to their ability to modulate cytokine, biosynthesis (e.g., induce or inhibit the biosynthesis or production of one or more cytokines) and otherwise modulate the immune response when administered to animals. Compounds can be tested, for example, using the test procedures described in the Examples Section. Compounds can be tested for induction of cytokine biosynthesis by incubating human PBMC in a culture with the compound(s) at a concentration range of 30 to 0.014 µM and analyzing for interferon (α) or tumor necrosis factor (α) in the culture supernatant. Compounds can be tested for inhibition of cytokine biosynthesis by incubating mouse macrophage cell line Raw 264.7 in a culture with the compound(s) at a single concentration of, for example, 5 µM and analyzing for tumor necrosis factor (α) in the culture supernatant. The ability to modulate cytokine biosynthesis, for example, induce the biosynthesis of one or more cytokines, makes the compounds useful in the treatment of a variety of conditions such as viral diseases and neoplastic diseases, that are responsive to such changes in the immune response.

The present invention further provides pharmaceutical compositions containing an effective amount of a compound of Formula I and methods of inducing cytokine biosynthesis in an animal, treating a viral infection and/or treating a neoplastic disease in an animal by administering an effective amount of a compound of Formula I to the animal.

In addition, methods of synthesizing compounds of Formula I and intermediates useful in the synthesis of these compounds are provided.

As used herein, "a", "an", "the", "at least one", and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formula I:

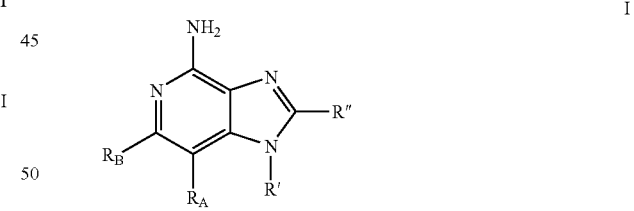

I as well as more specific compounds of the following Formulas (II, IIa, III, and IV):

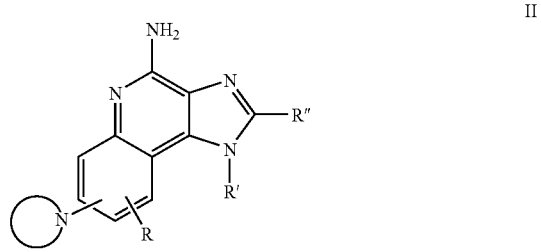

II

-continued

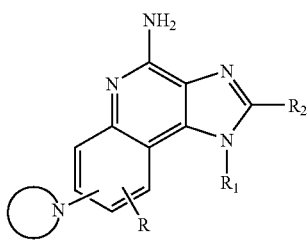

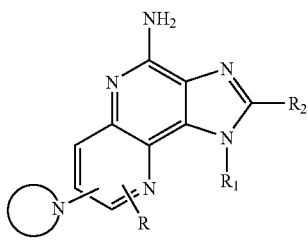

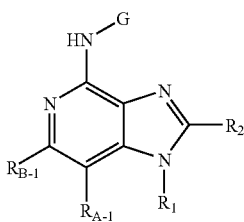

wherein $R_A$, $R_B$, $R_{A-1}$, $R_{B-1}$, R', R", R, $R_1$, $R_2$,

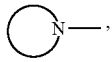

and G are as defined below, and pharmaceutically acceptable salts thereof.

In one embodiment, the present invention provides a compound of Formula (I):

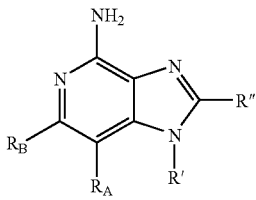

I wherein:

$R_A$ and $R_B$ taken together form a fused benzene ring or fused pyridine ring wherein the benzene ring or pyridine ring is substituted by one

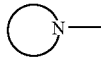

group, or substituted by one

IIa group and one R group;

III is a heterocyclic ring system wherein the ring containing the nitrogen atom bonded to the imidazoquinoline or imidazonaphthyridine radical of the compound of Formula I is unsaturated or partially saturated, and wherein the heterocyclic ring system is mono-, bi-, or tricyclic, and can contain 4 to 14 ring atoms, up to 2 of which, in addition to the nitrogen atom bonded to the imidazoquinoline or imidazonaphthyridine radical, are optionally a heteroatom selected from N, O, and S, and wherein the heterocyclic ring system is unsubstituted or substituted by one or more substituents selected from the group consisting of:

IV alkoxy,
alkylenedioxy,
hydroxy,
nitro,
oxo,
thioxo,
—$R_4$,
—Y—$R_4$,
—X—Y—$R_4$,
=N-Q-$R_4$,
=N—CN, and
=N—OH;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, heterocyclyl, and heterocyclylalkylenyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, heterocyclyl, and heterocyclylalkylenyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—O—S(O)$_2$—,
—N($R_8$)-Q-,

—C(R$_6$)—N(R$_8$)—,
—O—C(R$_6$)—N(R$_8$)—,
—C(R$_6$)—N(OR$_9$)—,

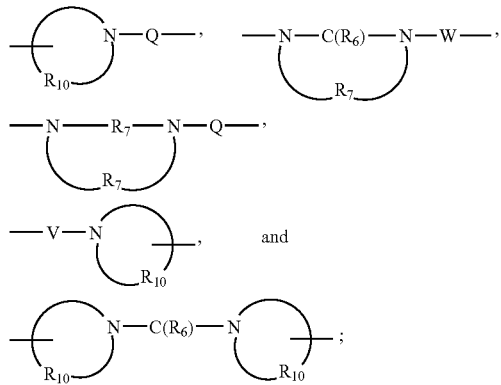

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of a bond, —C(R$_6$)—, —O—C(R$_6$)—, —N(R$_8$)—C(R$_6$)—, and —S(O)$_2$—;

W is selected from the group consisting of a bond, —C(O)—, and —(O)$_2$—;

R$_6$ is selected from the group consisting of =O and =S;

R$_7$ is C$_{2-7}$ alkylene;

R$_8$ is selected from the group consisting of hydrogen, alkyl, alkoxyalkylenyl, and arylalkylenyl;

R$_9$ is selected from the group consisting of hydrogen and alkyl;

R$_{10}$ is C$_{3-8}$ alkylene;

R is selected from the group consisting of hydrogen, alkyl, alkoxy, trifluoromethyl, chloro, fluoro, and hydroxy; and R' and R" are independently selected from the group consisting of hydrogen and non-interfering substituents;

or a pharmaceutically acceptable salt thereof.

In another embodiment, the present invention provides a compound of Formula (II):

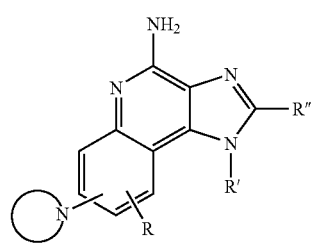

II wherein:

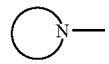

is a heterocyclic ring system wherein the ring containing the nitrogen atom bonded to the imidazoquinoline radical of the compound of Formula II is unsaturated or partially saturated, and wherein the heterocyclic ring system is mono-, bi-, or tricyclic, and can contain 4 to 14 ring atoms, up to 2 of which, in addition to the nitrogen atom bonded to the imidazoquinoline radical, are optionally a heteroatom selected from N, O, and S, and wherein the heterocyclic ring system is unsubstituted or substituted by one or more substituents selected from the group consisting of:
alkoxy,
alkylenedioxy,
hydroxy,
nitro,
oxo,
thioxo,
—R$_4$,
—Y—R$_4$,
—X—Y—R$_4$,
=N-Q-R$_4$,
=N—CN, and
=N—OH;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, heterocyclyl, and heterocyclylalkylenyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, heterocyclyl, and heterocyclylalkylenyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino) alkyleneoxy, and in the case of alkyl, alkenyl, alkynyl, and heterocyclyl, oxo;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:
—O—,
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—O—S(O)$_2$—,
—N(R$_8$)-Q-,
—C(R$_6$)—N(R$_8$)—,
—O—C(R$_6$)—N(R$_8$)—,
—C(R$_6$)—N(OR$_9$)—,

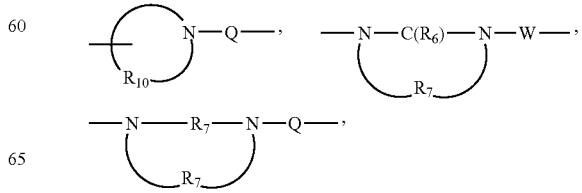

-continued

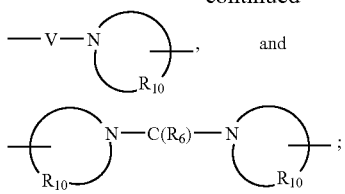
and

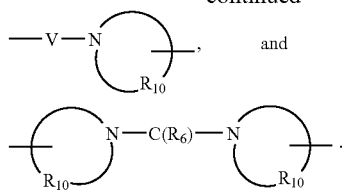
and

Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—;

V is selected from the group consisting of a bond, —C($R_6$)—, —O—C($R_6$)—, —N($R_8$)—C($R_6$)—, and —S(O)$_2$—;

W is selected from the group consisting of a bond, —C(O)—, and —S(O)$_2$—;

each $R_6$ is independently selected from the group consisting of =O and =S;

each $R_7$ is independently $C_{2-7}$ alkylene;

each $R_8$ is independently selected from the group consisting of hydrogen, alkyl, alkoxyalkylenyl, and arylalkylenyl;

$R_9$ is selected from the group consisting of hydrogen and alkyl;

each $R_{10}$ is independently $C_{3-8}$ alkylene;

R is selected from the group consisting of hydrogen, alkyl, alkoxy, trifluoromethyl, chloro, fluoro, and hydroxy; and R' and R'' are independently selected from the group consisting of hydrogen and non-interfering substituents;

or a pharmaceutically acceptable salt thereof.

For certain embodiments of Formula II, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

V is selected from the group consisting of —C($R_6$)—, —O—C($R_6$)—, —N($R_8$)—C($R_6$)—, and —S(O)$_2$—; and Y is selected from the group consisting of —S(O)$_{0-2}$—, —S(O)$_2$—N($R_8$)—, —C($R_6$)—, —C($R_6$)—O—, —O—C($R_6$)—, —O—C(O)—O—, —O—S(O)$_2$—, —N($R_8$)-Q-, —C($R_6$)—N($R_8$)—, —O—C($R_6$)—N($R_8$)—, —C($R_6$)—N(O$R_9$)—,

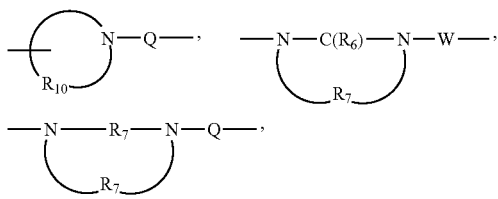

In another embodiment, the present invention provides a compound of Formula (IIa):

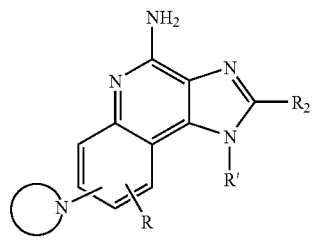

IIa wherein:

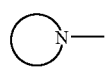

is a heterocyclic ring system wherein the ring containing the nitrogen atom bonded to the imidazoquinoline radical of the compound of Formula I is unsaturated or partially saturated, and wherein the heterocyclic ring system is mono-, bi-, or tricyclic, and can contain 4 to 14 ring atoms, up to 2 of which, in addition to the nitrogen atom bonded to the imidazoquinoline radical, are optionally a heteroatom selected from N, O, and S, and wherein the heterocyclic ring system is unsubstituted or substituted by one or more substituents selected from the group consisting of:
  alkoxy,
  alkylenedioxy,
  hydroxy,
  nitro,
  oxo,
  thioxo,
  —$R_4$,
  —Y—$R_4$,
  —X—Y—$R_4$,
  =N-Q-$R_4$,
  =N—CN, and
  =N—OH;

$R_1$ is selected from the group consisting of:
  —$R_4$,
  —X—$R_4$,
  —X—Y—$R_4$,
  —X—Y—X—Y—$R_4$, and
  —X—$R_5$;

$R_2$ is selected from the group consisting of:
  —$R_4$,
  —X—$R_4$,
  —X—Y—$R_4$, and
  —X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:
—O—,
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—O—S(O)$_2$—,
—N(R$_8$)-Q-,
—C(R$_6$)—N(R$_8$)—,
—O—C(R$_6$)—N(R$_8$)—,
—C(R$_6$)—N(OR$_9$)—,

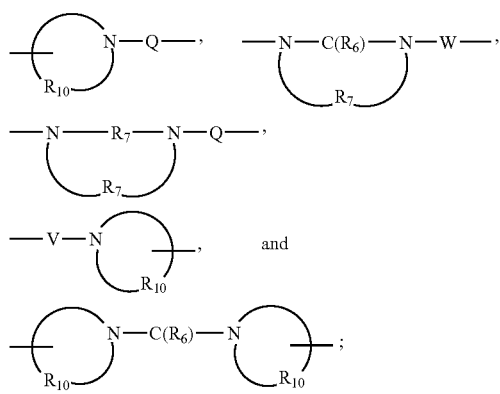

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, heterocyclyl, and heterocyclylalkylenyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, heterocyclyl, and heterocyclylalkylenyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of a bond, —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—;

each a and each b is independently an integer from 1 to 6 with the proviso that a+b in each ring is ≦7;

R$_6$ is selected from the group consisting of =O and =S;

R$_7$ is C$_{2-7}$ alkylene;

R$_8$ is selected from the group consisting of hydrogen, alkyl, alkoxyalkylenyl, and arylalkylenyl;

R$_9$ is selected from the group consisting of hydrogen and alkyl;

R$_{10}$ is C$_{3-8}$ alkylene; and

R is selected from the group consisting of hydrogen, alkyl, alkoxy, trifluoromethyl, chloro, fluoro, and hydroxy;

or a pharmaceutically acceptable salt thereof.

For certain embodiments of Formula IIa, R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

V is selected from the group consisting of —C(R$_6$)—, —O—C(R$_6$)—, —N(R$_8$)—C(R$_6$)—, and —S(O)$_2$—; and Y is selected from the group consisting of —S(O)$_{0-2}$—, —S(O)$_2$—N(R$_8$)—, —C(R$_6$)—, —C(R$_6$)—O—, —O—C(R$_6$)—, —O—C(O)—O—, —O—S(O)$_2$—, —N(R$_8$)-Q-, —C(R$_6$)—N(R$_8$)—, —O—C(R$_6$)—N(R$_8$)—, —C(R$_6$)—N(OR$_9$)—,

In another embodiment, the present invention provides a compound of Formula (III):

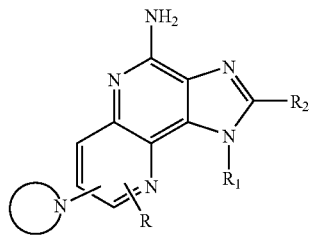

wherein:

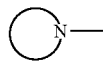

is a heterocyclic ring system wherein the ring containing the nitrogen atom bonded to the imidazonaphthyridine radical of the compound of Formula I is unsaturated or partially saturated, and wherein the heterocyclic ring system is mono-, bi-, or tricyclic, and can contain 4 to 14 ring atoms, up to 2 of which, in addition to the nitrogen atom bonded to the imidazonaphthyridine radical, are optionally a heteroatom selected from N, O, and S, and wherein the heterocyclic ring system is unsubstituted or substituted by one or more substituents selected from the group consisting of:
alkoxy,
alkylenedioxy,
hydroxy,
nitro,
oxo,
thioxo,
—$R_4$,
—Y—$R_4$,
—X—Y—$R_4$,
=N-Q-$R_4$,
=N—CN, and
=N—OH;
$R_1$ is selected from the group consisting of:
—$R_4$,
—X—$R_4$,
—X—Y—$R_4$,
—X—Y—X—Y—$R_4$, and
—X—$R_5$;
$R_2$ is selected from the group consisting of:
—$R_4$,
—X—$R_4$,
—X—Y—$R_4$, and
—X—$R_5$;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—O—S(O)$_2$—,
—N($R_8$)-Q-,
—C($R_6$)—N($R_8$)—,
—O—C($R_6$)—N($R_8$)—,
—C($R_6$)—N(OR$_9$)—,

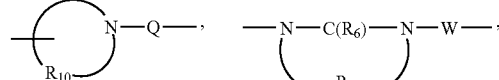

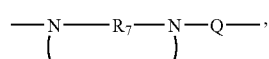

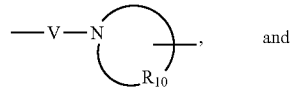

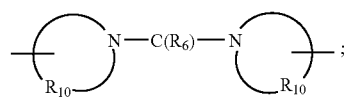

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, heterocyclyl, and heterocyclylalkylenyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, heterocyclyl, and heterocyclylalkylenyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
$R_5$ is selected from the group consisting of:

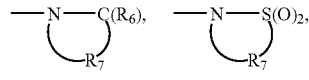

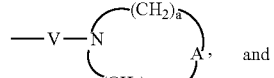

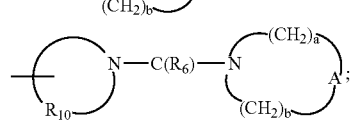

A is selected from the group consisting of —O—, —C(O)—, —S(O)$_{0-2}$—, —CH$_2$—, and —N($R_4$)—;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(OR$_9$)—;
V is selected from the group consisting of a bond, —C($R_6$)—, —O—C($R_6$)—, —N($R_8$)—C($R_6$)—, and —S(O)$_2$—;
W is selected from the group consisting of a bond, —C(O)—, and —S(O)$_2$—;

each a and each b is independently an integer from 1 to 6 with the proviso that a+b in each ring is ≦7;

$R_6$ is selected from the group consisting of =O and =S;

$R_7$ is $C_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl;

$R_{10}$ is $C_{3-8}$ alkylene; and

R is selected from the group consisting of hydrogen, alkyl, alkoxy, trifluoromethyl, chloro, fluoro, and hydroxy;

or a pharmaceutically acceptable salt thereof.

For certain embodiments, the present invention provides a compound (which is a prodrug) of the Formula (IV):

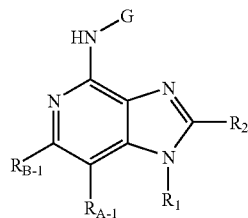

IV wherein:

G is selected from the group consisting of:

—C(O)—R''',

α-aminoacyl,

α-aminoacyl-α-aminoacyl,

—C(O)—O—R''',

—C(O)—N(R'''')R''',

—(=NY')—R''',

—CH(OH)—C(O)—OY',

—CH(O$C_{1-4}$ alkyl)$Y_0$,

—$CH_2Y_1$, and

—CH($CH_3$)$Y_1$;

R''' and R'''' are independently selected from the group consisting of $C_{1-10}$ alkyl, $C_{3-7}$ cycloalkyl, and benzyl, each of which may be unsubstituted or substituted by one or more substitutents selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, halo$C_{1-4}$ alkylenyl, halo$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —S(O)$_2$—$NH_2$, with the proviso that R'''' can also be hydrogen;

α-aminoacyl is an acyl group derived from an amino acid selected from the group consisting of racemic, D-, and L-amino acids;

Y' is selected from the group consisting of hydrogen, $C_{1-6}$ alkyl, and benzyl;

$Y_0$ is selected from the group consisting of $C_{1-6}$ alkyl, carboxy$C_{1-6}$ alkylenyl, amino$C_{1-4}$ alkylenyl, mono-N-$C_{1-6}$ alkylamino$C_{1-4}$ alkylenyl, and di-N,N-$C_{1-6}$ alkylamino$C_{1-4}$ alkylenyl;

$Y_1$ is selected from the group consisting of mono-N-$C_{1-6}$ alkylamino, di-N,N-$C_{1-6}$ alkylamino, morpholin-4-yl, piperidin-1-yl, pyrrolidin-1-yl, and 4-$C_{1-4}$ alkylpiperazin-1-yl;

$R_{A-1}$ and $R_{B-1}$ taken together form a fused benzene ring or fused pyridine ring wherein the fused pyridine ring is

wherein the highlighted bond indicates the position where the ring is fused, and wherein the benzene ring or pyridine ring is substituted by one

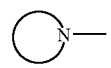

group, or substituted by one

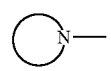

group and one R group;

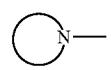

is a heterocyclic ring system wherein the ring containing the nitrogen atom bonded to the imidazoquinoline radical of the compound of Formula I is unsaturated or partially saturated, and wherein the heterocyclic ring system is mono-, bi-, or tricyclic, and can contain 4 to 14 ring atoms, up to 2 of which, in addition to the nitrogen atom bonded to the imidazoquinoline radical, are optionally a heteroatom selected from N, O, and S, and wherein the heterocyclic ring system is unsubstituted or substituted by one or more substituents selected from the group consisting of:

alkoxy, alkylenedioxy, hydroxy, nitro, oxo, thioxo,

—$R_4$,

—Y—$R_4$,

—X—Y—$R_4$,

=N-Q-$R_4$,

=N—CN, and

=N—OH;

$R_1$ is selected from the group consisting of:

—$R_4$,

—X—$R_4$,

—X—Y—$R_4$,

—X—Y—X—Y—$R_4$, and

—X—$R_5$;

$R_2$ is selected from the group consisting of:

—$R_4$,

—X—$R_4$,

—X—Y—$R_4$, and

—X—$R_5$;

X is selected from the group consisting of alkylene, alkenylene, alkynylene, arylene, heteroarylene, and heterocylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of:
—O—,
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—O—S(O)$_2$—,
—N(R$_8$)-Q-,
—C(R$_6$)—N(R$_8$)—,
—O—C(R$_6$)—N(R$_8$)—,
—C(R$_6$)—N(OR$_9$)—,

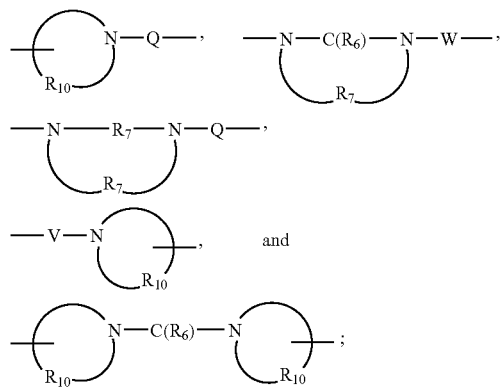

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, heterocyclyl, and heterocyclylalkylenyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, heterocyclyl, and heterocyclylalkylenyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
R$_5$ is selected from the group consisting of:

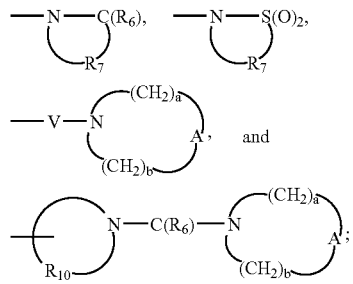

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of a bond, —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—;
each a and each b is independently an integer from 1 to 6 with the proviso that a+b in each ring is ≦7;
R$_6$ is selected from the group consisting of =O and =S;
R$_7$ is C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene; and
R is selected from the group consisting of hydrogen, alkyl, alkoxy, trifluoromethyl, chloro, fluoro, and hydroxy;
or a pharmaceutically acceptable salt thereof.

For any of the compounds presented herein, each one of the following variables (e.g., X, Y, Y', R$_A$, R$_B$, R', R'', R$_1$, R$_2$, Q, R$_4$, R$_{3b}$, G, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

In some embodiments of Formula I or Formula II, R' is selected from the group consisting of:
—R$_4$,
—X—R$_4$,
—X—Y—R$_4$,
—X—Y—X—Y—R$_4$, and
—X—R$_5$;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of:
—O—,
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—O—S(O)$_2$—,
—N(R$_8$)-Q-,
—C(R$_6$)—N(R$_8$)—,
—O—C(R$_6$)—N(R$_8$)—,
—C(R$_6$)—N(OR$_9$)—,

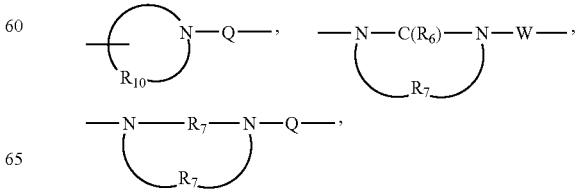

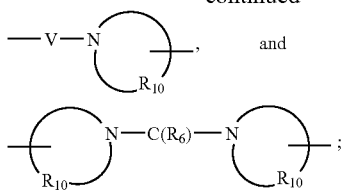

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, heterocyclyl, and heterocyclylalkylenyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, heterocyclyl, and heterocyclylalkylenyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

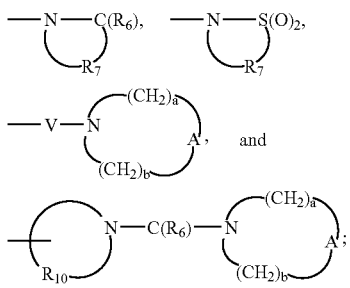

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of a bond, —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7.

In some embodiments of Formula I or Formula II, R″ is selected from the group consisting of:
—R$_4$,
—X—R$_4$,
—X—Y—R$_4$, and
—X—R$_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:
—O—,
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—O—S(O)$_2$—,
—N(R$_8$)-Q-,
—C(R$_6$)—N(R$_8$)—,
—O—C(R$_6$)—N(R$_8$)—,
—C(R$_6$)—N(OR$_9$)—,

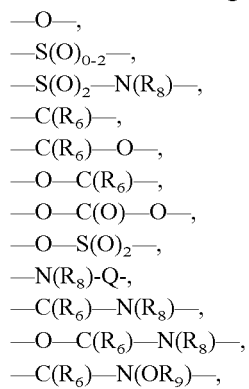
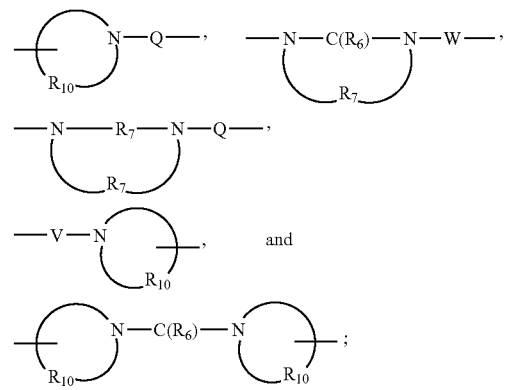

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, heterocyclyl, and heterocyclylalkylenyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, heterocyclyl, and heterocyclylalkylenyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

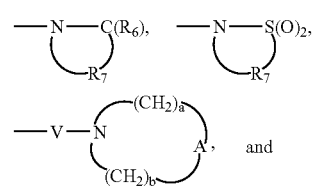

-continued

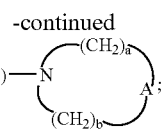

$R_6$ is selected from the group consisting of =O and =S;

$R_7$ is $C_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl;

$R_{10}$ is $C_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of a bond, —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7.

In some embodiments, including any one of the above embodiments of Formulas I, II, IIa, III, or IV, the heterocyclic ring system,

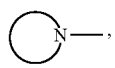

contains 4 to 13 ring atoms, in some embodiments the heterocyclic ring system contains 4 to 12 ring atoms, and in some embodiments the heterocyclic ring system contains 4 to 11 ring atoms.

In some embodiments, including any one of the above embodiments of Formulas I, II, IIa, III, or IV, the heterocyclic ring system,

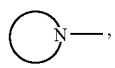

is a 4 to 9 membered monocyclic ring, in some embodiments the heterocyclic ring system is a 6 to 11 membered bicyclic ring, and in some embodiments the heterocyclic ring system is an 8 to 14 membered tricyclic ring.

In some embodiments, including any one of the above embodiments of Formulas I, II, IIa, III, or IV, the heterocyclic ring system,

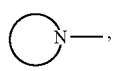

is a 5 to 7 membered monocyclic ring.

In some embodiments, including any one of the above embodiments of Formulas II, IIa, III, or IV,

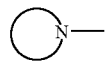

is at the 7-position; wherein the 7-position is as shown in the following structures:

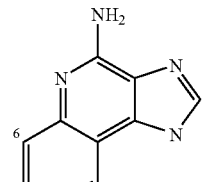

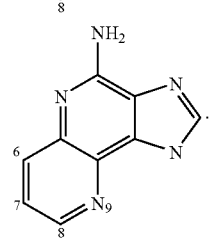

In some embodiments, including any one of the above embodiments of Formulas IIa, III, or IV, $R_1$ is selected from the group consisting of alkyl, hydroxyalkyl, alkoxyalkylenyl, arylalkylenyl, aryloxyalkylenyl, heterocyclylalkylenyl, —X—Y—R$_4$, and —X—R$_5$; wherein X is alkylene; Y is selected from the group consisting of —S(O)$_{0-2}$—, —N(R$_8$)-Q-, and

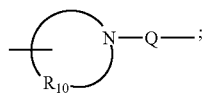

$R_4$ is selected from the group consisting of alkyl, aryl, and heteroaryl; and $R_5$ is selected from the group consisting of

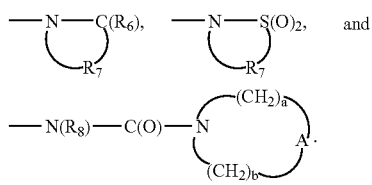

For certain embodiments, including any one of the above embodiments of Formulas IIa, III, or IV, $R_1$ is selected from the group consisting of alkyl, hydroxyalkyl, alkoxyalkylenyl, and heterocyclylalkylenyl. For certain of these embodiments, $R_1$ is selected from the group consisting of propyl, 2-methylpropyl, 2-hydroxy-2-methylpropyl, 2,3-dihydroxypropyl, 3-isopropoxypropyl, and tetrahydropyran-4-ylmethyl.

In some embodiments, including any one of the above embodiments of Formulas IIa, III, or IV, $R_2$ is $R_4$.

For certain embodiments, including any one of the above embodiments of Formulas IIa, III, or IV, $R_2$ is selected from the group consisting of hydrogen, alkyl, alkoxyalkylenyl, and hydroxyalkylenyl.

For certain embodiments, including any one of the above embodiments of Formulas IIa, III, or IV, $R_2$ is selected from the group consisting of hydrogen, $C_{1-4}$ alkyl, $C_{1-4}$ alkyl-O—$C_{1-4}$ alkylenyl, and HO—$C_{1-4}$ alkylenyl. For certain of these embodiments, $R_2$ is selected from the group consisting of hydrogen, methyl, ethyl, n-propyl, n-butyl, ethoxymethyl, methoxymethyl, 2-methoxyethyl, hydroxymethyl, and 2-hydroxyethyl.

In some embodiments, including any one of the above embodiments of Formulas I, II, IIa, III, or IV,

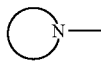

is selected from the group consisting of:

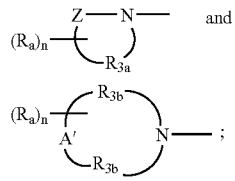

wherein:

Z is selected from the group consisting of —C(O)—, —C(S)—, —S(O)$_{0-2}$—, —OC(O)—, —N(Q-R$_4$)—C(O)—, —N(Q-R$_4$)—C(S)—, and —N(Q-R$_4$)—S(O)$_2$—;

A' is selected from the group consisting of —O—, —C(O)—, —CH$_2$—, —S(O)$_{0-2}$—, —N(Q-R$_4$)—, and —C(O)—N(Q-R$_4$)—;

$R_{3a}$ is $C_{2-7}$ alkylene;

each $R_{3b}$ is independently $C_{1-5}$ alkylene wherein both $R_{3b}$ groups combined have a total of up to seven carbon atoms;

$R_a$ is selected from the group consisting of:
alkoxy,
alkylenedioxy,
hydroxy,
nitro,
oxo,
thioxo,
—$R_4$,
—Y—$R_4$,
—X—Y—$R_4$,
=N-Q-$R_4$,
=N—CN, and
=N—OH; and n is 0 or 1; wherein $R_4$, Q, X, and Y are as defined in Formulas I-IV. In certain of these embodiments $R_a$ is hydroxy, alkoxy, oxo, or $R_4$. In certain embodiments n is 0. In certain embodiments $R_4$-Q- is selected from the group consisting of hydrogen, alkyl, acyl, alkylsulfonyl, and arylsulfonyl. In certain embodiments

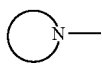

is selected from the group consisting of:

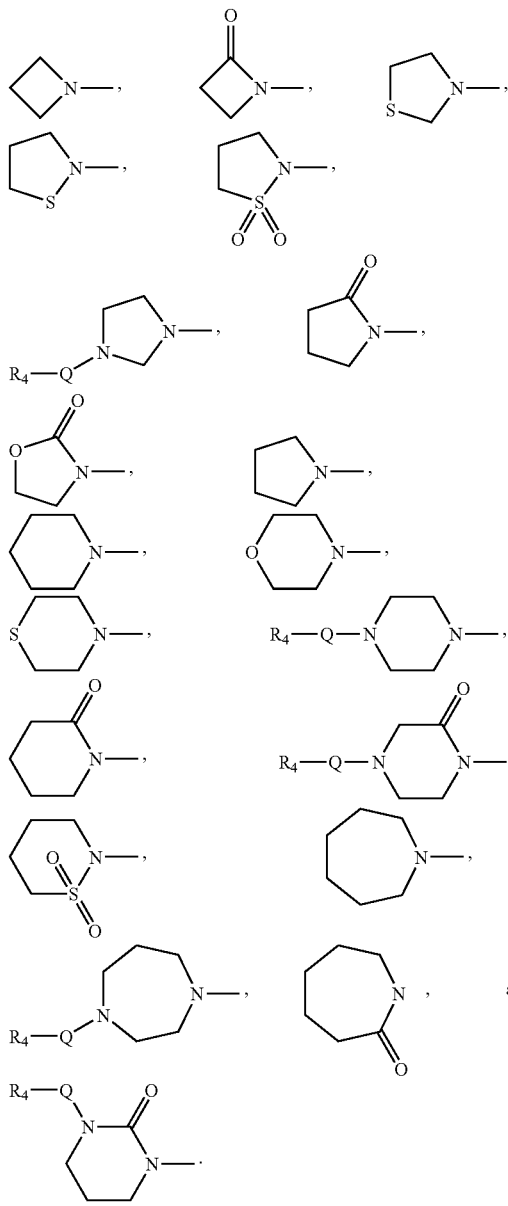

wherein $R_4$, and Q are as defined in Formulas I-IV, and in certain of these embodiments $R_4$-Q- is selected from the group consisting of hydrogen, alkyl, acyl, alkylsulfonyl, and arylsulfonyl. In certain of these embodiments,

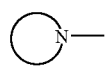

is at the 7-position.

In certain embodiments, including any one of the above embodiments,

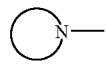

is selected from the group consisting of:

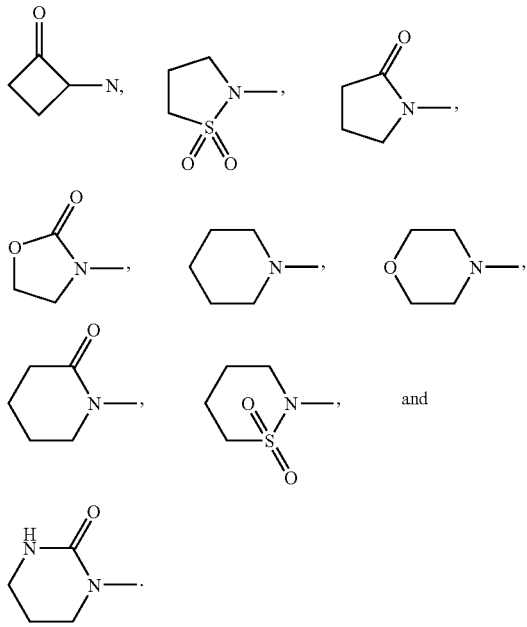

In certain embodiments, including any one of the above embodiments except where excluded, is selected from the group consisting of:

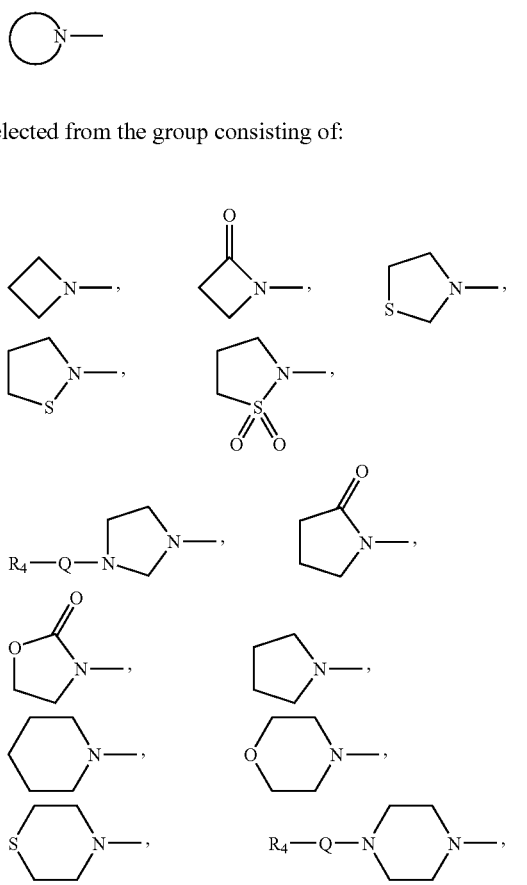

In some embodiments, including any one of the above embodiments of Formulas I, II, IIa, III, or IV, R is hydrogen.

In some embodiments, including any one of the above embodiments of Formulas IIa, III, or IV, $R_1$ is selected from the group consisting of alkyl, hydroxyalkyl, alkoxyalkylenyl, arylalkylenyl, aryloxyalkylenyl, heterocyclylalkylenyl, —X—Y—$R_4$, and —X—$R_5$; wherein X is alkylene; Y is selected from the group consisting of —S(O)$_{0-2}$—, —N($R_8$)-Q-, and

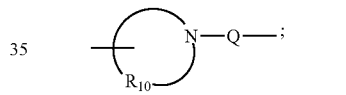

$R_4$ is selected from the group consisting of alkyl, aryl, and heteroaryl; and $R_5$ is selected from the group consisting of —N—C($R_6$),  —N—S(O)$_2$,  and
 |              |
 $R_7$          $R_7$ —N($R_8$)—C(O)—N⟨(CH$_2$)$_a$⟩A.
              ⟨(CH$_2$)$_b$⟩

In certain embodiments $R_1$ is —X—Y—$R_4$. In certain embodiments —X— is $C_{2-6}$ alkylene. In certain embodiments $R_1$ is —X—Y—$R_4$, and —X— is $C_{2-6}$ alkylene. In certain embodiments —X— is $C_{2-4}$ alkylene. In certain embodiments —X— is —CH$_2$C(CH$_3$)$_2$—. In certain embodiments —Y— is —S(O)$_{0-2}$— or —NR$_8$-Q-. In certain embodiments Y— is —N($R_8$)—C(O)—, —N($R_8$)—S(O)$_2$—, or —N($R_8$)—C(O)—N($R_8$)—. In certain embodiments $R_8$ is hydrogen. In certain embodiments $R_4$ is $C_{1-6}$ alkyl. In certain embodiments $R_4$ is methyl, isopropyl, or cyclohexyl. In certain embodiments —X— is $C_{2-6}$ alkylene, —Y— is —NH—S(O)$_2$—, and $R_4$ is $C_{1-6}$ alkyl. In certain embodiments —X— is —CH$_2$C(CH$_3$)$_2$—, —Y— is —NH—S(O)$_2$—, and $R_4$ is $C_{1-6}$ alkyl. In certain embodiments —X— is $C_{2-6}$ alkylene, —Y— is —NH—C(O)—, and $R_4$ is $C_{1-6}$ alkyl. In certain embodiments —X— is —CH$_2$C(CH$_3$)$_2$—, —Y— is —NH—C(O)—, and $R_4$ is $C_{1-6}$ alkyl. In certain embodiments —X— is $C_{2-6}$ alkylene, —Y— is —NH—C(O)—NH—, and $R_4$ is $C_{1-6}$ alkyl. In certain embodiments —X— is —CH$_2$C(CH$_3$)$_2$—, —Y— is —NH—C(O)—NH—, and 4 is $C_{1-6}$ alkyl. In certain embodiments $R_1$ is —(CH$_2$)$_4$—NH—S(O)$_2$—CH$_3$, —CH$_2$C(CH$_3$)$_2$—NH—S(O)$_2$—CH$_3$, —CH$_2$C(CH$_3$)$_2$—NH—C(O)—NH—CH(CH$_3$)$_2$, or —CH$_2$C(CH$_3$)$_2$—NH—C(O)

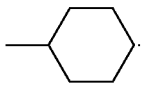

In certain embodiments, including any one of the above embodiments of Formulas IIa, III, or IV, $R_1$ is —X—$R_5$. In certain embodiments, —X— is $C_{2-6}$ alkylene. In certain embodiments, —X— is $C_{2-4}$ alkylene. In certain embodiments, —X— is —CH$_2$C(CH$_3$)$_2$—. In certain embodiments, $R_5$ is

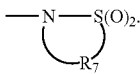

In certain embodiments, $R_5$ is selected from the group consisting of:

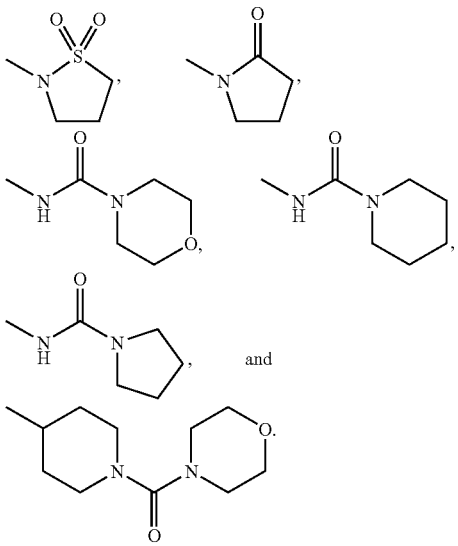

In some embodiments, including any one of the above embodiments of Formulas IIa, III, or IV, $R_1$ is alkyl, hydroxyalkyl, alkoxyalkylenyl, or aryloxyalkylenyl. In certain embodiments $R_1$ is $C_{1-6}$ alkyl, $C_{1-6}$ hydroxyalkyl, $C_{1-4}$ alkyl-O—$C_{1-4}$ alkylenyl, or aryl-O—$C_{1-4}$ alkylenyl. In certain embodiments $R_1$ is alkyl or hydroxyalkyl. In certain embodiments $R_1$ is $C_{1-4}$ alkyl or $C_{1-4}$ hydroxyalkyl. In certain embodiments $R_1$ is 2-methylpropyl, 2-hydroxy-2-methylpropyl, 3-methoxypropyl, or phenoxyethyl. In certain embodiments $R_1$ is 2-methylpropyl. In certain embodiments $R_1$ is 2-hydroxy-2-methylpropyl.

In some embodiments, including any one of the above embodiments of Formulas IIa, III, or IV, $R_2$ is $R_4$. In certain embodiments $R_2$ is hydrogen, alkyl or alkoxyalkylenyl. In certain embodiments $R_2$ is hydrogen, $C_{1-4}$ alkyl, or $C_{1-4}$ alkyl-O—$C_{1-4}$ alkylenyl. In certain embodiments $R_2$ is methyl, ethyl, n-propyl, n-butyl, 2-methoxyethyl, methoxymethyl, or ethoxymethyl.

For certain embodiments, R is selected from the group consisting of hydrogen, alkyl, alkoxy, trifluoromethyl, chloro, fluoro, and hydroxy.

For certain embodiments, R is hydrogen.

For certain embodiments, $R_a$ is selected from the group consisting of alkoxy, alkylenedioxy, hydroxy, nitro, oxo, thioxo, —$R_4$, —Y—$R_4$, —X—Y—$R_4$, =N-Q-$R_4$, =N—CN, and =N—OH.

For certain embodiments, $R_a$ is hydroxy, alkoxy, oxo, or $R_4$.

For certain embodiments, $R_{3a}$ is $C_{2-7}$ alkylene.

For certain embodiments, $R_{3a}$ is $C_{2-5}$ alkylene.

For certain embodiments, $R_{3b}$ is $C_{1-5}$ alkylene wherein both $R_{3b}$ groups combined have a total of up to seven carbon atoms. For certain embodiments, both $R_{3b}$ groups combined have a total of up to five carbon atoms.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, heterocyclyl, and heterocyclylalkylenyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, heterocyclyl, and heterocyclylalkylenyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo.

For certain embodiments, $R_4$ is selected from the group consisting of alkyl, aryl, and heteroaryl.

For certain embodiments, $R_4$ is alkyl or aryl.

For certain embodiments, $R_5$ is selected from the group consisting of:

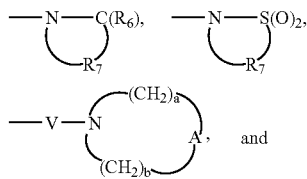

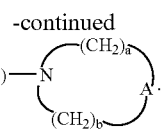

For certain embodiments, $R_5$ is selected from the group consisting of:

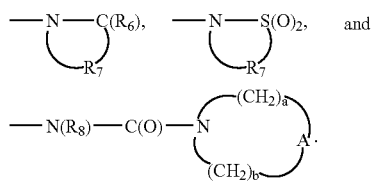

In certain embodiments, $R_5$ is

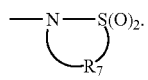

In certain embodiments, $R_5$ is selected from the group consisting of:

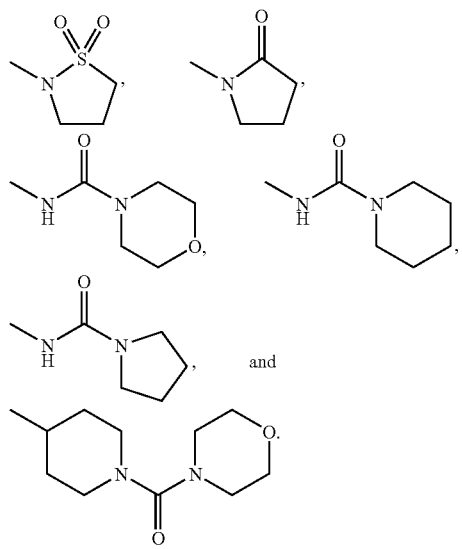

For certain embodiments, $R_6$ is selected from the group consisting of =O and =S.

For certain embodiments, $R_6$ is =O.

For certain embodiments, $R_7$ is $C_{2-7}$ alkylene.

For certain embodiments, $R_7$ is $C_{2-3}$ alkylene.

For certain embodiments, $R_8$ is selected from the group consisting of hydrogen, alkyl, alkoxyalkylenyl, and arylalkylenyl.

For certain embodiments, particularly in —N($R_8$)-Q- and —C($R_6$)—N($R_8$)—, $R_8$ is selected from the group consisting of hydrogen, $C_{1-4}$ alkyl, and alkoxyalkylenyl.

For certain embodiments, $R_8$ is hydrogen or $C_{1-4}$ alkyl.

For certain embodiments, $R_9$ is selected from the group consisting of hydrogen and alkyl.

For certain embodiments, $R_9$ is hydrogen or methyl.

For certain embodiments, $R_{10}$ is $C_{3-8}$ alkylene.

For certain embodiments, $R_{10}$ is $C_5$ alkylene.

For certain embodiments, A is selected from the group consisting of —O—, —C(O)—, —S(O)$_{0-2}$—, —CH$_2$—, and —N($R_4$)—.

For certain embodiments, A is —O—, —CH$_2$—, or —C(O)—.

For certain embodiments, A' is selected from the group consisting of —O—, —C(O)—, —CH$_2$—, —S(O)$_{0-2}$—, —N(Q-$R_4$)—, and —C(O)—N(Q-$R_4$)—.

For certain embodiments, A' is —O—.

For certain embodiments, Q is selected from the group consisting of a bond, —C($R_6$)—, —C($R_6$)—C($R_6$), —S(O)$_2$—, —C($R_6$)—N($R_8$)—W—, —S(O)$_2$—N($R_8$)—, —C($R_6$)—O—, and —C($R_6$)—N(O$R_9$)—.

For certain embodiments, Q is —C(O)—, —S(O)$_2$—, or —C(O)—N($R_8$)—.

For certain embodiments, V is selected from the group consisting of —C($R_6$)—, —O—C($R_6$)—, —N($R_8$)—C($R_6$)—, and —S(O)$_2$—.

For certain embodiments, V is —C(O)—.

For certain embodiments, V is —N($R_8$)—C(O)—.

For certain embodiments, W is selected from the group consisting of a bond, —C(O)—, and —S(O)$_2$—.

For certain embodiments, W is a bond.

For certain embodiments, X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups.

For certain embodiments, X is alkylene.

For certain embodiments, X is $C_{2-6}$ alkylene.

For certain embodiments, Y is selected from the group consisting of —O—, —S(O)$_{0-2}$—, —S(O)$_2$—N($R_8$)—, —C($R_6$)—, —C($R_6$)—O—, —O—C($R_6$)—, —O—C(O)—O—, —O—S(O)$_2$—, —N($R_8$)-Q-, —C($R_6$)—N($R_8$)—, —O—C($R_6$)—N($R_8$)—, —C($R_6$)—N(O$R_9$)—,

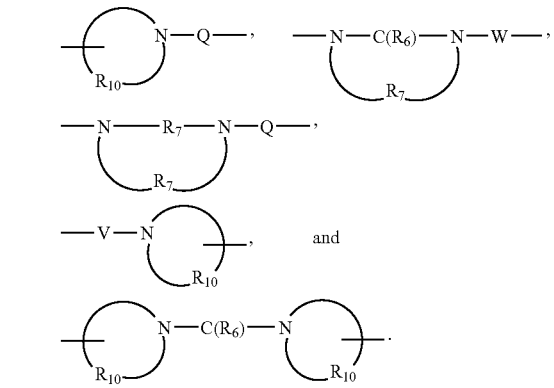

For certain embodiments, Y is selected from the group consisting of —S(O)$_{0-2}$—, —S(O)$_2$—N($R_8$)—, —C($R_6$)—, —C($R_6$)—O—, —O—C($R_6$)—, —O—C(O)—O—, —O—S(O)$_2$—, —N($R_8$)-Q-, —C($R_6$)—N($R_8$)—, —O—C($R_6$)—N($R_8$)—, —C($R_6$)—N(O$R_9$)—,

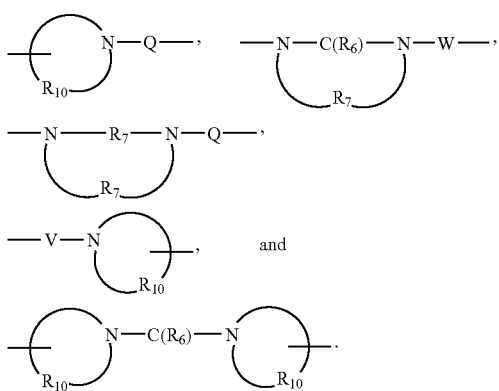

For certain embodiments, Y is selected from the group consisting of —S(O)$_{0-2}$—, —N(R$_8$)-Q-, and

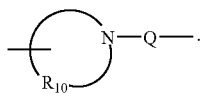

For certain embodiments, Y is —S(O)O$_{0-2}$— or —NR$_8$-Q-.

For certain embodiments, Y is —N(R$_8$)—C(O)—, —N(R$_8$)—S(O)$_2$—, or —N(R$_8$)—C(O)—N(R$_8$)—.

For certain embodiments, Z is selected from the group consisting of —C(O)—, —C(S)—, —S(O)$_{0-2}$—, —OC(O)—, —N(Q-R$_4$)—C(O)—, —N(Q-R$_4$)—C(S)—, and —N(Q-R$_4$)—S(O)$_2$—

For certain embodiments, Z is —C(O)—, —S(O)$_{0-2}$—, —OC(O)—, or —N(Q-R$_4$)—C(O)—.

For certain embodiments, a and b are independently integers from 1 to 6 with the proviso that a+b is ≦7.

For certain embodiments, a is 2.

For certain embodiments, b is 2.

For certain embodiments, n is 0 or 1. For certain embodiments, n is 0. For certain embodiments, n is 1.

For certain embodiments of the compounds of Formulas I, II, IIa, and III, the —NH$_2$ group can be replaced by an —NH-G group, as shown in the compound of Formula IV, to form prodrugs. In such embodiments, G is selected from the group consisting of —C(O)—R''', α-aminoacyl, α-aminoacyl-α-aminoacyl, —C(O)—O—R''', —C(O)—N(R'''')R''', —C(=NY')—R''', —CH(OH)—C(O)—OY', —CH(OC$_{1-4}$ alkyl)Y$_0$, —CH$_2$Y$_1$, and —CH(CH$_3$)Y$_1$. In some embodiments G is selected from the group consisting of —C(O)—R''', α-aminoacyl, α-aminoacyl-α-aminoacyl, and —C(O)—O—R'''. Preferably, R''' and R'''' are independently selected from the group consisting of C$_{1-10}$ alkyl, C$_{3-7}$ cycloalkyl, and benzyl, each of which may be unsubstituted or substituted by one or more substitutents selected from the group consisting of halogen, hydroxy, nitro, cyano, carboxy, C$_{1-6}$ alkyl, C$_{1-4}$ alkoxy, aryl, heteroaryl, arylC$_{1-4}$ alkylenyl, heteroarylC$_{1-4}$ alkylenyl, haloC$_{1-4}$ alkylenyl, haloC$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$. R'''' may also be hydrogen. Preferably, α-aminoacyl is an acyl group derived from an amino acid selected from the group consisting of racemic, D-, and L-amino acids. Preferably, Y' is selected from the group consisting of hydrogen, C$_{1-6}$ alkyl, and benzyl. Preferably, Y$_0$ is selected from the group consisting of C$_{1-6}$ alkyl, carboxyC$_{1-6}$ alkylenyl, aminoC$_{1-4}$ alkylenyl, mono-N-C$_{1-6}$ alkylaminoC$_{1-4}$ alkylenyl, and di-N,N-C$_{1-6}$ alkylaminoC$_{1-4}$ alkylenyl. Preferably, Y, is selected from the group consisting of mono-N-C$_{1-6}$ alkylamino, di-N,N-C$_{1-6}$ alkylamino, morpholin-4-yl, piperidin-1-yl, pyrrolidin-1-yl, and 4-C$_{1-4}$ alkylpiperazin-1-yl.

For certain embodiments, including any one of the above embodiments containing —NH-G, G is —C(O)—R''', α-aminoacyl, α-aminoacyl-α-aminoacyl, or —C(O)—O—R'''.

Herein, "non-interfering" means that the ability of the compound or salt, which includes a non-interfering substituent, to modulate the biosynthesis of one or more cytokines is not destroyed by the non-interfering substitutent. Illustrative non-interfering R' groups include those described above for R$_1$ in Formulas IIa-IV. Illustrative non-interfering R" groups include those described above for R$_2$ in Formulas IIa-IV.

As used herein, the terms "alkyl", "alkenyl", "alkynyl", and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene", "alkenylene", and "alkynylene" are the divalent forms of the "alkyl", "alkenyl", and "alkynyl" groups defined above. The terms, "alkylenyl", "alkenylenyl", and "alkynylenyl" are use when "alkylene", "alkenylene", and "alkynylene", respectively, are substituted. For example, an arylalkylenyl group comprises an alkylene moiety to which an aryl group is attached. In another example, hydroxyalkylenyl, haloalkylenyl, and haloalkyleneoxy have the same meaning as hydroxyalkyl, haloalkyl, and haloalkoxy, respectively.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2 to 12 carbon atoms, 1 to 3 rings, 1 to 4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(21)-yl, dihydro-1H-imidazolyl, 3-azabicyclo[3.2.2]non-3-yl, and the like.

The term "heterocyclyl" includes bicyclic and tricyclic heterocyclic ring systems. Such ring systems include fused and/or bridged rings and Spiro rings. Fused rings can include, in addition to a saturated or partially saturated ring, an aromatic ring, for example, a benzene ring. Spiro rings include two rings joined by one spiro atom and three rings joined by two Spiro atoms.

When "heterocyclyl" contains a nitrogen atom, the point of attachment of the heterocyclyl group may be the nitrogen atom.

Bicyclic and tricyclic rings of the heterocyclic ring system, include fused and/or bridged rings and spiro rings. Fused rings can include, in addition to a saturated or partially saturated ring, an aromatic ring, for example, a benzene ring. Spiro rings include two rings joined by one spiro atom and three rings joined by two Spiro atoms.

Illustrative heterocyclic ring systems, include, for example, the following:

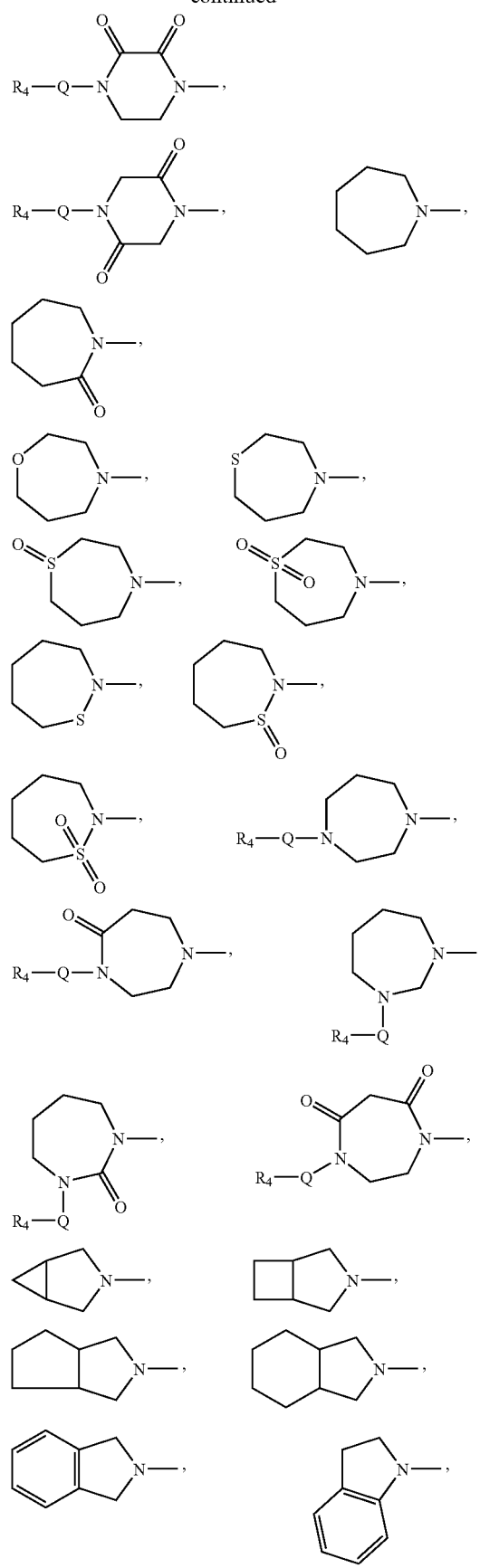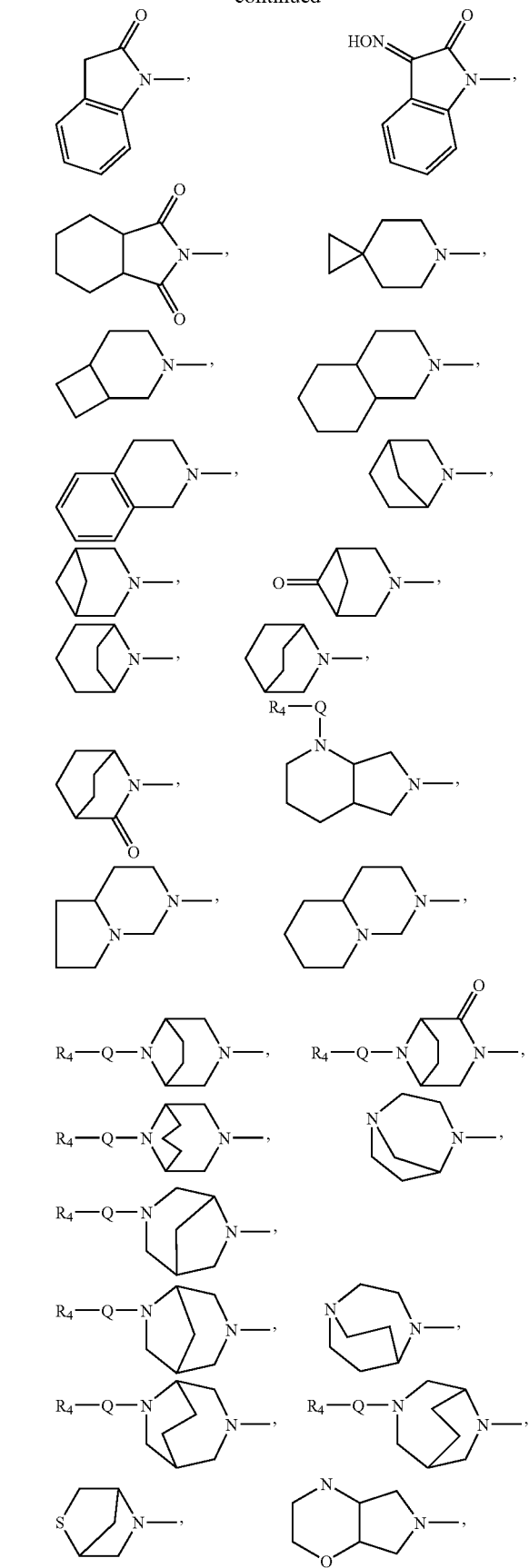

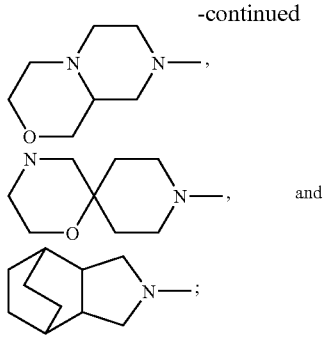

wherein $R_4$, and Q are as defined above. In some examples Q is a bond, and in some examples Q is a bond and $R_4$ is hydrogen or alkyl.

The terms "arylene", "heteroarylene", and "heterocyclylene" are the divalent forms of the "aryl", "heteroaryl", and "heterocyclyl" groups defined above. The terms, "arylenyl", "heteroarylenyl", and "heterocyclylenyl" are used when "arylene", "heteroarylene," and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula

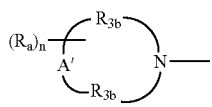

each $R_{3b}$ group is independently selected. In another example, when an $R_1$ and an $R_2$ group both contain an $R_4$ group, each $R_4$ group is independently selected. In a further example, when more than one Y group is present and each Y group contains one or more $R_7$ groups, then each Y group is independently selected, and each $R_7$ group is independently selected.

The invention is inclusive of the compounds described herein (including intermediates) in any of their pharmaceutically acceptable forms, including isomers (e.g., diastereomers and enantiomers), salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term "prodrug" means a compound that can be transformed in vivo to yield an immune response modifying compound in any of the salt, solvated, polymorphic, or isomeric forms described above. The prodrug, itself, may be an immune response modifying compound in any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

Preparation of the Compounds

Compounds of the invention can be prepared according to Reaction Scheme I wherein R, $R_1$, and $R_2$ are as defined above, and is

defined above containing a carbonyl, thiocarbonyl, or sulfonyl group adjacent the nitrogen atom. In step (1) of Reaction Scheme I, a 4-chloro-3-nitroquinoline of Formula X is reacted with an amine of Formula $R_1$—$NH_2$ to provide a compound of Formula XI. The reaction can be carried out by adding the amine to a solution of a compound of Formula X in a suitable solvent such as anhydrous dichloromethane in the presence of a base such as triethylamine. The reaction can be run at ambient temperature. Compounds of Formula X can be prepared using the synthetic methods described at the beginning of the Example section below.

In step (2) of Reaction Scheme I a compound of Formula XI is reduced to provide a compound of Formula XII. The reduction can be carried out using a conventional heterogeneous hydrogenation catalyst such as platinum on carbon. The reaction can be conveniently carried out on a Parr apparatus in a suitable solvent such as acetonitrile, toluene and/or isopropanol.

Other reduction processes may be used for the reduction in step (2). For example, an aqueous solution of sodium dithionite can be added to a solution or suspension of the compound of Formula XI in a suitable solvent such as ethanol or isopropanol. The reaction can be carried out at an elevated temperature, for example at reflux, or at ambient temperature.

In step (3) of Reaction Scheme I a compound of Formula XII is (i) reacted with an acyl halide of Formula $R_2C(O)Cl$ or $R_2C(O)Br$ and then (ii) cyclized to provide a 1H-imidazo compound of Formula XIII. In part (i) the acyl halide is added to a solution of a compound of Formula XII in a suitable solvent such as acetonitrile or anhydrous dichloromethane in the presence of a base such as triethylamine. The reaction can be run at a reduced temperature, for example, 0° C., or at ambient temperature. In part (ii) the product of part (i) is heated in an alcoholic solvent in the presence of a base. For example, the product of part (i) is refluxed in ethanol in the presence of excess triethylamine or is heated with methanolic ammonia.

Alternatively, step (3) can be carried out by reacting a compound of Formula XII with a carboxylic acid or an equivalent thereof. Suitable equivalents to carboxylic acid include orthoesters and 1,1-dialkoxyalkyl alkanoates. The carboxylic acid or equivalent is selected such that it will provide the desired $R_2$ substituent in a compound of Formula XIII. For example, triethyl orthoformate will provide a compound where $R_2$ is hydrogen, and triethyl orthovalerate will provide a compound where $R_2$ is butyl. The reaction can be run in the absence of solvent or in an inert solvent such as anhydrous toluene. The reaction is run with sufficient heating to drive off any alcohol or water formed as a byproduct of the reaction. Optionally a catalyst such as pyridine hydrochloride can be utilized.

In step (4a) of Reaction Scheme I, a 1H-imidazo compound of Formula XIII is oxidized to provide an N-oxide of Formula XIV using a conventional oxidizing agent that is capable of forming N-oxides. The reaction is carried out by treating a solution of a compound of Formula XIII in a suitable solvent such as chloroform or dichloromethane with 3-chloroperoxybenzoic acid at ambient temperature.

In step (4b) of Reaction Scheme I, an N-oxide of Formula XIV is aminated to provide a 1H-imidazo[4,5-c]quinolin-4-amine of the Formula XV. The reaction is carried out in two parts. In part (i) a compound of Formula XV is reacted with an acylating agent. Suitable acylating agents include alkyl- or arylsulfonyl chlorides (e.g., benzenesulfonyl chloride, methanesulfonyl chloride, and p-toluenesulfonyl chloride). In part (ii) the product of part (i) is reacted with an excess of an aminating agent. Suitable aminating agents include ammonia (e.g. in the form of ammonium hydroxide) and ammonium salts (e.g., ammonium carbonate, ammonium bicarbonate, ammonium phosphate). The reaction can be carried out by dissolving a compound of Formula XIV in a suitable solvent such as dichloromethane, adding ammonium hydroxide to the solution, and then adding p-toluenesulfonyl chloride.

Alternatively, in step (4) the oxidation of step (4a) and the amination of step (4b) can be carried out sequentially without isolating the product of the oxidation to provide a 1H-imidazo [4,5-c]quinolin-4-amine of the Formula XV. In step (4), after the 1H-imidazo compound of Formula XIII is consumed by reaction with 3-chloroperoxybenzoic acid as described in step (4a), the aminating and acylating agents are added to the reaction mixture as in step (4b).

In step (5) of Reaction Scheme I, a 1H-imidazo[4,5-c] quinolin-4-amine of the Formula XV is subjected to a copper-catalyzed amination with a nitrogen-containing heterocyclyl compound of the Formula

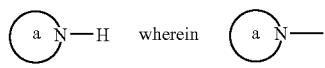

is defined above, to provide a 1H-imidazo[4,5-c]quinolin-4-amine of Formula IIc. Many of these nitrogen-containing heterocyclyl compounds are commercially available; others can be prepared by known methods. The reaction is carried out by combining the 1H-imidazo[4,5-c]quinolin-4-amine of the Formula XV and the nitrogen-containing heterocyclyl compound in the presence of copper (I) iodide, potassium phosphate, and racemic trans-1,2-diaminocyclohexane in a suitable solvent such as 1,4-dioxane. The reaction can be carried out at an elevated temperature such as 110° C. The compound or pharmaceutically acceptable salt thereof can be isolated using conventional methods.

Many compounds of the Formula XV are known and can be used in Reaction Scheme I at step (5). See, for example, U.S. Pat. Nos. 4,689,338; 4,929,624; 5,268,376; 5,346,905; 5,389,640; 5,756,747; 6,331,539; 6,451,810; 6,541,485; 6,677,349; 6,660,747; 6,670,372; 6,683,088; 6,656,938; 6,664,264; 6,664,260; European Patent Application 1 104 764; and Japanese Patent Application 9-255926. Others can be readily prepared using known synthetic methods. See, for example, U.S. Pat. Nos. 4,988,815; 5,175,296; 5,367,076; 5,395,937; and 5,741,908.

Compounds of the invention can be also prepared according to Reaction Scheme II wherein R, $R_1$, $R_2$, and

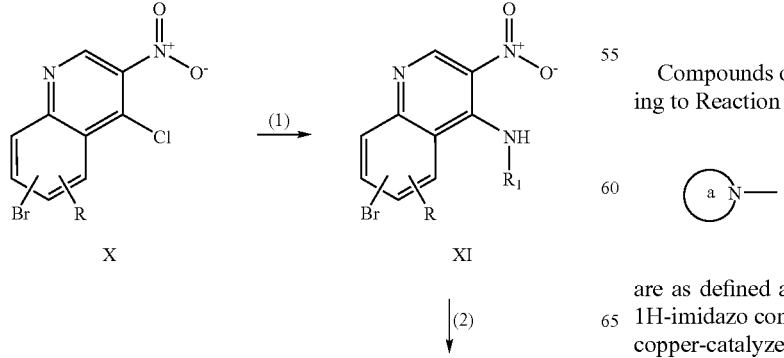

are as defined above. In step (1) of Reaction Scheme II, a 1H-imidazo compound of the Formula XIII is subjected to a copper-catalyzed amination with a nitrogen-containing heterocyclyl compound of the Formula

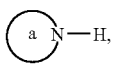

as described in step (5) of Reaction Scheme I, to provide a 1H-imidazo compound of Formula XVIa In step (2) of Reaction Scheme II, a 1H-imidazo compound of Formula XVIa is oxidized to provide an N-oxide which is aminated to provide a 1H-imidazo[4,5-c]quinolin-4-amine of Formula IIc. The reaction is carried out as in steps (4a) and (4b) or step (4) of Reaction Scheme I. The product or a pharmaceutically acceptable salt thereof can be isolated by conventional methods.

In step (2) of Reaction Scheme III, a 1H-imidazo compound of Formula XVI is oxidized to provide a 5N-oxide of Formula XVII. The reaction is carried out by combining the 1H-imidazo compound of Formula XVI with benzonitrile and sodium bicarbonate in a suitable solvent such as methanol, and then slowly adding hydrogen peroxide (55% by weight in water). The reaction can be carried out at room temperature.

In step (3) of Reaction Scheme III, a 5N-oxide of Formula XVII is aminated to provide a 1H-imidazo[4,5-c]quinolin-4-amine of the Formula IIa. The reaction can be carried out as in step (4b) of Reaction Scheme I. The product or a pharmaceutically acceptable salt thereof can be isolated by conventional methods.

Reaction Scheme II

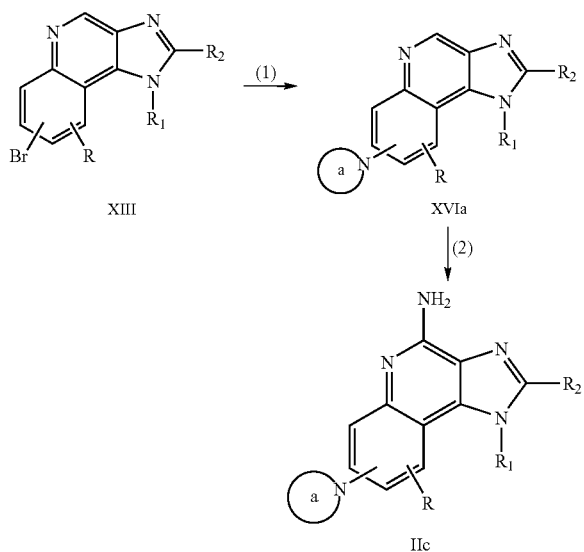

Reaction Scheme III

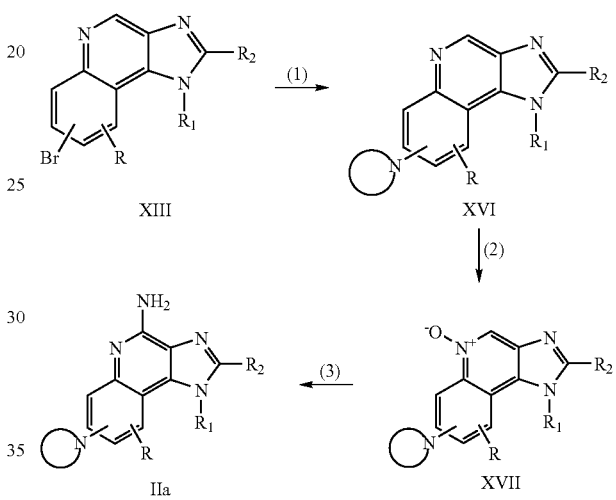

Compounds of the invention can be also prepared according to Reaction Scheme III wherein R, $R_1$, $R_2$, and

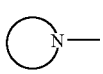

are as defined above. In step (1) of Reaction Scheme III, a 1H-imidazo compound of the Formula XIII is subjected to a palladium-catalyzed amination with a nitrogen-containing heterocyclyl compound of the Formula

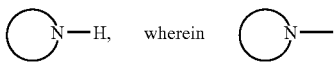

is as described above, to provide a 1H-imidazo compound of Formula XVI. Many of these nitrogen-containing heterocyclyl compounds are commercially available; others can be prepared by known methods. The reaction is carried out by combining the 1H-imidazo compound of the Formula XIII and the nitrogen-containing heterocyclyl compound in the presence of tris(dibenzylideneacetone)dipalladium, (±)-2,2'-bis(diphenylphosphino)-1,1'-binaphthyl, sodium tert-butoxide, and a suitable solvent such as toluene. The reaction can be carried out at an elevated temperature such as 80° C.

Compounds of the invention can be also prepared according to Reaction Scheme IV wherein R, $R_1$, $R_2$, and

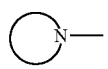

are as defined above and E is a carbon atom or a nitrogen atom. Scheme IV begins with a bromo aniline or bromo aminopyridine of Formula XVIII, many of which are commercially available or can be prepared using conventional synthetic methods. In step (1) of Reaction Scheme IV, a bromo aniline or bromo aminopyridine of Formula XVIII is treated with the condensation product generated from 2,2-dimethyl-1,3-dioxane-4,6-dione (Meldrum's acid) and triethyl orthoformate to provide an imine of Formula XIX. The reaction is conveniently carried out by adding a bromo aniline or bromo aminopyridine of Formula XVIII to a heated mixture of Meldrum's acid and triethyl orthoformate and heating the reaction at an elevated temperature such as 55° C.

In step (2) of Reaction Scheme IV, an imine of Formula XIX undergoes thermolysis and cyclization to provide a compound of Formula XX. The reaction is carried out in a medium such as DOWTHERM A heat transfer fluid at a temperature between 200 and 250° C.

In step (3) of Reaction Scheme IV, a compound of Formula XX is nitrated under conventional nitration conditions to provide a compound of Formula XXI. The reaction is carried out by combining a compound of Formula XX with fuming nitric acid and heating the mixture at an elevated temperature such as 90° C.

In step (4) of Reaction Scheme IV, a compound of Formula XXI is chlorinated using conventional methods to provide a compound of Formula XXII. The reaction is carried out by adding phosphorous oxychloride to a suspension of a compound of Formula XXI in a suitable solvent such as N,N-dimethylformamide. The reaction can be carried out at ambient temperature.

A compound of Formula XII is converted to a 1H-imidazo[4,5-c]quinoline or 1H-imidazo[4,5-c][1,5]naphthyridine of Formula XXIII using the methods of steps (1) through (3) of Reaction Scheme I.

A 1H-imidazo[4,5-c]quinoline or 1H-imidazo[4,5-c][1,5]naphthyridine of Formula XXIII can be converted to a 1H-imidazo[4,5-c]quinolin-4-amine or 1H-imidazo[4,5-c][1,5]naphthyridin-4-amine of Formula XXIV using the methods described in Reaction Schemes I, II, and III.

Compounds shown in Reaction Scheme I can be further elaborated using conventional synthetic methods. For example, an amine of Formula $R_1$—$NH_2$ may be substituted by a hydroxy or second amino group, which may be further functionalized before step (2) of Reaction Scheme I. For example, a 3-nitroquinolin-4-amine of Formula XI, in which $R_1$ is has an amino substituent, can be reacted with an acid chloride of Formula $R_{4b}C(O)Cl$, a sulfonyl chloride of Formula $R_{4b}S(O)_2Cl$, or a sulfonic anhydride of Formula $(R_{4b}S(O)_2)_2O$ to provide a compound of Formula XI in which $R_1$ is —X—Y—$R_{4b}$, where Y is —$N(R_5)$-Q-, $R_5$ is as defined above, Q is —C(O)— or —$SO_2$—, and $R_{4b}$ is a subset of $R_4$ that does not include those substituents which one skilled in the art would recognize as being susceptible to oxidation in step (4a). Numerous acid chlorides, sulfonyl chlorides, and sulfonic anhydrides are commercially available; others can be readily prepared using known synthetic methods. The reaction can be conveniently carried out by adding an acid chloride of Formula $R_{4b}C(O)Cl$, a sulfonyl chloride of Formula

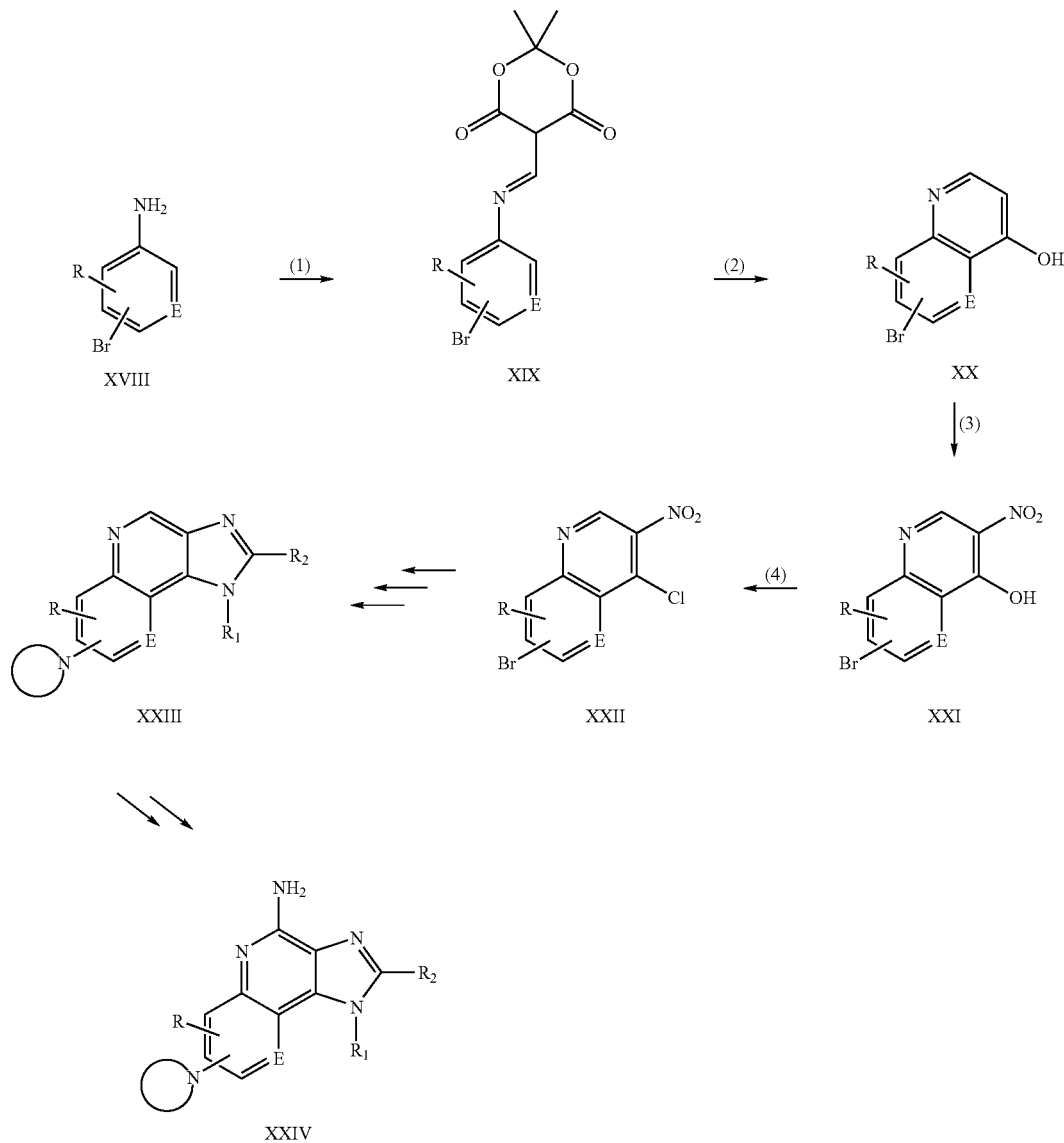

Reaction Scheme IV $R_{4b}S(O)_2Cl$, or a sulfonic anhydride of Formula $(R_{4b}S(O)_2)_2$ O to a solution of a 3-nitroquinolin-4-amine of Formula XI, in which $R_1$ has an amino substituent, and a base such as triethylamine in a suitable solvent such as dichloromethane. The reaction can be carried out at ambient temperature.

A 3-nitroquinolin-4-amine of Formula XI, in which $R_1$ is has an amino substituent, can also react with isocyanates of Formula $R_{4b}N=C=O$ to provide a compound of Formula XI in which $R_1$ is —X—Y—$R_{4b}$, where Y is —N($R_8$)-Q-, $R_8$ is as defined above, and Q is —C($R_6$)—N($R_8$)—W—, $R_6$ is =O, and W is a bond. Numerous isocyanates of Formula $R_{4b}N=C=O$ are commercially available; others can be readily prepared using known synthetic methods. The reaction can be conveniently carried out by adding the isocyanate of Formula $R_{4b}N=C=O$ to a solution of the 3-nitroquinolin-4-amine of Formula XI, in which $R_1$ has an amino substituent, in a suitable solvent such as dichloromethane. The reaction can be carried out at ambient temperature. Alternatively, a compound of Formula XI, in which $R_1$ has an amino substituent, can be treated with an isocyanate of Formula $R_{4b}(CO)N=C=O$, a thioisocyanate of Formula $R_{4b}N=C=S$, a sulfonyl isocyanate of Formula $R_{4b}S(O)_2N=C=O$, or a carbamoyl chloride of Formula $R_{4b}N—(R_8)—C(O)Cl$ or

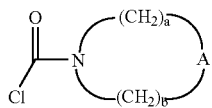

to provide a compound of Formula XI, where $R_1$ is —X—N($R_8$)-Q-$R_{4b}$ or

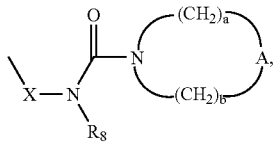

Q is —C($R_6$)—N($R_8$)—W—, and $R_6$, $R_8$, and W are as defined above. The product can then be treated according to steps (2) through (5) of Reaction Scheme I to provide 1H-imidazo[4,5-c]quinolin-4-amine of Formula IIc.

Several examples of synthetic elaborations of an $R_1$ group are known. See, for example, U.S. Pat. No. 4,689,338 (Gerster), U.S. Pat. No. 4,929,624 (Gerster et al.), U.S. Pat. No. 5,268,376 (Gerster), U.S. Pat. No. 5,389,640 (Gerster et al.), U.S. Pat. No. 6,331,539 (Crooks et al.), U.S. Pat. No. 6,451,810 (Coleman et al.), U.S. Pat. No. 6,541,485 (Crooks et al.), U.S. Pat. No. 6,660,747 (Crooks et al.), U.S. Pat. No. 6,670,372 (Charles et al.), U.S. Pat. No. 6,683,088 (Crooks et al.), U.S. Pat. No. 6,656,938 (Crooks et al.), U.S. Pat. No. 6,664,264 (Dellaria et al.), and PCT Publication No. WO 03/103584.

Similar synthetic transformations can be made at $R_2$ if, for example, the acid chloride used in step (3) of Reaction Scheme I contains a protected hydroxy or amino group. Several acid chlorides of this type, for example acetoxyacetyl chloride, are commercially available. Others can be prepared by known synthetic methods. For examples of synthetic elaborations of an $R_2$ group, see U.S. Pat. No. 5,389,640 (Gerster et al.).

Compounds of the invention can also be prepared using the synthetic routes described in the EXAMPLES below.

Prodrugs can be prepared in a variety of ways. For example, a compound wherein $R_2$ (or $R_1$) is —X—OH (e.g. hydroxyalkylenyl) can be converted into a prodrug wherein $R_2$ (or $R_1$) is, for example, —X—O—C($R_6$)—$R_4$, —X—O—C($R_6$)—O—$R_4$, or —X—O—C($R_6$)—N($R_8$)—$R_4$, wherein X, $R_4$, $R_6$, and $R_8$ are as defined above, using methods known to one skilled in the art. For any of these compounds containing an alcohol functional group, a prodrug can be formed by the replacement of the hydrogen atom of the alcohol group with a group such as $C_{1-6}$ alkanoyloxymethyl, 1-($C_{1-6}$ alkanoyloxy)ethyl, 1-methyl-1-($C_{1-6}$ alkanoyloxy)ethyl, $C_{1-6}$ alkoxycarbonyloxymethyl, N-($C_{1-6}$ alkoxycarbonyl)aminomethyl, succinoyl, $C_{1-6}$ alkanoyl, α-amino$C_{1-4}$ alkanoyl, arylacyl, —P(O)(OH)$_2$, —P(O)(O—$C_{1-6}$ alkyl)$_2$, $C_{1-6}$ alkoxycarbonyl, $C_{1-6}$ alkylcarbamoyl, and α-aminoacyl or α-aminoacyl-α-aminoacyl, where each α-aminoacyl group is independently selected from racemic, D-, and L-amino acids. For compounds containing an alcohol functional group, particularly useful prodrugs are esters made from carboxylic acids containing one to six carbon atoms, unsubstituted or substituted benzoic acid esters, or esters made from racemic, D- or L-amino acids.

Prodrugs can also be made from a compound containing an amino group by conversion of the amino group to a functional group such as an amide, carbamate, urea, amidine, or another hydrolizable group using conventional methods. A prodrug of this type can be made by the replacement of a hydrogen atom in an amino group, particularly the amino group at the 4-position, with a group such as —C(O)—R''', α-aminoacyl, α-aminoacyl-α-aminoacyl, —C(O)—O—R''', —C(O)—N(R'''')—R''', —C(=NY')—R''', —CH(OH)—C(O)—OY', —CH(OC$_{1-4}$ alkyl)Y$_0$, —CH$_2$Y$_1$, or —CH(CH$_3$)Y$_1$; wherein R''' and R'''' are each independently $C_{1-10}$ alkyl, $C_{3-7}$ cycloalkyl, or benzyl, each of which may be unsubstituted or substituted by one or more substituents selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, halo$C_{1-4}$ alkyl, halo$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$; each α-aminoacyl group is independently selected from racemic, D-, and L-amino acids; Y' is hydrogen, $C_{1-6}$ alkyl, or benzyl; Y$_0$ is $C_{1-6}$ alkyl, carboxy$C_{1-6}$ alkylenyl, amino$C_{1-4}$ alkylenyl, mono-N-$C_{1-6}$ alkylamino$C_{1-4}$ alkylenyl, or di-N,N-$C_{1-6}$ alkylamino$C_{1-4}$ alkylenyl; and Y$_1$ is mono-N-$C_{1-6}$ alkylamino, di-N,N-$C_{1-6}$ alkylamino, morpholin-4-yl, piperidin-1-yl, pyrrolidin-1-yl, or 4-$C_{1-4}$ alkylpiperazin-1-yl; with the proviso that R'''' can also be hydrogen.

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Although the exact amount of active compound or salt used in a pharmaceutical composition of the invention will vary according to factors known to those of skill in the art, such as the physical and chemical nature of the compound or salt, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (µg/kg) to about 5 mg/kg, of the compound or salt to the subject. A variety of dosage forms may be used, such as tablets, lozenges, capsules, parenteral formulations, syrups, creams, ointments, aerosol formulations, transdermal patches, transmucosal patches and the like.

The compounds or salts of the invention can be administered as the single therapeutic agent in the treatment regimen, or the compounds or salts of the invention may be administered in combination with one another or with other active agents, including additional immune response modifiers, antivirals, antibiotics, antibodies, proteins, peptides, oligonucleotides, etc.

Compounds or salts of the invention have been shown to induce, and certain compounds or salts of the invention may inhibit, the production of certain cytokines in experiments performed according to the tests set forth below. These results indicate that the compounds or salts are useful as immune response modifiers that can modulate the immune response in a number of different ways, rendering them useful in the treatment of a variety of disorders.

Cytokines whose production may be induced by the administration of compounds or salts of the invention generally include interferon-α (IFN-α) and/or tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt or composition of the invention to the animal. The animal to which the compound or salt or composition is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Other cytokines whose production may be inhibited by the administration of compounds or salts of the invention include tumor necrosis factor-α (TNF-α). Among other effects, inhibition of TNF-α production can provide prophylaxis or therapeutic treatment of TNF-α mediated diseases in animals, making the compounds or salt useful in the treatment of, for example, autoimmune diseases. Accordingly, the invention provides a method of inhibiting TNF-α biosynthesis in an animal comprising administering an effective amount of a compound or salt or composition of the invention to the animal. The animal to which the compound or salt or composition is administered for inhibition of TNF-α biosynthesis may have a disease as described infra, for example an autoimmune disease, and administration of the compound or salt may provide therapeutic treatment. Alternatively, the compound or salt may be administered to the animal prior to the animal acquiring the disease so that administration of the compound or salt may provide a prophylactic treatment.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which compounds or salts identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella*;

(c) other infectious diseases, such chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, a compound or salt of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influenza* b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts of the present invention may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An amount of a compound or salt effective to induce or inhibit cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) or decreased (inhibited) over a background level of such cytokines. The precise amount will vary according to factors known in the art but is expected to be a dose of about 100 ng/kg to about 50 mg/kg, preferably about 10 µg/kg to about 5 mg/kg. The invention also provides a method of treating a viral infection in an animal and a method of treating a neoplastic disease in an animal comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

EXAMPLES

Objects and advantages of this invention are further illustrated by the following examples, but the particular materials and amounts thereof recited in these examples, as well as other conditions and details, should not be construed to unduly limit this invention.

Preparation of 7-Bromo-4-chloro-3-nitroquinoline

Part A

A mixture of triethyl orthoformate (154 grams (g), 1.04 moles (mol) and Meldrum's acid (142 g, 0.983 mol) was heated to 55° C. for 4 hours (h). After cooling to 50° C., a solution of 3-bromoaniline (162.6 g, 0.945 mol) in ethanol (300 mL) was added such that the temperature of the reaction was maintained between 50-55° C. After half of the 3-bromoaniline had been added, stirring became difficult due to the formation of solids, so more ethanol (1 liter (L)) was added to facilitate stirring. Upon complete addition, the reaction was cooled to room temperature (RT), and the solids were collected by filtration. The filter cake washed with ice cold ethanol until the washings were nearly colorless, and the product was dried at 65° C. under vacuum to afford 287 g of 5-[(3-bromophenylamino)methylene]-2,2-dimethyl-[1,3]dioxane-4,6-dione as an off-white solid.

$^1$H NMR (300 MHz, CDCl$_3$) δ 11.19 (brd, J=12.8 Hz, 1H), 8.60 (d, J=14.0 Hz, 1H), 7.44-7.38 (m, 2H), 7.30 (t, J=8.0 Hz, 1H), 7.18 (ddd, J=8.0, 2.2, 0.9 Hz, 1H), 1.75 (s, 6H).

Part B

7-Bromoquinolin-4-ol was prepared in accordance with the literature procedure (D. Dibyendu et al., *J. Med. Chem.*, 41, 4918-4926 (1998)) or by thermolysis of 5-[(3-bromophenylamino)methylene]-2,2-dimethyl-[1,3]dioxane-4,6-dione in DOWTHERM A heat transfer fluid and had the following spectral properties:

$^1$H NMR (300 MHz, d$_6$-DMSO) δ 11.70 (brs, 1H), 8.00 (d, J=8.7 Hz, 1H), 7.92 (d, J=7.5 Hz, 1H), 7.74 (d, J=1.9 Hz, 1H), 7.44 (dd, J=8.7, 1.9 Hz, 1H), 6.05 (d, J=7.5 Hz, 1H).

Part C

A stirred suspension of 7-bromoquinolin-4-ol (162 g, 0.723 mol) in propionic acid (1500 mL) was brought to 110° C. 70% Nitric acid (85 g) was added dropwise over 1 h such that the temperature was maintained between 110-115° C. After half of the nitric acid had been added, stirring became difficult due to the formation of solids and an additional 200 mL of propionic acid was added. Upon complete addition, the reaction was stirred for 1 h at 110° C., cooled to room temperature, and the solid was collected by filtration. The filter cake washed with ice cold ethanol until the washings were nearly colorless (800 mL), and the product was dried at 60° C. under vacuum to afford 152 g of 7-bromo-3-nitro-quinolin-4-ol as a pale yellow solid.

$^1$H NMR (300 MHz, d$_6$-DMSO) δ 13.0 (brs, 1H), 9.22 (s, 1H), 8.15 (d, J=8.4 Hz, 1H), 7.90 (d, J=1.6 Hz, 1H), 7.66 (dd, J=8.7, 1.9 Hz, 1H).

Part D

7-Bromo-3-nitroquinolin-4-ol (42 g, 156 millimoles (mmol)) was suspended in POCl$_3$ (130 mL) and brought to 102° C. under an atmosphere of N$_2$. After 45 min, all of the solids had dissolved, so the reaction was cooled to room temperature (RT). The resulting solids were collected by filtration, washed with H$_2$O, and then partitioned with CH$_2$Cl$_2$ (3 L) and 2M Na$_2$CO$_3$ (500 mL). The organic layer was separated, washed with H$_2$O (1×), dried over Na$_2$SO$_4$, filtered, and concentrated to afford 33.7 g of 7-bromo-4-chloro-3-nitroquinoline as a beige solid.

$^1$H NMR (300 MHz, CDCl$_3$) δ 9.26 (s, 1H), 8.41 (d, J=1.8 Hz, 1H), 8.30 (d, J=9.0 Hz, 1H), 7.90 (dd, J=8.9, 2.1 Hz, 1H).

Example 1

7-(1,1-Dioxo-[1,2]thiazinan-2-yl)-2-ethoxymethyl-1-(3-isopropoxypropyl)-1H-imidazo[4,5-c]quinolin-4-amine

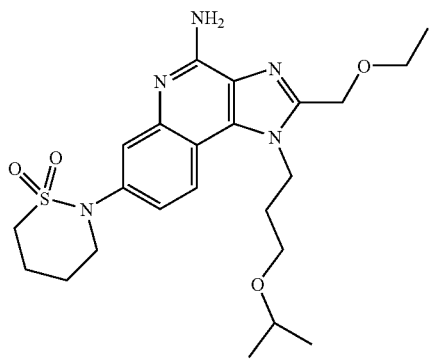

Part A

7-Bromo-4-chloro-3-nitroquinoline (40 g) was dissolved in dichloromethane (1.4 L) and triethylamine (23.3 mL). 3-Isopropoxypropylamine (19.3 mL) was added dropwise. After 48 hours, the reaction mixture washed successively with water and saturated aqueous sodium chloride. The organic fraction was dried over anhydrous sodium sulfate, filtered and concentrated under reduced pressure. (7-Bromo-3-nitroquinolin-4-yl)-(3-isopropoxypropyl)amine was isolated as a tan solid (51.2 g).

Part B (7-Bromo-3-nitroquinolin-4-yl)-(3-isopropoxypropyl)amine (51 g) was slurried in acetonitrile (750 mL) and added to a Parr flask containing 5% platinum on carbon (5 g). The flask was degassed three times, then charged with hydrogen (30 psi) and shaken for 4 hours with replenishment of the hydrogen as necessary. The platinum catalyst was removed by filtration through a bed of CELITE filter agent. The filtrate was evaporated to afford 7-bromo-$N^4$-(3-isopropoxypropyl)quinoline-3,4-diamine as a yellow oil (45 g).

Part C

7-Bromo-$N^4$-(3-isopropoxypropyl)quinoline-3,4-diamine (45 g) was dissolved in acetonitrile (1.3 L) and triethylamine (19.4 mL). Ethoxyacetyl chloride (18.0 g) was added dropwise to the solution and the reaction was stirred for 16 hours. The solvent was removed under reduced pressure to afford a tan solid. The solid was added to a solution of ethanol (1 L) and triethylamine (77.5 mL) and heated at reflux for 4 hours. The solvent was removed under reduced pressure. Water was added to the solid residue and the crude product was recovered by filtration. Recrystallization from acetonitrile yielded 36.25 g of 7-bromo-2-ethoxymethyl-1-(3-isopropoxypropyl)-1H-imidazo[4,5-c]quinoline as a tan crystalline solid.

Part D

7-Bromo-2-ethoxymethyl-1-(3-isopropoxypropyl)-1H-imidazo[4,5-c]quinoline (20 g) was dissolved in chloroform (400 mL). 3-Chloroperoxybenzoic acid (60% pure, 17.1 g) was added in 2 g portions over a 5 minute period and the reaction was stirred for 1 hour. Ammonium hydroxide (300 mL) was added and the mixture was cooled to 5° C. with an ice/water bath. p-Toluenesulfonyl chloride (9.4 g) was added at the rate of 1 g/min to minimize gas evolution. After stirring for 16 hours, the layers were separated and the aqueous fraction was extracted with chloroform. The combined organic fractions were sequentially washed with 5% aqueous sodium bicarbonate, water and brine; dried over anhydrous sodium sulfate, filtered and concentrated under reduced pressure. The residue was purified by flash column chromatography on silica gel. The polar component of the eluent was chloroform:methanol:ammonium hydroxide 80:18:2 (CMA). The purification was carried out eluting with chloroform:CMA in a gradient from 98:2 to 88:12. The material recovered from the column was recrystallized from acetonitrile to yield 7.0 g of 7-bromo-2-ethoxymethyl-1-(3-isopropoxypropyl)-1H-imidazo[4,5-c]quinolin-4-amine as a tan granular powder.

Part E

7-Bromo-2-ethoxymethyl-1-(3-isopropoxypropyl)-1H-imidazo[4,5-c]quinolin-4-amine (0.75 g), 1,4-butanesultam (0.29 g), copper(I) iodide (68 mg), (±)-trans-1,2-diaminocyclohexane (42 μL), potassium phosphate (0.79 g) and dioxane (4 mL) were added to a scintillation vial. The vial was flushed with nitrogen, sealed with a Teflon-lined cap, placed in an oil bath, and heated at 110° C. for 30 hours. The reaction was cooled to ambient temperature, diluted with chloroform and filtered through a bed of CELITE filter agent. The solvent was evaporated and the residue was purified by column chromatography on a Biotage Horizon™ High-Performance Flash Chromatography instrument using a silica gel cartridge. The polar component of the eluent was chloroform:methanol:ammonium hydroxide 80:18:2 (CMA). The purification was carried out eluting with chloroform:CMA in a gradient from 99:1 to 90:10. Additional purification by recrystallization from acetonitrile provided 0.47 g of 7-(1,1-dioxo-[1,2]thiazinan-2-yl)-2-ethoxymethyl-1-(3-isopropoxypropyl)-1H-imidazo[4,5-c]quinolin-4-amine as pale yellow crystals, mp 172-174° C.

$^1$H NMR (300 MHz, DMSO-$d_6$) δ 8.17 (d, J=8.8 Hz, 1H), 7.51 (d, J=2.2 Hz, 1H), 7.18 (dd, J=8.8, 2.2 Hz, 1H), 6.68 (s, 2H), 4.78 (s, 2H), 4.65-4.60 (m, 2H), 3.76-3.72 (m, 2H), 3.64-3.48 (m, 5H), 3.34-3.30 (m, 2H), 2.25-2.13 (m, 2H), 2.13-2.00 (m, 2H), 1.92-1.78 (m, 2H), 1.17 (t, J=7.2 Hz, 3H), 1.15 (d, J=6.0 Hz, 6H);

$^{13}$C NMR (75 MHz, DMSO-$d_6$) δ 152.4, 149.0, 145.6, 139.2, 132.7, 126.3, 123.0, 120.8, 120.2, 113.1, 70.8, 65.4, 64.1, 63.9, 53.2, 50.0, 42.9, 30.3, 23.9, 23.6, 22.0, 14.9;

MS (ESI) m/z 476.2336 (476.2332 calcd. for $C_{23}H_{33}N_5O_4S$, M+H);

Anal. Calcd. for $C_{23}H_{33}N_5O_4S$: % C, 58.08; % H, 6.99; % N, 14.72; % S, 6.74. Found: % C, 57.89; % H, 7.03; % N, 14.81; % S, 6.51.

Example 2

1-[4-Amino-2-ethoxymethyl-1-(3-isopropoxypropyl)-1H-imidazo[4,5-c]quinolin-7-yl]pyrrolidin-2-one

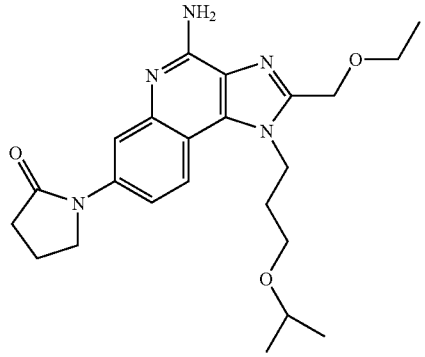

Part A

7-Bromo-2-ethoxymethyl-1-(3-isopropoxypropyl)-1H-imidazo[4,5-c]quinoline (0.5 g), copper(I) iodide (0.046 g), (+)-trans-1,2-diaminocyclohexane (0.030 mL), 2-pyrrolidinone (0.122 mL), potassium phosphate (0.55 g) and dioxane (1.2 mL) were added to a 2 dram vial with a stir bar. The vial was flushed with nitrogen, sealed with a Teflon-lined cap, placed in an oil bath, and heated at 110° C. for 16 hours. The reaction was cooled to ambient temperature and then diluted with chloroform and water. The layers were separated and the aqueous fraction was extracted with chloroform. The combined organic fractions were sequentially washed with water and saturated aqueous sodium chloride; dried over anhydrous sodium sulfate; filtered and concentrated under reduced pressure. The residue was purified by column chromatography on a Biotage Horizon™ High-Performance Flash Chromatography instrument using a silica gel cartridge. The polar component of the eluent was chloroform:methanol:ammonium hydroxide 80:18:2 (CMA). The purification was carried out eluting with chloroform:CMA in a gradient from 99:1 to 80:20. 1-[2-Ethoxymethyl-1-(3-isopropoxypropyl)-1H-imidazo[4,5-c]quinolin-7-yl]pyrrolidin-2-one was isolated as a yellow oil which solidified over time (0.38 g).

Part B

1-[2-Ethoxymethyl-1-(3-isopropoxypropyl)-1H-imidazo[4,5-c]quinolin-7-yl]pyrrolidin-2-one (0.38 g) was dissolved in chloroform (10 mL). 3-Chloroperoxybenzoic acid (60% pure, 0.37 g) was added in one portion and the mixture was allowed to stir for 16 hours. Ammonium hydroxide (10 mL) was added and the biphasic mixture was cooled to 2° C. with an ice/water bath. Benzenesulfonyl chloride (0.22 mL) was added and the reaction was stirred for 3 hours. The layers were separated and the aqueous fraction was extracted with chloroform. The combined organic fractions were sequentially washed with water and saturated aqueous sodium chloride; dried over anhydrous sodium sulfate; filtered and concentrated under reduced pressure. The residue was purified by column chromatography on a Biotage Horizon™ High-Performance Flash Chromatography instrument using a silica gel cartridge. The polar component of the eluent was chloroform:methanol:ammonium hydroxide 80:18:2 (CMA). The purification was carried out eluting with chloroform:CMA in a gradient from 99:1 to 73:27. Fractions containing product were combined and concentrated under reduced pressure. The residue was recrystallized from acetonitrile to afford 0.14 g of 1-[4-amino-2-ethoxymethyl-1-(3-isopropoxypropyl)-1H-imidazo[4,5-c]quinolin-7-yl]pyrrolidin-2-one as a white solid, mp 165-167° C.

$^1$H NMR (300 MHz, DMSO-$d_6$) δ 8.16 (d, J=8.9 Hz, 1H), 7.76 (dd, J=8.9, 2.3 Hz, 1H), 7.72 (d, J=2.2 Hz, 1H), 6.58 (s, 2H), 4.76 (s, 2H), 4.64-4.59 (m, 2H), 3.93 (t, J=7.0 Hz, 2H), 3.66-3.50 (m, 3H), 3.50 (t, J=5.6 Hz, 2H), 2.56-2.50 (m, 2H), 2.15-2.02 (m, 4H), 1.17 (t, J=7.0 Hz, 3H), 1.15 (d, J=6.0 Hz, 6H);

$^{13}$C NMR (75 MHz, DMSO-$d_6$) δ 173.9, 152.3, 148.6, 145.6, 138.4, 133.0, 125.7, 120.6, 115.3, 113.9, 110.9, 70.8, 65.4, 64.1, 63.9, 48.1, 42.8, 32.4, 30.3, 22.0, 17.4, 14.9;

MS (ESI) m/z 425.2506 (426.2505 calcd. for $C_{23}H_{31}N_5O_3$, M+H);

Anal. Calcd. for $C_{23}H_{31}N_5O_3$: % C, 64.92; % H, 7.34; % N, 16.46. Found: % C, 64.75; % H, 7.62; % N, 16.70.

Example 3

3-[4-Amino-2-ethoxymethyl-1-(3-isopropoxypropyl)-1H-imidazo[4,5-c]quinolin-7-yl]oxazolidin-2-one

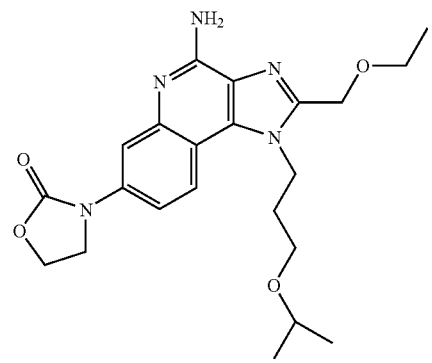

The general methods described in Parts A and B of Example 2 were followed using 2-oxazolidinone in lieu of 2-pyrrolidinone. The product, 3-[4-amino-2-ethoxymethyl-1-(3-isopropoxypropyl)-1H-imidazo[4,5-c]quinolin-7-yl]oxazolidin-2-one, was isolated as a white solid, mp 166-167° C.

$^1$H NMR (300 MHz, DMSO-$d_6$) δ 8.19 (d, J=9.0 Hz, 1H), 7.67 (dd, J=9.0, 2.3 Hz, 1H), 7.61 (d, J=2.3 Hz, 1H), 6.61 (s, 2H), 4.76 (s, 2H), 4.65-4.60 (m, 2H), 4.50-4.45 (m, 2H), 4.19-4.14 (m, 2H), 3.64-3.48 (m, 5H), 2.13-2.02 (m, 2H), 1.17 (t, J=7.0 Hz, 3H), 1.15 (d, J=6.0 Hz, 6H);

$^{13}$C NMR (125 MHz, DMSO-$d_6$) δ 154.9, 152.4, 148.6, 145.7, 137.3, 132.9, 125.7, 121.0, 113.9, 112.3, 110.6, 70.7, 65.3, 64.0, 63.8, 61.4, 44.7, 42.8, 30.3, 21.9, 14.8;

MS (ESI) m/z 428.2295 (428.2298 calcd. for $C_{22}H_{29}N_5O_4$, M+H);

Anal. Calcd. for $C_{22}H_{29}N_5O_4$: % C, 61.81; % H, 6.84; % N, 16.38. Found: % C, 61.62; % H, 6.84; % N, 16.34.

Example 4

1-[4-Amino-2-ethoxymethyl-1-(3-isopropoxypropyl)-1H-imidazo[4,5-c]quinolin-7-yl]piperidin-2-one

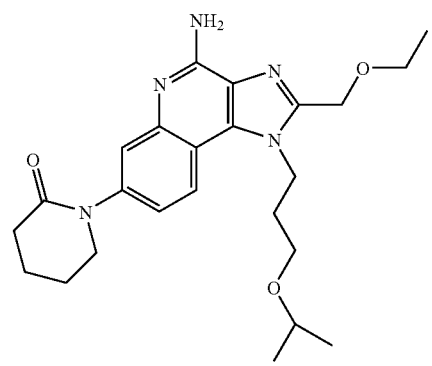

The general methods described in Parts A and B of Example 2 were followed using 2-piperidone in lieu of 2-pyrrolidinone. The product, 1-[4-amino-2-ethoxymethyl-1-(3- isopropoxypropyl)-1H-imidazo[4,5-c]quinolin-7-yl]piperidin-2-one, was isolated as a yellow crystalline solid, mp 205-206.5° C.

$^1$H NMR (300 MHz, DMSO-d$_6$) δ 8.16 (d, J=8.8 Hz, 1H), 7.45 (d, J=2.1 Hz, 1H), 7.16 (dd, J=8.7, 2.1 Hz, 1H), 6.63 (s, 2H), 4.77 (s, 2H), 4.66-4.61 (m, 2H), 3.71-3.67 (m, 2H), 3.64-3.48 (m, 5H), 2.45-2.41 (m, 2H), 2.15-2.02 (m, 2H), 1.96-1.80 (m, 4H), 1.17 (t, J=7.0 Hz, 3H), 1.15 (d, J=6.0 Hz, 6H);

$^{13}$C NMR (75 MHz, DMSO-d$_6$) δ 168.8, 152.2, 148.9, 145.7, 142.4, 132.9, 126.1, 122.5, 120.5, 120.1, 112.6, 70.8, 65.4, 64.1, 63.9, 50.9, 42.9, 32.7, 30.3, 23.1, 22.0, 20.9, 14.9;

MS (ESI) m/z 440.2661 (440.2662 calcd. for C$_{24}$H$_{33}$N$_5$O$_3$, M+H);

Anal. Calcd. for C$_{24}$H$_{33}$N$_5$O$_3$: % C, 65.58; % H, 7.57; % N, 15.93. Found: % C, 65.34; % H, 7.80; % N, 15.92.

Example 5

1-[4-Amino-2-ethoxymethyl-1-(3-isopropoxypropyl)-1H-imidazo[4,5-c]quinolin-7-yl]azetidin-2-one

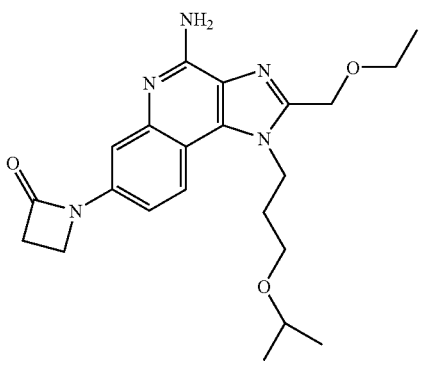

The general methods described in Parts A and B of Example 2 were followed using 2-azetidinone in lieu of 2-pyrrolidinone. The product, 1-[4-amino-2-ethoxymethyl-1-(3-isopropoxypropyl)-1H-imidazo[4,5-c]quinolin-7-yl]azetidin-2-one, was isolated as a flocculent white solid, mp 185-186° C.

$^1$H NMR (300 MHz, DMSO-d$_6$) δ 8.16 (d, J=8.8 Hz, 1H), 7.42 (d, J=2.0 Hz, 1H), 7.39 (dd, J=8.7, 2.2 Hz, 1H), 6.60 (s, 2H), 4.76 (s, 2H), 4.63-4.58 (m, 2H), 3.71 (t, J=4.4 Hz, 2H), 3.64-3.48 (m, 5H), 3.11 (t, J=4.3 Hz, 2H), 2.12-2.00 (m, 2H), 1.19-1.14 (m, 3H), 1.15 (d, J=6.0 Hz, 6H);

$^{13}$C NMR (125 MHz, DMSO-d$_6$) δ 164.7, 152.5, 148.5, 146.0, 137.3, 133.1, 125.5, 121.5, 111.2, 110.8, 110.7, 70.7, 65.3, 64.1, 63.9, 42.8, 37.9, 35.6, 30.3, 22.0, 14.9;

MS (ESI) m/z 412.2341 (412.2349 calcd. for C$_{22}$H$_{29}$N$_5$O$_3$, M+H);

Anal. Calcd. for C$_{22}$H$_{29}$N$_5$O$_3$: % C, 64.21; % H, 7.10; % N, 17.02. Found: % C, 63.98; % H, 7.38; % N, 17.07.

Example 6

1-[4-Amino-2-ethoxymethyl-1-(2-hydroxy-2-methylpropyl)-1H-imidazo[4,5-c]quinolin-7-yl]pyrrolidin-2-one

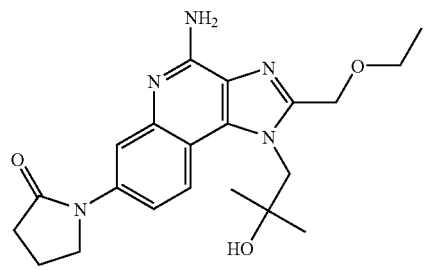

The general methods described in Parts A and B of Example 2 were followed using 1-(7-bromo-2-ethoxymethyl-1H-imidazo[4,5-c]quinolin-1-yl)-2-methylpropan-2-ol in lieu of 7-bromo-2-ethoxymethyl-1-(3-isopropoxypropyl)-1H-imidazo[4,5-c]quinoline. The product, 1-[4-amino-2-ethoxymethyl-1-(2-hydroxy-2-methylpropyl)-1H-imidazo[4,5-c]quinolin-7-yl]pyrrolidin-2-one, was isolated as a beige powder, mp 200-202° C.

$^1$H NMR (300 MHz, DMSO-d$_6$) δ 8.24 (d, J=9.0 Hz, 1H), 7.74 (dd, J=9.0, 2.3 Hz, 1H), 7.69 (d, J=2.3 Hz, 1H), 6.55 (s, 2H), 5.0-4.8 (bs, 1H), 4.87 (s, 2H), 4.65 (bs, 2H), 3.92 (t, J=7.0 Hz, 2H), 3.51 (q, J=7.0 Hz, 2H), 2.56-2.50 (m, 2H), 2.14-2.04 (m, 2H), 1.17 (bs, 6H), 1.13 (d, J=7.0 Hz, 3H);

MS (ESI) m/z 398.2193 (398.2192 calcd. for C$_{21}$H$_{27}$N$_5$O$_3$, M+H);

Anal. Calcd. for C$_{21}$H$_{27}$N$_5$O$_3$: % C, 63.46; % H, 6.85; % N, 17.62. Found: % C, 63.08; % H, 6.61; % N, 17.40.

Example 7

3-[4-Amino-2-ethoxymethyl-1-(2-hydroxy-2-methylpropyl)-1H-imidazo[4,5-c]quinolin-7-yl]oxazolidin-2-one

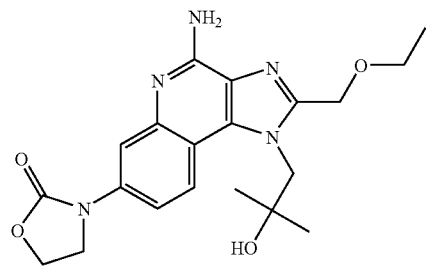

The general method described in Part E of Example 1 was followed using 1-(4-amino-7-bromo-2-ethoxymethyl-1H-imidazo[4,5-c]quinolin-1-yl)-2-methylpropan-2-ol and 2-oxazolidinone as reactants in lieu of 7-bromo-2-ethoxymethyl-1-(3-isopropoxypropyl)-1H-imidazo[4,5-c]quinolin-4-amine and 2-pyrrolidinone. The product, 3-[4-amino-2-ethoxymethyl-1-(2-hydroxy-2-methylpropyl)-1H-imidazo

[4,5-c]quinolin-7-yl]oxazolidin-2-one, was isolated as a flocculent white solid, mp >250° C.

$^1$H NMR (300 MHz, DMSO-$d_6$) δ 8.27 (d, J=9.0 Hz, 1H), 7.64 (dd, J=9.0, 2.5 Hz, 1H), 7.60 (d, J=2.4 Hz, 1H), 6.56 (s, 2H), 5.02-4.77 (bs, 1H), 4.87 (s, 2H), 4.65 (bs, 2H), 4.50-4.44 (m, 2H), 4.18-4.13 (m, 2H), 3.51 (q, J=7.0 Hz, 2H), 1.17 (bs, 6H), 1.13 (d, J=7.0 Hz, 3H);

MS (ESI) m/z 400.1987 (400.1985 calcd. for $C_{20}H_{25}N_5O_4$, M+H);

Anal. Calcd. for $C_{20}H_{25}N_5O_4$: % C, 60.14; % H, 6.31; % N, 17.53. Found: % C, 59.88; % H, 6.19; % N, 17.36.

Example 8

2-Ethoxymethyl-1-(3-isopropoxypropyl)-7-(morpholin-4-yl)-1H-imidazo[4,5-c]quinolin-4-amine

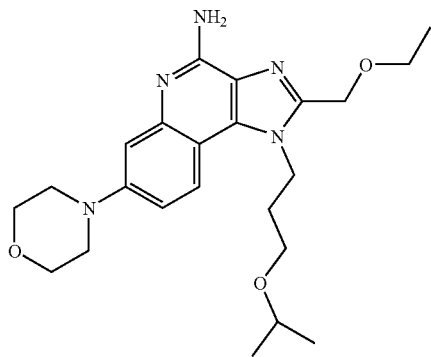

Part A

7-Bromo-2-ethoxymethyl-1-(isopropoxypropyl)-1H-imidazo[4,5-c]quinoline (1.0 g), (+)-2,2'-bis(diphenylphosphino)-1,1'binaphthyl (BINAP, 0.089 g), tris(dibenzylideneacetone)dipalladium(0) (0.074 g), sodium tert-butoxide (0.320 g,), morpholine (0.230 mL,) and toluene (4.8 mL) were added to a scintillation vial. The vial was sequentially flushed with nitrogen, sealed with a Teflon-lined cap, placed in an oil bath, and heated at 80° C. for 16 hours. The reaction mixture was cooled to ambient temperature and then transferred to a round bottom flask. The volatiles were removed under reduced pressure and the residue was purified by column chromatography on a Biotage Horizon™ High Performance Flash Chromatography instrument using a silica gel cartridge. The purification was carried out eluting with chloroform:CMA in a gradient from 98:2 to 75:25. 2-Ethoxymethyl-1-(3-isopropoxypropyl)-7-(morpholin-4-yl)-1H-imidazo[4,5-c]quinoline was isolated as a red-orange oil (1.32 g).

Part B

2-Ethoxymethyl-1-(3-isopropoxypropyl)-7-(morpholin-4-yl)-1H-imidazo[4,5-c]quinoline (1.0 g), benzonitrile (0.44 mL) and sodium bicarbonate (0.15 g) were slurried in methanol. Hydrogen peroxide (55% by weight in water, 0.395 mL) was added dropwise over 1 hour. The reaction was stirred overnight. The methanol was removed under reduced pressure and the residue was purified by column chromatography on a Biotage Horizon™ High Performance Flash Chromatography instrument. The purification was carried out eluting with chloroform:CMA in a gradient from 98:2 to 75:25. 2-Ethoxymethyl-1-(3-isopropoxypropyl)-7-(morpholin-4-yl)-1H-imidazo[4,5-c]quinoline 5-oxide was isolated as a yellow oil (0.166 g).

Part C

2-Ethoxymethyl-1-(3-isopropoxypropyl)-7-(morpholin-4-yl)-1H-imidazo[4,5-c]quinoline 5-oxide from Part B was dissolved in dichloromethane (4 mL). Ammonium hydroxide (2 mL) was added, followed by p-toluenesulfonyl chloride (0.074 g). The reaction was stirred for 24 hours. The layers were separated and the aqueous fraction was extracted with dichloromethane. The combined organic fractions were concentrated under reduced pressure to yield a yellow-brown oil. The oil was covered with diethyl ether and a precipitate formed. The solid was recovered by filtration and then dried to provide 0.085 g of 2-ethoxymethyl-1-(3-isopropoxypropyl)-7-(morpholin-4-yl)-1H-imidazo[4,5-c]quinolin-4-amine as a white powder, mp 161-162.5° C.

$^1$H NMR (300 MHz, DMSO-$d_6$) δ 8.03 (d, J=9.7 Hz, 1H), 7.01-6.99 (m, 2H), 6.40 (s, 2H), 4.73 (s, 2H), 4.60-4.55 (m, 2H), 3.79-3.76 (m, 4H), 3.63-3.46 (m, 5H), 3.20-3.17 (m, 4H), 2.11-1.99 (m, 2H), 1.18-1.14 (m, 3H), 1.15 (d, J=6.1 Hz, 6H);

$^{13}$C NMR (125 MHz, DMSO-$d_6$) δ 152.0, 150.0, 147.8, 146.6, 133.4, 124.7, 121.0, 111.7, 109.7, 107.7, 70.7, 66.1, 65.2, 64.0, 63.8, 48.4, 42.6, 30.2, 21.9, 14.8;

MS (ESI) m/z 428.2655 (428.2662 calcd. for $C_{23}H_{33}N_5O_3$, M+H);

Anal. Calcd. for $C_{23}H_{33}N_5O_3$: % C, 64.61; % H, 7.78; % N, 16.38. Found: % C, 64.40; % H, 8.05; % N, 16.34.

Example 9

1-[4-Amino-2-ethoxymethyl-1-(3-isopropoxypropyl)-1H-imidazo[4,5-c]quinolin-7-yl]-1H-pyridin-2-one

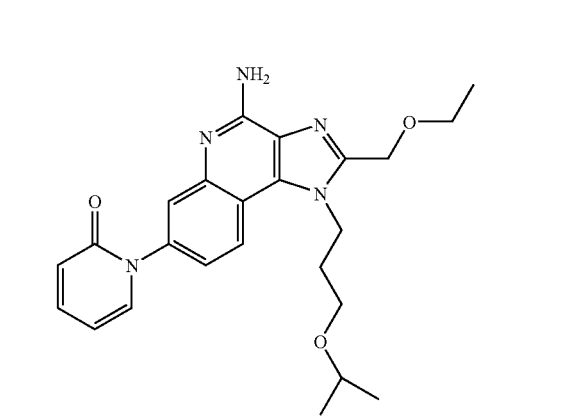

7-Bromo-2-ethoxymethyl-1-(3-isopropoxypropyl)-1H-imidazo[4,5-c]quinolin-4-amine (0.75 g), 2(1H)-pyridone (0.20 g), copper(I) iodide (68 mg), N,N'-dimethylethylenediamine (75 μL), potassium phosphate (0.79 g) and dioxane (2.7 mL) were added to a scintillation vial. The vial was flushed with nitrogen, sealed with a Teflon-lined cap, placed in an oil bath, and heated to 110° C. for 60 hours. The reaction was cooled to ambient temperature, diluted with chloroform and filtered through a bed of CELITE filter agent. The solvent was evaporated and the residue was purified by column chromatography on a Biotage Horizon™ High-Performance Flash Chromatography instrument using a silica gel cartridge. The purification was carried out eluting with chloroform:CMA in a gradient from 99:1 to 75:25. Additional purification by recrystallization from acetonitrile provided 0.38 g of 1-[4-amino-2-ethoxymethyl-1-(3-isopropoxypropyl)-1H-imidazo[4,5-c]quinolin-7-yl]-1H-pyridin-2-one as a tan solid, mp 161-163.5° C.

$^1$H NMR (300 MHz, DMSO-d$_6$) δ 8.30 (d, J=8.8 Hz, 1H), 7.75 (dd, J=6.8, 1.7 Hz, 1H), 7.56-7.50 (m, 2H), 7.24 (dd, J=8.7, 2.2 Hz, 1H), 6.80 (s, 2H), 6.51 (d, J=9.1 Hz, 1H), 6.36-6.31 (m, 1H), 4.80 (s, 2H), 4.70-4.65 (m, 2H), 3.64-3.49 (m, 5H), 2.17-2.03 (m, 2H), 1.18 (t, J=7.0 Hz, 3H), 1.15 (d, J=6.0 Hz, 6H);

$^{13}$C NMR (75 MHz, DMSO-d$_6$) δ 161.3, 152.6, 149.3, 145.6, 140.5, 139.4, 139.2, 132.7, 126.6, 123.4, 121.0, 120.5, 119.7, 114.0, 105.5, 70.8, 65.5, 64.1, 63.9, 42.9, 30.3, 22.0, 14.9;

MS (APCI) m/z 436 (M+H)$^+$;

Anal. Calcd. for C$_{24}$H$_{29}$N$_5$O$_3$: % C, 66.19; % H, 6.71; % N, 16.08. Found: % C, 65.90; % H, 7.02; % N, 15.91.

Example 10

3-[4-Amino-2-ethoxymethyl-1-(2-methylpropyl)-1H-imidazo[4,5-c][1,5]naphthyridin-7-yl]-1,3-oxazolidin-2-one

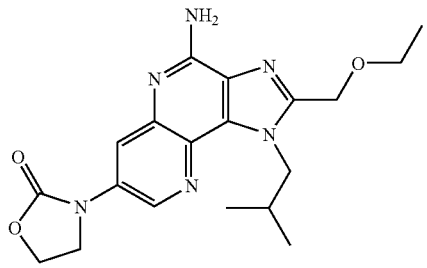

Part A

A mixture of triethyl orthoformate (10 mL, 60.1 mmol) and 2,2-dimethyl-[1,3]-dioxane-4,6-dione (40.9 g, 0.23 mol) (Meldrum's acid) was heated at 92° C. for 90 minutes and then cooled to 70° C. over one hour. 3-Amino-5-bromopyridine (40.9 g, 0.20 mol) was slowly added over 10 minutes with an ethanol rinse while maintaining the reaction temperature between 60 and 70° C. The reaction was then heated for an additional 20 minutes and allowed to cool to room temperature. The reaction mixture was filtered and washed with ethanol (150 mL) yielding a tan solid. The solid was dried under vacuum for 2 hours to yield 59.14 g of 5-{[(5-bromopyridin-3-yl)imino]methyl}-2,2-dimethyl-1,3-dioxane-4,6-dione as a light yellow crystalline solid, mp 200-202° C.

$^1$H NMR (300 MHz, CDCl$_3$) δ 11.26 (d, J=14.3 Hz, 1H), 8.80 (d, J=2.3 Hz, 1H), 8.62 (d, J=14.3 Hz, 1H), 8.56(d, J=1.9 Hz, 1H), 8.44-8.40 (m, 1H), 1.68 (s, 6H).

Part B

5-{[(5-Bromopyridin-3-yl)imino]methyl}-2,2-dimethyl-1,3-dioxane-4,6-dione (59 g, 0.18 mol) was slowly added to DOWTHERM A heat transfer fluid (2000 mL) over a period of 5 minutes at 235-238° C. Following addition, the reaction was maintained for an additional 5 minutes and then allowed to cool to 40° C. A brown precipitate formed, which was filtered and washed with hexanes (150 mL). The brown solid was suspended in an ethanol/water mixture (90:10, 1500 mL), heated to a boil for 30 minutes, isolated by filtration, and washed with ethanol (200 mL) to yield 30.8 g of 7-bromo[1,5]naphthyridin-4-ol as a dark brown powder.

$^1$H NMR (300 MHz, CDCl$_3$) δ 11.81(br s, 1H), 8.69(d, J=1.9 Hz, 1H), 8.21 (d, J=1.9 Hz, 1H), 7.95(d, J=7.7 Hz, 1H), 6.22 (d, J=7.5 Hz, 1H).

Part C

A mixture of 7-bromo[1,5]naphthyridin-4-ol (33 g, 0.147 mol) and fuming nitric acid (350 mL) was heated at reflux (90° C. internal reaction vessel temperature) for 3 hours. The reaction mixture was cooled to 50° C., poured over 1 L of ice and neutralized to pH 2-3 with a solution of 50% aqueous NaOH. The resulting precipitate was filtered, washed with water, and dried over vacuum for 3 days to yield 25.1 g of 7-bromo-3-nitro[1,5]naphthyridin-4-ol as a yellow crystalline solid.

$^1$H NMR (300 MHz, CDCl$_3$) δ 13.06(br s, 1H), 9.26(s, 1H), 8.88 (d, J=2.0 Hz, 1H), 8.37(d, J=2.0 Hz, 1H).

Part D

Phosphorous oxychloride (16.76 g, 10.19 mL, 109.3 mmol) was added slowly dropwise to a suspension of 7-bromo-3-nitro[1,5]naphthyridin-4-ol (21.09 g, 78.1 mmol) in N,N-dimethylformamide (250 mL) (DMF) at ambient temperature and maintained overnight. The reaction mixture was then added to ice water (400 mL) with stirring. A solid precipitate formed, which was isolated by vacuum filtration and washed with water. The material was dried under high vacuum at ambient temperature overnight to yield 20.79 g of 7-bromo-4-chloro-3-nitro[1,5]naphthyridine as a tan solid.

$^1$H NMR (300 MHz, CDCl$_3$) δ 9.51(s, 1H), 9.36 (d, J=2.2 Hz, 1H), 9.02(d, J=2.1 Hz, 1H).

Part E

Triethylamine (17.97 mL, 129.0 mmol) was added to a solution of 7-bromo-4-chloro-3-nitro[1,5]naphthyridine (24.8 g, 86.0 mmol) in dichloromethane (200 mL) at 0° C. Isobutylamine (9.40 mL, 94.6 mmol) was added dropwise to the mixture, and the mixture was stirred for 3 hours at ambient temperature. The reaction mixture was condensed under reduced pressure to a solid, which was triturated with water (200 mL). The precipitate was filtered, washed sequentially with water and hexanes, and dried to yield 27.5 g of 7-bromo-3-nitro[1,5]naphthyridin-4-yl-(2-methylpropyl)amine as a yellow powder, mp 114-115° C.

$^1$H NMR (300 MHz, CDCl$_3$) δ 9.98(br s, 1H), 9.37(br s, 1H), 8.81 (d, J=2.2 Hz, 1H), 8.39(d, J=2.2 Hz, 1H), 4.36-4.01 (br m, 2H), 2.06(heptet, J=6.7 Hz, 1H), 1.09(d, J=6.7, 6H).

MS (APCI) m/z 325.2 and 327.2 (M+H)$^+$;

Anal. calcd for C$_{12}$H$_{13}$BrN$_4$O$_2$: C, 44.33; H, 4.03; N, 17.23. Found: C, 44.32; H, 3.81; N, 17.33.

Part F

A solution of sodium dithionite (77.95 g, 380.6 mmol) and potassium carbonate (58.35 g, 422.2 mmol) in water (250 mL) was added dropwise to a mechanically stirred solution of 7-bromo-3-nitro[1,5]naphthyridin-4-yl-(2-methylpropyl)amine (27.6 g, 84.6 mmol) and ethyl viologen dibromide (0.63 g, 1.7 mmol) in dichloromethane (300 mL) and water (50 mL). The reaction mixture was stirred overnight at ambient temperature. Water (500 mL) was added, and the reaction mixture was stirred for 10 minutes. The organic layer was separated and the aqueous layer was filtered through WHATMAN paper to remove insoluble material. The emulsion-free filtrate was extracted with dichloromethane, washed sequentially with water and brine, dried over sodium sulfate, filtered, and concentrated under reduced pressure to yield 22.3 g of 7-bromo-N$^4$-(2-methylpropyl)[1,5]naphthyridine-3,4-diamine as an orange solid.

$^1$H NMR (300 MHz, CDCl$_3$) δ 8.70 (d, J=2.2 Hz, 1H), 8.36(s, 1H), 8.33(d, J=2.2 Hz, 1H), 6.03-5.89(br m, 1H), 3.66(br s, 2H), 3.27(t, J=6.8, 2H), 1.83(heptet, J=6.7 Hz, 1H), 1.00(d, J=6.7 Hz, 6H). MS (APCI) m/z 295.1 and 297.1 (M+H)$^+$ Part G A solution of 7-bromo-N$^4$-(2-methylpropyl)[1,5]naphthyridine-3,4-diamine (22.29 g, 75.51 mmol) in dichloromethane (300 mL) was cooled to 0° C., and triethylamine (13.15 mL, 94.39 mmol) was added to the reaction mixture. Ethoxyacetyl chloride (11.56 g, 94.39 mmol) was added dropwise to the reaction mixture, and the reaction was maintained at ambient temperature for 2.5 hours. The reaction mixture was concentrated under reduced pressure, triethylamine (52.62 mL, 377.6 mmol) and ethanol (250 mL) was added, and the resulting mixture was heated at reflux for 16 hours. The solvent was removed under reduced pressure and the residue was triturated with n-heptanes. The resulting precipitate was collected by filtration, washed with water, and dried. The product was then recrystallized from acetonitrile to yield 14 g of 7-bromo-2-(ethoxymethyl)-1-(2-methylpropyl)-1H-imidazo[4,5-c][1,5]naphthyridine as an off-white solid. The mother liquor was concentrated, and the residue was recrystallized from acetonitrile to yield an additional 2.37 g of 7-bromo-2-(ethoxymethyl)-1-(2-methylpropyl)-1H-imidazo[4,5-c][1,5]naphthyridine. The n-heptanes fraction from the trituration was concentrated under reduced pressure, triturated with acetonitrile, and isolated by filtration to give an additional 0.88 g of 7-bromo-2-(ethoxymethyl)-1-(2-methylpropyl)-1H-imidazo[4,5-c][1,5]naphthyridine, for a total yield of 17.25 g of an off-white solid, mp 115-116° C.

$^1$H NMR (300 MHz, CDCl$_3$) δ 9.33(s, 1H), 8.96(d, J=2.2 Hz, 1H), 8.68(d, J=2.2 Hz, 1H), 4.90(s, 2H), 4.78(d, J=7.6 Hz, 2H), 3.64(q, J=7.0 Hz, 2H), 2.47(heptet, J=6.9 Hz, 1H), 1.26 (t, J=7.0, 3H), 0.98(d, J=7.0 Hz, 6H); $^{13}$C NMR (75 MHz, CDCl$_3$) δ 152.6, 149.7, 147.2, 140.3, 139.3, 139.1, 134.5, 133.9, 117.9, 66.5, 65.3, 53.2, 29.7, 19.8, 15.0.

Anal. calcd for C$_{16}$H$_{19}$BrN$_4$O: C, 52.90; H, 5.27; N, 15.42. Found: C, 52.93; H, 5.22; N, 15.55.

Part H

The general methods described in Parts A and B of Example 2 were followed using 7-bromo-2-(ethoxymethyl)-1-(2-methylpropyl)-1H-imidazo[4,5-c][1,5]naphthyridine in lieu of 7-bromo-2-(ethoxymethyl)-1-(3-isopropoxypropyl)-1H-imidazo[4,5-c]quinoline and 2-oxazolidinone in lieu of 2-pyrrolidinone. The product, 3-[4-amino-2-ethoxymethyl-1-(2-methylpropyl)-1H-imidazo[4,5-c][1,5]naphthyridin-7-yl]-1,3-oxazolidin-2-one (0.125 g) was isolated as an white solid with yellow tinge, m.p. 174-176.5° C.

MS(ESI) m/z 385.1977 (385.1988 calcd. for C$_{19}$H$_{24}$N$_6$O$_3$, M+H);

Anal. Calcd. for C$_{19}$H$_{24}$N$_6$O$_3$.0.6H$_2$O: % C, 57.74; % H, 6.43; % N, 21.26. Found: % C, 58.13; % H, 6.51; % N, 21.48.

Example 11

1-[4-Amino-2-ethoxymethyl-1-(2-hydroxy-2-methylpropyl)-1H-imidazo[4,5-c]quinolin-7-yl]-3-ethylimidazolidin-2-one

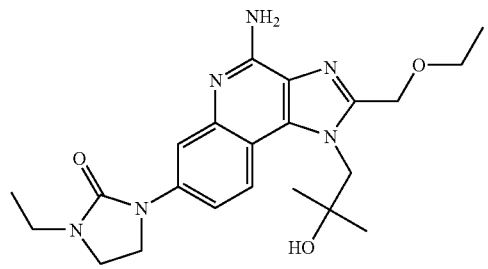

The general methods described in Parts A and B of Example 2 were followed using 1-(7-bromo-2-ethoxymethyl-1H-imidazo[4,5-c]quinolin-1-yl)-2-methylpropan-2-ol in lieu of 7-bromo-2-ethoxymethyl-1-(3-isopropoxypropyl)-1H-imidazo[4,5-c]quinoline and 1-ethylimidazolidin-2-one in lieu of 2-pyrrolidinone. The product, 1-[4-amino-2-ethoxymethyl-1-(2-hydroxy-2-methylpropyl)-1H-imidazo[4,5-c]quinolin-7-yl]-3-ethylimidazolidin-2-one was isolated as a peach colored crystalline solid, m.p. 210-212° C.

MS(ESI) m/z 427.2452 (427.2458 calcd. for C$_{22}$H$_{30}$N$_6$O$_3$, M+H);

Anal. Calcd. for C$_{22}$H$_{30}$N$_6$O$_3$.0.5H$_2$O: % C, 60.67; % H, 7.18; % N, 19.30. Found: % C, 60.61; % H, 7.19; % N, 19.19.

Example 12

2-Ethoxymethyl-1-(3-isopropoxypropyl)-7-(piperidin-1-yl)-1H-imidazo[4,5-c]quinolin-4-amine

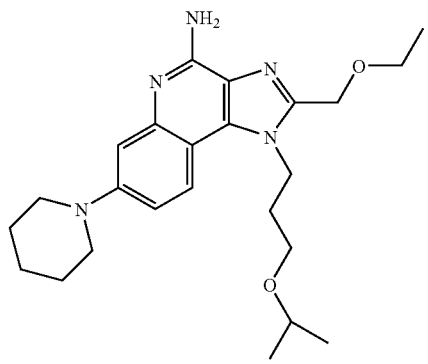

Part A

A slurry of 7-bromo-2-ethoxymethyl-1-(3-isopropoxypropyl)-1H-imidazo[4,5-c]quinoline (6.6 g, 16.2 mmol) in ethyl acetate (55 mL) was heated to 50° C. Peroxyacetic acid (5.12 mL, 24.4 mmol, of 32% in dilute acetic acid) was added dropwise over a period of 2 minutes. The reaction was allowed to stir at 50° C. for 2 hours. Additional peroxyacetic acid (1 mL) was added and the reaction mixture was stirred for an additional 2 hours. A solution of sodium metabisulfite (4.01 g, 21.1 mmol) in water (8 mL) was added. Following the addition of the sodium metabisulfite, the pH of the reaction mixture was adjusted to pH 10 with aqueous saturated sodium bicarbonate. The layers were separated and the aqueous layer was extracted with dichloromethane (2×50 mL). The combined organics were washed sequentially with water and brine, dried over sodium sulfate, filtered, and then concentrated under reduced pressure to provide a yellow solid. This material was purified by flash chromatography (150 g of silica gel eluting with a gradient of 1-12% CMA in chloroform) to provide 5.49 g of 7-bromo-2-ethoxymethyl-1-(3-isopropoxypropyl)-1H-imidazo[4,5-c]quinoline-5-oxide.

Part B

7-Bromo-2-ethoxymethyl-1-(3-isopropoxypropyl)-1H-imidazo[4,5-c]quinoline-5-oxide (0.500 g), water (4.0 mL), and piperidine (1.0 mL) were added sequentially to a 20 mL steel pressure vessel. The vessel was sealed and then heated in an oven at 150° C. for 16 hours. The reaction mixture was allowed to cool and then was extracted with chloroform (×2). The combined extracts were washed sequentially with water and brine and then dried over sodium sulfate. This material was combined with that from another run on the same scale and then purified by column chromatography on a Biotage Horizon™ High-Performance Flash Chromatography instrument using a silica gel cartridge and eluting with a gradient of 2-22% CMA in chloroform to provide 0.137 g of 2-ethoxymethyl-1-(3-isopropoxypropyl)-7-(piperidin-1-yl)-1H-imidazo[4,5-c]quinoline-5-oxide as a brown oil.

Part C

The material from Part B was dissolved in dichloromethane (5 mL). Ammonium hydroxide (2 mL) and p-toluenesulfonyl chloride (0.06 g, 0.32 mmol) were added sequentially. When analysis by thin layer chromatography indicated that the reaction was complete, the layers were separated. The organic layer washed with brine, dried over sodium sulfate, filtered, and then concentrated under reduced pressure. This material was combined with that from another run and purified by column chromatography on a Biotage Horizon™ High-Performance Flash Chromatography instrument using a silica gel cartridge and eluting with a gradient of 2-25% CMA in chloroform to provide an oil. The oil was triturated with acetonitrile to provide a solid which was isolated by filtration, washed with acetonitrile and dried under vacuum to provide 0.037 g of 2-ethoxymethyl-1-(3-isopropoxypropyl)-7-(piperidin-1-yl)-1H-imidazo[4,5-c]quinolin-4-amine as yellow crystals, m.p. 182.5-183.5° C.

MS (ESI) m/z 426.54 (M+H)$^+$;

Anal. Calcd. for $C_{24}H_{35}N_5O_2$: % C, 67.74; % H, 8.29; % N, 16.46. Found: % C, 67.43; % H, 8.53; % N, 16.51.

Example 13

1-[4-Amino-2-ethoxymethyl-1-(2-methylpropyl)-1H-imidazo[4,5-c][1,5]naphthyridin-7-yl]pyrrolidin-2-one

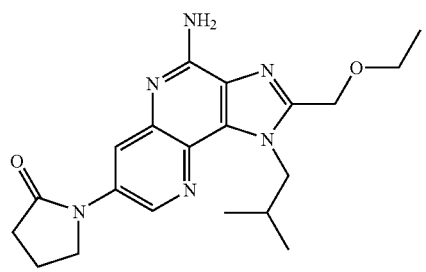

Part A

7-Bromo-2-(ethoxymethyl)-1-(2-methylpropyl)-1H-imidazo[4,5-c][1,5]naphthyridine (1.0 g, 2.75 mmol), tris(dibenzylideneacetone)dipalladium(0) (70 mg, 0.068 mmol), cesium carbonate (1.25 g, 3.85 mmol), 9,9-dimethyl-4,5-bis(diphenylphosphino)xanthene (0.118 g, 0.204 mmol), pyrrolidin-2-one (0.25 mL, 3.3 mmol), and dioxane (2.75 mL) were added to a scintillation vial. The vial was sequentially flushed with nitrogen, sealed with a Teflon-lined cap, and heated at 110° C. for about 40 hours. After cooling to room temperature, the reaction mixture was diluted with chloroform and methanol and then filtered through CELITE filter aid. The filtrate was concentrated under reduced pressure to provide a tan solid. This material was purified by column chromatography on a Biotage Horizon™ High-Performance Flash Chromatography instrument using a silica gel cartridge and eluting with a gradient of 1-25% CMA in chloroform to provide 1-[2-ethoxymethyl-1-(2-methylpropyl)-1H-imidazo[4,5-c][1,5]naphthyridin-7-yl]pyrrolidin-2-one.

Part B

The material from Part A was oxidized and then aminated using the general method of Part B of Example 2 except that p-toluenesulfonyl chloride was used in lieu of benzenesulfonyl chloride. The crude product was purified by column chromatography on a Biotage Horizon™ High-Performance Flash Chromatography instrument using a silica gel cartridge and eluting with a gradient of 1-22% CMA in chloroform followed by trituration with acetonitrile to provide 0.435 g of 1-[4-amino-2-ethoxymethyl-1-(2-methylpropyl)-1H-imidazo[4,5-c][1,5]naphthyridin-7-yl]pyrrolidin-2-one as an off-white solid, m.p. 197.5-198.5° C.

MS(ESI) m/z 383.2192 (383.2195 calcd. for $C_{20}H_{26}N_6O_2$, M+H);

Anal. Calcd. for $C_{20}H_{26}N_6O_2$: % C, 62.81; % H, 6.85; % N, 21.97. Found: % C, 62.52; % H, 6.92; % N, 21.71.

Example 14

3-[4-Amino-2-ethoxymethyl-1-(2-hydroxy-2-methylpropyl)-1H-imidazo[4,5-c]quinolin-8-yl]-1,3-oxazolidin-2-one

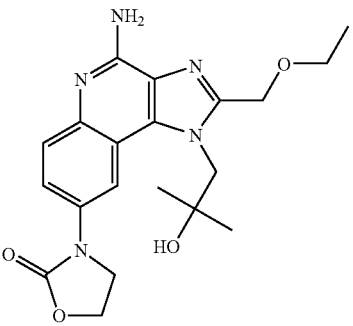

Part A

8-Bromo-2-ethoxymethyl-1H-imidazo[4,5-c]quinolin-1-yl)-2-methylpropan-2-ol (which can be prepared as described in US 2004/0147543, Examples 147-150) 0.550 g, 1.45 mmol), oxazolidin-2-one (0.151 g, 1.74 mmol), copper iodide (0.055 g), potassium phosphate (0.647 g, 3.05 mmol), dioxane (1.5 mL) and diaminocyclohexane (35 μL, 0.290 mmol) were added sequentially to a vial. The vial was flushed with nitrogen, sealed with a Teflon-lined cap, and heated at 110° C. over the weekend. The reaction mixture was allowed to cool and then it was diluted with dichloromethane (10 mL) and methanol (5 mL). The solution was purified by column chromatography on a Biotage Horizon™ High-Performance Flash Chromatography instrument using a silica gel cartridge and eluting with a gradient of 2-15% CMA in chloroform to provide 0.38 g of 3-[2-ethoxymethyl-1-(2-hydroxy-2-methylpropyl)-1H-imidazo[4,5-c]quinolin-8-yl]-1,3-oxazolidin-2-one.

Part B

The material from Part A was oxidized and then aminated using the general method of Part B of Example 2 except that p-toluenesulfonyl chloride was used in lieu of benzenesulfonyl chloride. The crude product was purified by column chromatography on a Biotage Horizon™ T High-Performance Flash Chromatography instrument using a silica gel cartridge and eluting with a gradient of 2-20% CMA in chloroform followed by recrystallization from acetonitrile to provide 0.167 g of 3-[4-amino-2-ethoxymethyl-1-(2-hydroxy-2-methylpropyl)-1H-imidazo[4,5-c]quinolin-8-yl]-1,3-oxazolidin-2-one as tan crystals, m.p. 207-209.5° C.

MS (APCI) m/z 400.15 (M+H)$^+$;

Anal. Calcd. for $C_{20}H_{25}N_5O_4$: % C, 60.14; % H, 6.31; % N, 17.53. Found: % C, 60.23; % H, 6.11; % N, 17.76.

Examples 15-30

A cyclic amide from the table below (1.2 eq) was added to a test tube containing 4 mg (0.2 eq) of copper iodide, 8 mg (2 eq) of potassium phosphate, and a magnetic stir bar. A solution of 7-bromo-2-ethoxymethyl-1-(3-isopropoxypropyl)-1H-imidazo[4,5-c]quinoline-4-amine (42 mg, 1.0 eq) in 1,4-dioxane (1.0 mL) was added to the test tube and the test tube was purged with nitrogen. trans-1,2-Diaminocyclohexane (4 µL, 0.3 eq) was added to the test tube and the test tube was purged with nitrogen. The test tube was capped and the reaction mixture was stirred at 110° C. overnight (about 16 hours). The test tube was cooled to ambient temperature and then charged with the appropriate cyclic amide, 4 mg (0.2 eq) of copper iodide, 8 mg (2 eq) of potassium phosphate, and trans-1,2-diaminocyclohexane (6 µL). The reaction mixture was stirred at 110° C. over the weekend. The reaction mixture was filtered and then concentrated by vacuum centrifugation. The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. The table below shows the cyclic amide used for each example, the structure of the resulting compound, and the observed accurate mass for the isolated trifluoroacetate salt.

| Example | Reagent | (structure) | Measured Mass (M + H) |
|---|---|---|---|
| 15 | 3-Methyl-2-pyyrolidinone | | 440.2621 |
| 16 | 1-Methyl-2-imidazolidinone | | 441.2594 |
| 17 | (R)-(+)-4-Hydroxy-2-pyrrolidinone | | 442.2453 |
| 18 | (S)-(−)-4-Hydroxy-2-pyrrolidinone | | 442.2434 |

-continued
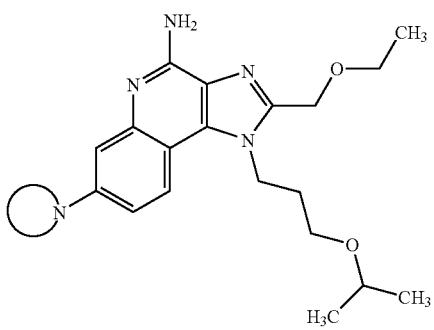
| Example | Reagent | 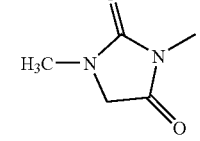 | Measured Mass (M + H) |
|---------|---------|---|---|
| 19 | 1-Methylhydantoin | 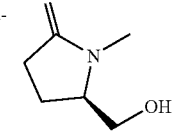 | 455.2408 |
| 20 | (R)-(−)-5-(Hydroxymethyl)-2-pyrrolidinone | 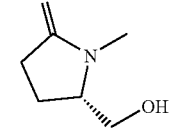 | 456.2632 |
| 21 | L-Pyroglutaminol | 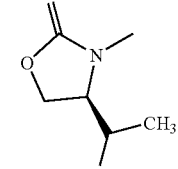 | 456.2587 |
| 22 | (S)-4-Isopropyl-2-oxazolidinone | 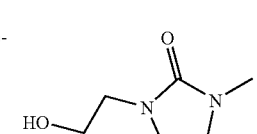 | 470.2766 |
| 23 | 1-(2-Hydroxyethyl)-2-imidazolidinone | 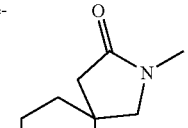 | 471.2715 |
| 24 | 4,4-Pentamethylene-2-pyrrolidinone | | 494.3153 |

-continued

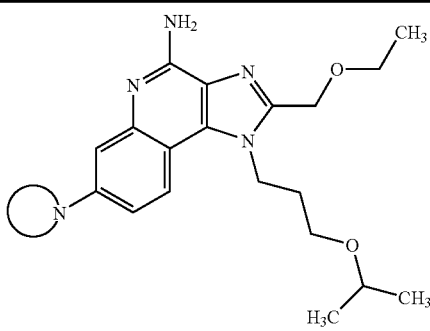

| Example | Reagent | ⟨N— structure | Measured Mass (M + H) |
|---|---|---|---|
| 25 | (R)-(+)-4-Isopropyl-5,5-dimethyl-2-oxazolidinone | 3-methyl-5,5-dimethyl-4-isopropyl-oxazolidinone | 498.3062 |
| 26 | (S)-(−)-4-Isopropyl-5,5-dimethyl-2-oxazolidinone | 3-methyl-5,5-dimethyl-4-isopropyl-oxazolidinone | 498.3059 |
| 27 | (R)-4-Benzyl-2-oxazolidinone | 3-methyl-4-benzyl-oxazolidinone | 518.2771 |
| 28 | (S)-4-Benzyl-2-oxazolidinone | 3-methyl-4-benzyl-oxazolidinone | 518.2739 |
| 29 | (S)-Phenyl superquat | 3-methyl-5,5-dimethyl-4-phenyl-oxazolidinone | 532.2928 |
| 30 | (R)-(+)-4-Benzyl-5,5-dimethyl-2-oxazolidinone | 3-methyl-5,5-dimethyl-4-benzyl-oxazolidinone | 546.3093 |

Examples 31 and 32

Part A

A mixture of 7-bromo-4-chloro-3-nitro[1,5]naphthyridine (92.5 g, 321 mmol) and dichloromethane (1.5 L) was cooled to 10° C. 1-Amino-2-methylpropan-2-ol (63.01 g, 707 mmol) was added dropwise over a period of 30 minutes; during the addition, the reaction temperature did not rise above 13° C. The reaction mixture was allowed to slowly warm to room temperature and stirred overnight. The solvent was removed under reduced pressure, and the solid residue was mixed with water (200 mL). The solid was isolated by filtration, washed with water (2×200 mL), and dried in a vacuum oven overnight at 35° C. to provide 1-[(7-bromo-3-nitro[1,5]naphthyridin-4-yl)amino]-2-methylpropan-2-ol.

Part B

The material from Part A was added to a Parr vessel followed by methanol (1.13 L) and acetonitrile (2.26 L). The vessel was purged with nitrogen, and 5% platinum on carbon (3.4 g), which had been wet with acetonitrile, was added. The reaction mixture was placed under hydrogen pressure (50 psi, $3.4 \times 10^5$ Pa) overnight and filtered. The filtrate was concentrated under reduced pressure to provide 103 g of 1-[(3-amino-7-bromo[1,5]naphthyridin-4-yl)amino]-2-methyl-propan-2-ol as a yellow solid.

Part C

A mixture of 1-[(3-amino-7-bromo[1,5]naphthyridin-4-yl)amino]-2-methylpropan-2-ol (100.0 g, 321.4 mmol) and acetonitrile (1 L) was stirred for five minutes, and ethoxyacetyl chloride (43.3 g, 353.3 mmol) was added. The reaction was stirred overnight at room temperature. The solid product was isolated by filtration and washed with acetonitrile (200 mL) to provide 113 g of N-{7-bromo-4-[(2-hydroxy-2-methylpropyl)amino][1,5]naphthyridin-3-yl}-2-ethoxyacetamide hydrochloride as a yellow solid.

Part D

Potassium carbonate (113 g) water (565 mL) were sequentially added to a solution of N-{7-bromo-4-[(2-hydroxy-2-methylpropyl)amino][1,5]naphthyridin-3-yl}-2-ethoxyacetamide hydrochloride (113 g, 261 mmol) in denatured ethanol (1.695 L), and the resulting mixture was heated at reflux (77° C.) overnight and allowed to cool to room temperature. The ethanol was removed under reduced pressure, and the resulting mixture was filtered to isolate a solid. The solid washed with water (100 mL) and dried over two nights in a vacuum oven at 40° C. to provide 90 g of 1-[7-bromo-2-(ethoxymethyl)-1H-imidazo[4,5-c][1,5]naphthyridin-1-yl]-2-methylpropan-2-ol as a brown solid.

Part E mCPBA (35.5 g of 77% purity, 158 mmol) was added to a stirred solution of 1-[7-bromo-2-(ethoxymethyl)-1H-imidazo[4,5-c][1,5]naphthyridin-1-yl]-2-methylpropan-2-ol (15 g, 0.040 mol) in chloroform (400 mL), and the reaction was stirred at room temperature for 2.5 hours. Concentrated ammonium hydroxide (200 mL) was added, and then p-toluenesulfonyl chloride (18.9 g, 98.9 mmol) was added over a period of five minutes. The reaction mixture was stirred at room temperature for 2.5 hours, and an analysis by LC/MS indicated the presence of starting material. Additional p-toluenesulfonyl chloride (11 g) was added, and the reaction mixture was stirred at room temperature for one hour. An analysis by LC/MS indicated the reaction was still incomplete. Additional ammonium hydroxide (100 mL) and p-toluenesulfonyl chloride (10 g) were added, and the mixture was stirred for 30 minutes at room temperature. The aqueous layer was separated and extracted with dichloromethane (2×300 mL). The combined organic fractions were dried over magnesium sulfate, filtered, and concentrated under reduced pressure. The residue (41.4 g) was purified by chromatography using a Biotage Horizon™ High-Performance Flash Chromatography instrument (65I cartridge, eluting with ethyl acetate: methanol in a gradient from 97:3 to 85:15) to provide 5.96 g of 1-[4-amino-7-bromo-2-(ethoxymethyl)-1H-imidazo[4,5-c][1,5]naphthyridin-1-yl]-2-methylpropan-2-ol as a yellow solid.

Part F

An amide from the table below (1.2 eq) was added to a test tube containing 8 mg (0.4 eq) of copper iodide, 42 mg of potassium phosphate, and a magnetic stir bar. A solution of 1-[4-amino-7-bromo-2-(ethoxymethyl)-1H-imidazo[4,5-c][1,5]naphthyridin-1-yl]-2-methylpropan-2-ol (38 mg, 1.0 eq) in 1,4-dioxane (1.0 mL) was added to the test tube and the test tube was purged with nitrogen. A solution of N,N-dimethylethylenediamine (4.4 µL) in 1,4-dioxane (25 µL) was added to the test tube and the test tube was purged with nitrogen. The test tube was capped and the reaction mixture was stirred at 110° C. for 140 hours.

The reaction mixture was filtered and then concentrated by vacuum centrifugation. The compounds were purified as described in Examples 15-30. The table below shows the amide used for each example, the structure of the resulting compound, and the observed accurate mass for the isolated trifluoroacetate salt.

| Example | Reagent | | Measured Mass (M + H) |
|---|---|---|---|
| 31 | (S)-(−)-4-Hydroxy-2-pyrrolidinone | | 415.2107 |
| 32 | (R)-(−)-5-(Hydroxymethyl)-2-pyrrolidinone | | 429.2255 |

Examples 33-66

Part A

A reaction vessel was charged sequentially with 1-[4-amino-7-bromo-2-(ethoxymethyl)-1H-imidazo[4,5-c]quinolin-1-yl]-2-methylpropan-2-ol (3.9 g, 10 mmol), S(−)-5-hydroxymethyl-2-pyrrolidinone (1.38 g, 12 mmol), copper iodide (0.76 g, 4 mmol), potassium phosphate (4.25 g, 20 mmol), dioxane (60 mL), and trans-1,2-diaminocyclohexane (0.46 g, 4 mmol). The vessel was purged with nitrogen, sealed, and then heated in a sand bath at 100° C. overnight. The vessel was cooled and then S(−)-5-hydroxymethyl-2-pyrrolidinone (1.38 g, 12 mmol), copper iodide (0.76 g, 4 mmol), potassium phosphate (4.25 g, 20 mmol), and trans-1, 2-diaminocyclohexane (0.46 g, 4 mmol) were added and the vessel was purged with nitrogen, sealed, and then heated in a sand bath at 100° C. overnight. The reaction mixture was cooled to ambient temperature and then it was filtered through a layer of CELITE filter aid. The filter cake was rinsed with chloroform and the filtrate was concentrated under reduced pressure to provide an oil. The oil was purified by high performance flash chromatography using a COMBIFLASH system (an automated high-performance flash purification product available from Teledyne Isco, Inc., Lincoln, Nebr., USA) eluting with a gradient of 0 to 13% methanol in dichloromethane containing 1% ammonium hydroxide to provide 1.56 g of a yellow solid. This material was again purified by high performance flash chromatography eluting with a gradient of 4 to 14% CMA in chloroform to provide 1.3 g of 5(S)-1-[4-amino-2-ethoxymethyl-1-(2-hydroxy-2-methyl-propyl)-1H-imidazo[4,5-c]quinolin-7-yl]-5-hydroxymethylpyrrolidin-2-one as a yellow oil.

Part B

A mixture of the material from Part A (1.26 g, 2.93 mmol), triethylamine (488 µL, 3.51 mmol), and dichloromethane (20 mL) was cooled in an ice bath for 5 minutes. Methanesulfonyl chloride (231 µL) was added dropwise. The reaction mixture was stirred at 0° C. for 2 hours. An additional equivalent of triethylamine and methane sulfonyl chloride were added. The reaction mixture was stirred for 2 hours while slowly warming to ambient temperature. The reaction mixture was quenched with water (about 1 mL) and then concentrated under reduced pressure to provide 3.0 g of crude {(2S)-1-[4-amino-2-ethoxymethyl-1-(2-hydroxy-2-methylpropyl)-1H-imidazo[4,5-c]quinolin-7-yl]-5-oxopyrrolidin-2-yl}methyl methanesulfonate.

Part C

A reagent from the table below (3.0 eq) was added to a test tube containing a solution of material from Part B (51 mg, 1.0 eq) in N,N-dimethylacetamide (1.0 mL). Potassium tert-butoxide (200 µL of 1 M in tetrahydrofuran) was added. The tubes for Examples 34-60 were heated at 70° C. overnight and those for Examples 61-67 were heated at 90° C. overnight. The solvent was removed by vacuum centrifugation and the compounds were purified as described in Examples 15-30. The table below shows the reagent used for each example, the structure of the resulting compound, and the observed accurate mass for the isolated trifluoroacetate salt.

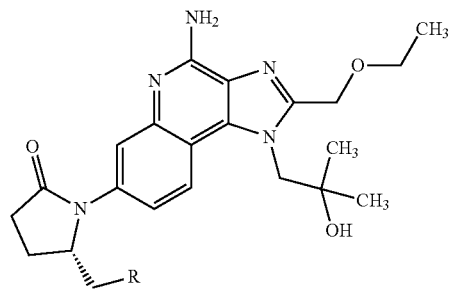

| Example | Reagent | R | Measured Mass (M + H) |
|---|---|---|---|
| 33 | Pyrrolidine | | 481.2959 |
| 34 | Methyl-N-propylamine | | 483.3098 |
| 35 | Piperidine | | 495.3090 |
| 36 | (R)-3-Hydroxypyrrolidine | | 497.2879 |
| 37 | Morpholine | | 497.2883 |

-continued

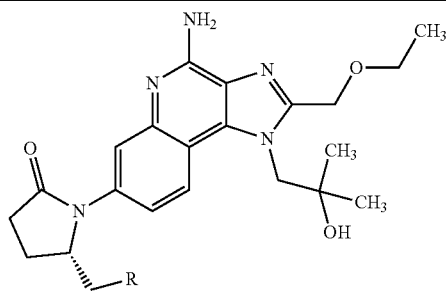

| Example | Reagent | R | Measured Mass (M + H) |
|---|---|---|---|
| 38 | 3-Methylpiperidine | 1-methyl-3-methylpiperidine | 509.3248 |
| 39 | 4-Methylpiperidine | 1-methyl-4-methylpiperidine | 509.3271 |
| 40 | 2-Methylpiperidine | 1-methyl-2-methylpiperidine | 509.3259 |
| 41 | 1-Methylpiperazine | 4-methylpiperazin-1-yl | 510.3237 |
| 42 | 3-Hydroxypiperidine | 1-methyl-3-hydroxypiperidine | 511.3053 |
| 43 | L-Prolinol | (S)-1-methyl-2-(hydroxymethyl)pyrrolidine | 511.3016 |
| 44 | 4-Hydroxypiperidine | 1-methyl-4-hydroxypiperidine | 511.3048 |
| 45 | N-Methylpentylamine | N-methyl-N-pentylamine | 511.3370 |
| 46 | 3-(Dimethylamino)pyrrolidine | 1-methyl-3-(dimethylamino)pyrrolidine | 524.3369 |

-continued
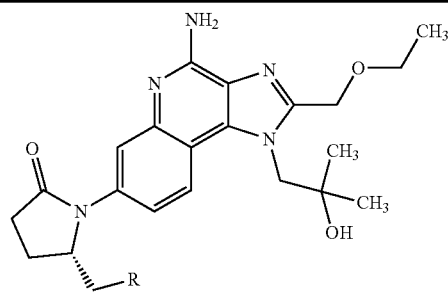
| Example | Reagent | R | Measured Mass (M + H) |
|---|---|---|---|
| 47 | N-Ethylpiperazine | | 524.3355 |
| 48 | N-Methylhomopiperazine | | 524.3365 |
| 49 | 3-(Hydroxymethyl)piperidine | | 525.3239 |
| 50 | 4-(Hydroxymethyl)piperidine | | 525.3190 |
| 51 | Isonipecotamide | | 538.3169 |
| 52 | (3S)-(−)-3-Acetamidopyrrolidine | | 538.3168 |
| 53 | 1-Acetylpiperazine | | 538.3150 |
| 54 | 2-Piperidineethanol | | 539.3353 |
| 55 | 4-Piperidineethanol | | 539.3375 |

-continued
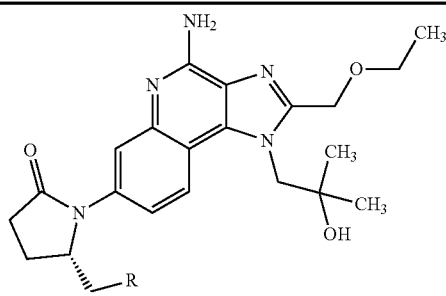
| Example | Reagent | R | Measured Mass (M + H) |
|---|---|---|---|
| 56 | N-(2-Hydroxyethyl)piperazine | | 540.3286 |
| 57 | 1,2,3,4-Tetrahydroisoquinoline | | 543.3088 |
| 58 | Methyl isonipecotate | | 553.3162 |
| 59 | 1-(2-Methpxyethyl)piperazine | | 554.3436 |
| 60 | 4-Cyanophenol | | 529.2554 |
| 61 | 4-Methoxyphenol | | 534.2681 |
| 62 | Guaiacol | | 534.2712 |
| 63 | 3-Chlorophenol | | 538.2236 |
| 64 | 4-Chlorophenol | | 538.2228 |

-continued

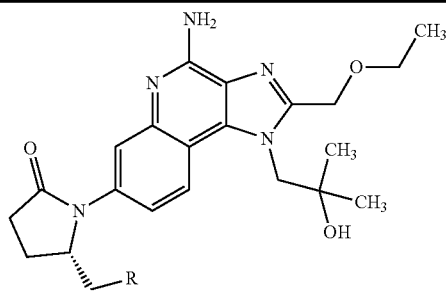

| Example | Reagent | R | Measured Mass (M + H) |
|---|---|---|---|
| 65 | 3-Dimethylaminophenol | —O—C₆H₄—N(CH₃)₂ (3-substituted) | 547.3030 |
| 66 | 4-(Methylmercapto)phenol | —O—C₆H₄—S—CH₃ (4-substituted) | 550.2490 |

Examples 67 and 68

Part A

1-[4-Amino-7-bromo-2-(ethoxymethyl)-1H-imidazo[4,5-c]quinolin-1-yl]-2-methylpropan-2-ol (3.9 g, 10 mmol) was reacted with R(−)-5-hydroxymethyl-2-pyrrolidinone (1.38 g, 12 mmol) according to the method of Part A of Examples 34-67. The crude product was purified by high performance flash chromatography using a COMBIFLASH system eluting with a gradient of 0 to 13% methanol in dichloromethane containing 1% ammonium hydroxide to provide 1.28 g of (5R)-1-[4-amino-2-ethoxymethyl-1-(2-hydroxy-2-methylpropyl)-1H-imidazo[4,5-c]quinolin-7-yl]-5-hydroxymethylpyrrolidin-2-one as a yellow solid.

Part B

A mixture of the material from Part A (1.26 g, 2.95 mmol), triethylamine (493 μL, 3.54 mmol), and dichloromethane (20 mL) was cooled in an ice bath for 5 minutes. Methanesulfonyl chloride (233 μL, 2.95 mmol) was added dropwise. The reaction mixture was stirred at 0° C. for 2 hours. Additional methanesulfonyl chloride (30 μL) was added and the reaction mixture was stirred at 0° C. for an additional 30 minutes. The reaction mixture was concentrated under reduced pressure. The residue was diluted with diethyl ether and the mixture was concentrated under reduced pressure to provide 2.2 g of crude {(2R)-1-[4-amino-2-ethoxymethyl-1-(2-hydroxy-2-methylpropyl)-1H-imidazo[4,5-c]quinolin-7-yl]-5-oxopyrrolidin-2-yl}methyl methanesulfonate.

Part C

A reagent from the table below (3.0 eq) was added to a test tube containing a solution of material from Part B (55 mg, 1.0 eq) in N,N-dimethylacetamide (1.0 mL) and potassium tert-butoxide (200 μL of 1 M in tetrahydrofuran). The tube for Example 68 was heated at 50° C. for 6 hours and the tube for Example 69 was heated at 70° C. for 6 hours overnight. The solvent was removed by vacuum centrifugation and the compounds were purified as described in Examples 15-30. The table below shows the reagent used for each example, the structure of the resulting compound, and the observed accurate mass for the isolated trifluoroacetate salt.

| Example | Reagent | R | Measured Mass (M + H) |
|---|---|---|---|
| 67 | 4-Hydroxypiperidine | | 511.3026 |
| 68 | Phenol | —O—C₆H₅ | 504.2630 |

Example 69

1-[4-Amino-2-(hydroxymethyl)-1-(2-methylpropyl)-1H-imidazo[4,5-c][1,5]naphthyridin-7-yl]pyrrolidin-2-one

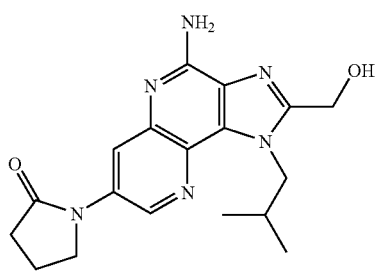

1-[4-Amino-2-(ethoxymethyl)-1-(2-methylpropyl)-1H-imidazo[4,5-c]-1,5-naphthyridin-7-yl]pyrrolidin-2-one (0.150 g, 0.39 mmol) from Example 13 was dissolved in dichloromethane (5 mL) and cooled with an ice bath. Boron tribromide (0.5 mL of a 1.0 M solution in dichloromethane) was added dropwise over 1 minute. The resulting slurry was stirred for 16 hours. The reaction mixture was acidified with 6 N hydrochloric acid (3 mL). The mixture was stirred until all of the solids dissolved. The biphasic mixture was made basic with 50% aqueous sodium hydroxide (~6 mL). The layers were separated and the aqueous fraction was extracted with dichloromethane, followed by extraction with a 10% methanol in dichloromethane solution. The organic fractions were combined and concentrated under vacuum. The residue was purified by HPFC eluting with a linear gradient of 2-30% CMA in chloroform. Recrystallization from acetonitrile afforded 1-[4-amino-2-(hydroxymethyl)-1-(2-methylpropyl)-1H-imidazo[4,5-c][1,5]naphthyridin-7-yl]pyrrolidin-2-one as 0.034 g of a white powder, m.p. 233-235° C.

$^1$H NMR (300 MHz, DMSO-$d_6$) δ 8.93 (d, J=2.4 Hz, 1H), 8.10 (d, J=2.4 Hz, 1H), 6.84 (s, 2H), 5.66 (t, J=5.7 Hz, 1H), 4.77 (d, J=5.7 Hz, 2H), 4.69 (d, J=7.5 Hz, 2H), 3.98 (t, J=7.0 Hz, 2H), 2.55 (t, J=8.0 Hz, 2H), 2.46-2.34 (m, 1H), 2.13 (quintet, J=7.5 Hz, 2H), 0.90 (d, J=6.7 Hz, 6H).

$^{13}$C NMR (125 MHz, DMSO-$d_6$) δ 174.3, 152.7, 152.6, 140.3, 135.6, 134.6, 132.7, 129.9, 127.9, 121.2, 56.2, 51.8, 47.7, 32.0, 29.1, 19.4, 17.6.

MS(ESI) m/z 355.1898 (355.1882 calcd. for $C_{18}H_{22}N_6O_2$, M+H);

Anal. Calcd. for $C_{23}H_{31}N_5O_3 \cdot 2.25H_2O$: % C, 54.74; % H, 6.76; % N, 21.28. Found: % C, 54.68; % H, 6.60; % N, 20.91.

Exemplary Compounds

Certain exemplary compounds, including some of those described above in the Examples, have the following Formulas (IIb and IIIa) wherein $R_1$, $R_2$, and

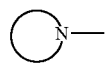

are defined immediately below in the table. In this table, for each ring system (Formula IIb or Formula IIIa), each row represents one specific compound.

| $R_1$ | $R_2$ | |
|---|---|---|
| 2-hydroxy-2-methylpropyl | ethyl | pyrrolidin-2-one |
| 2-hydroxy-2-methylpropyl | ethyl | oxazolidin-2-one |
| 2-hydroxy-2-methylpropyl | ethyl | 5-(hydroxymethyl)oxazolidin-2-one |

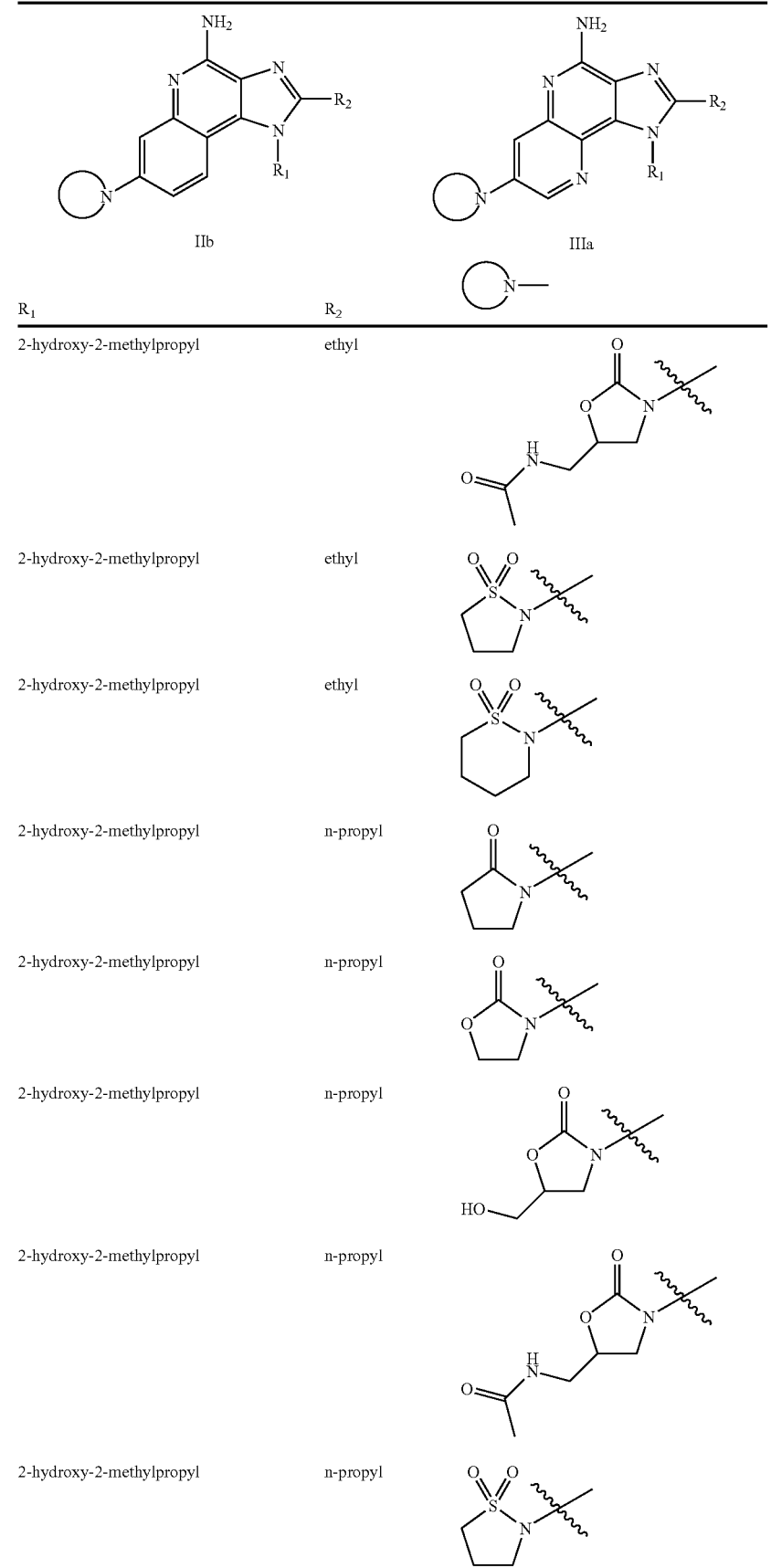

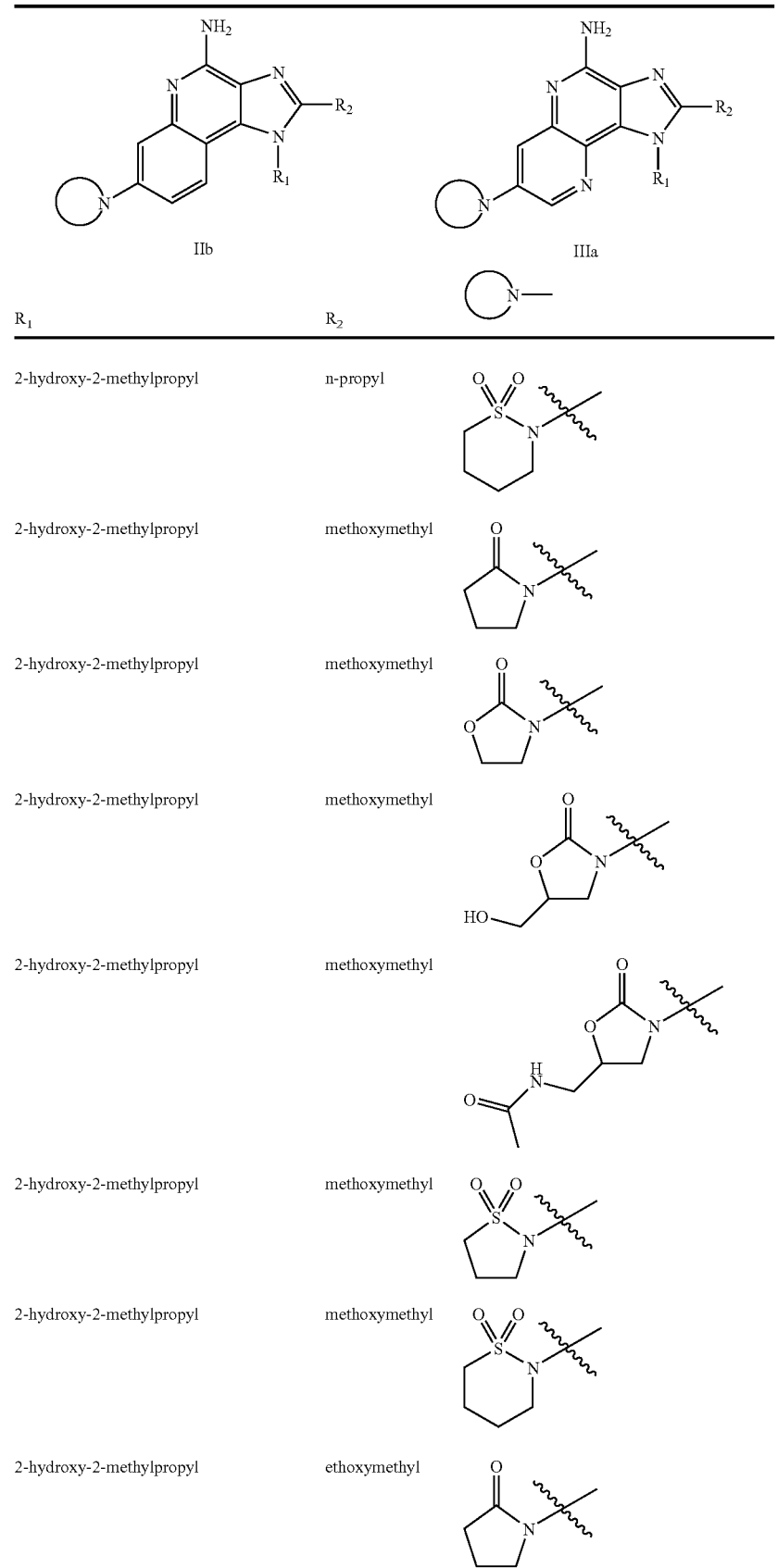

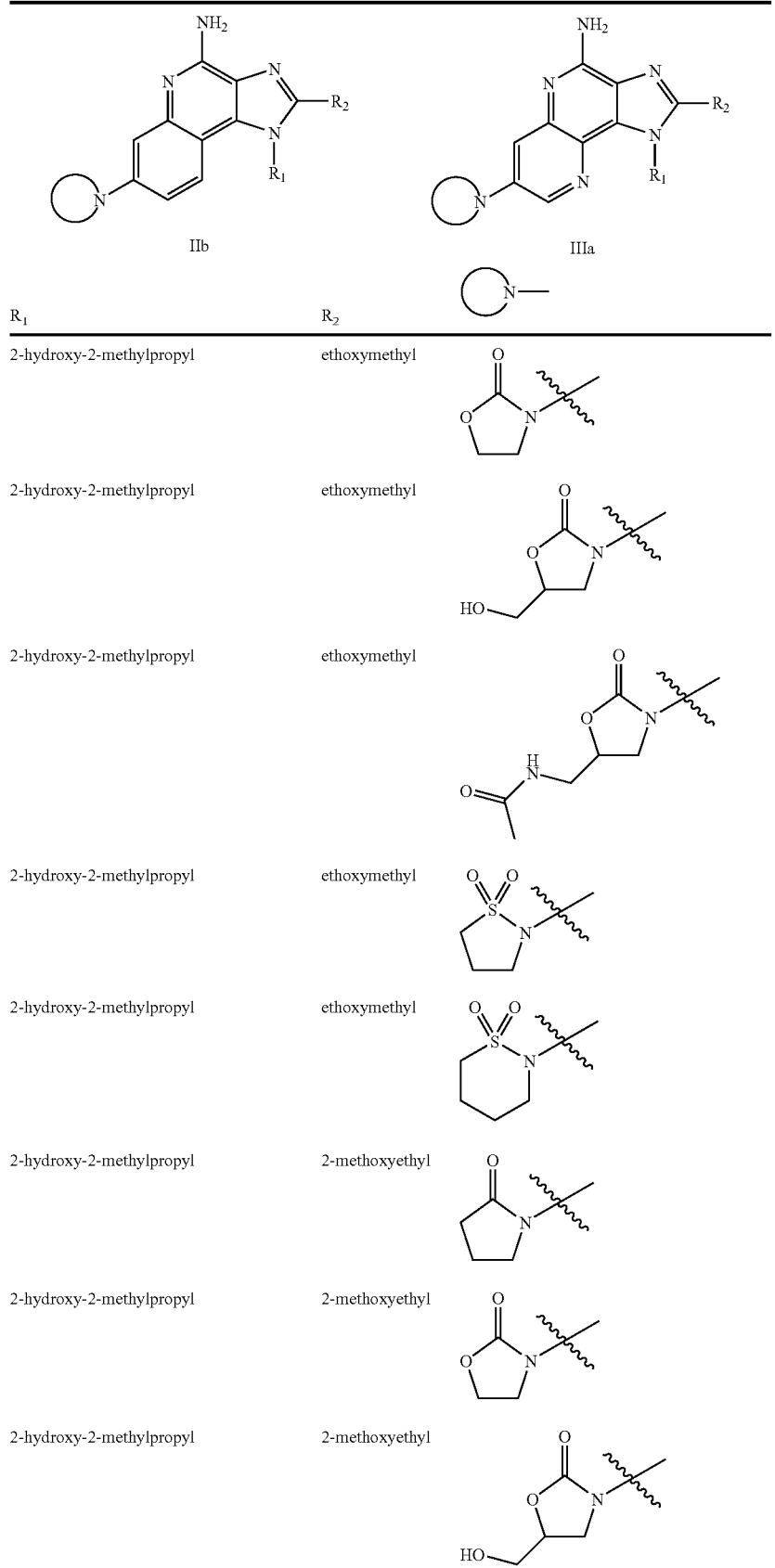

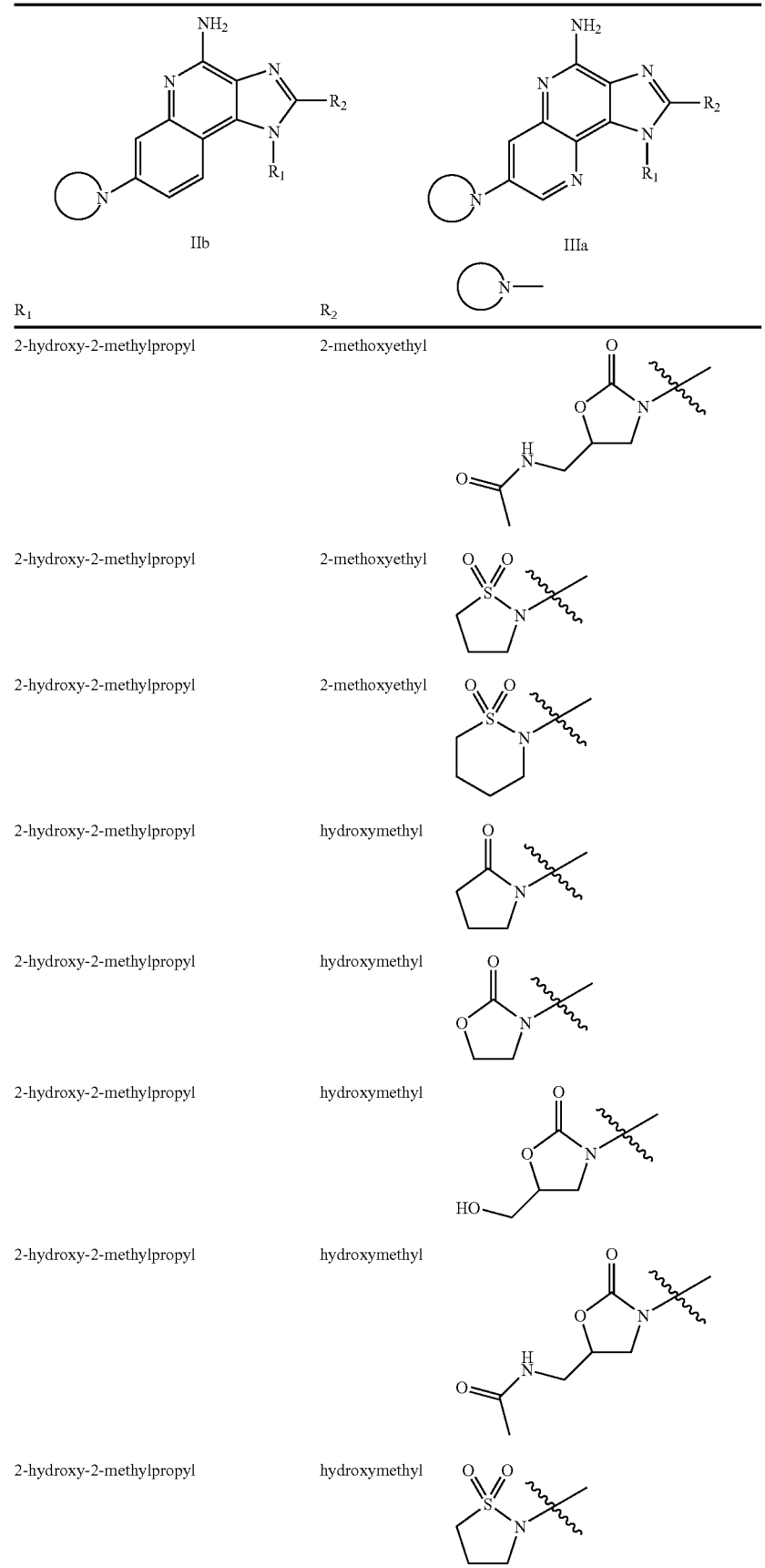

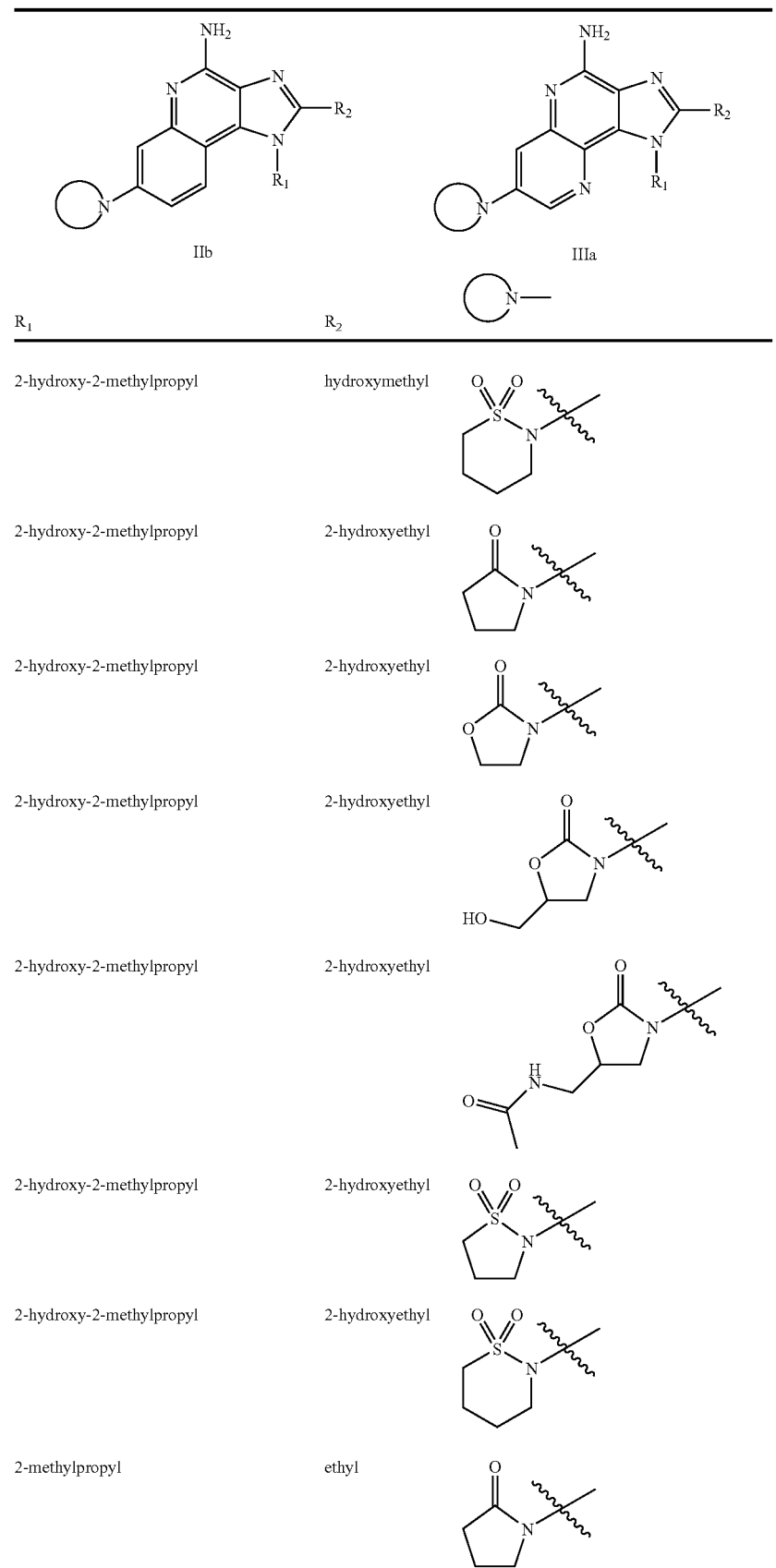

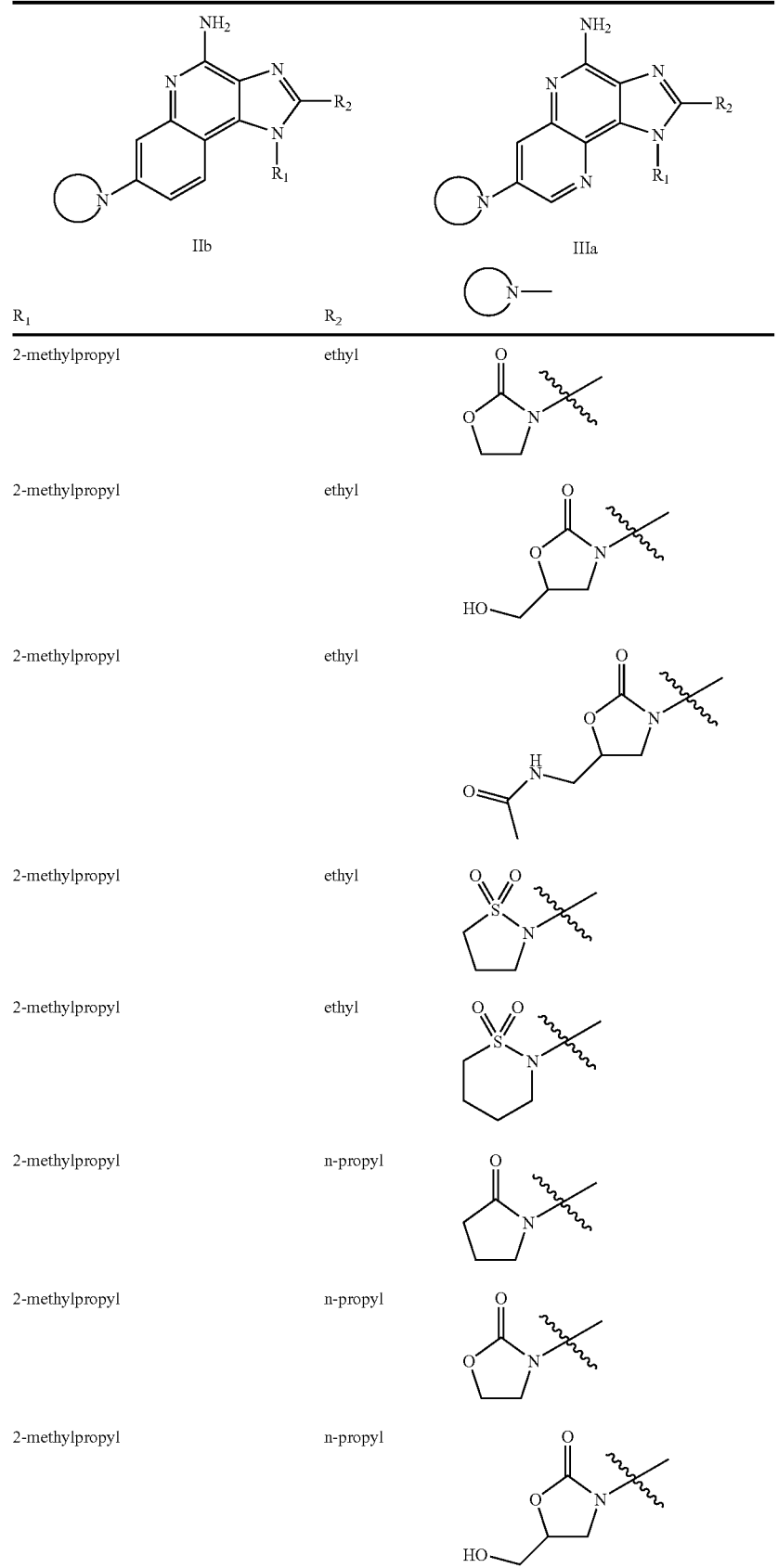

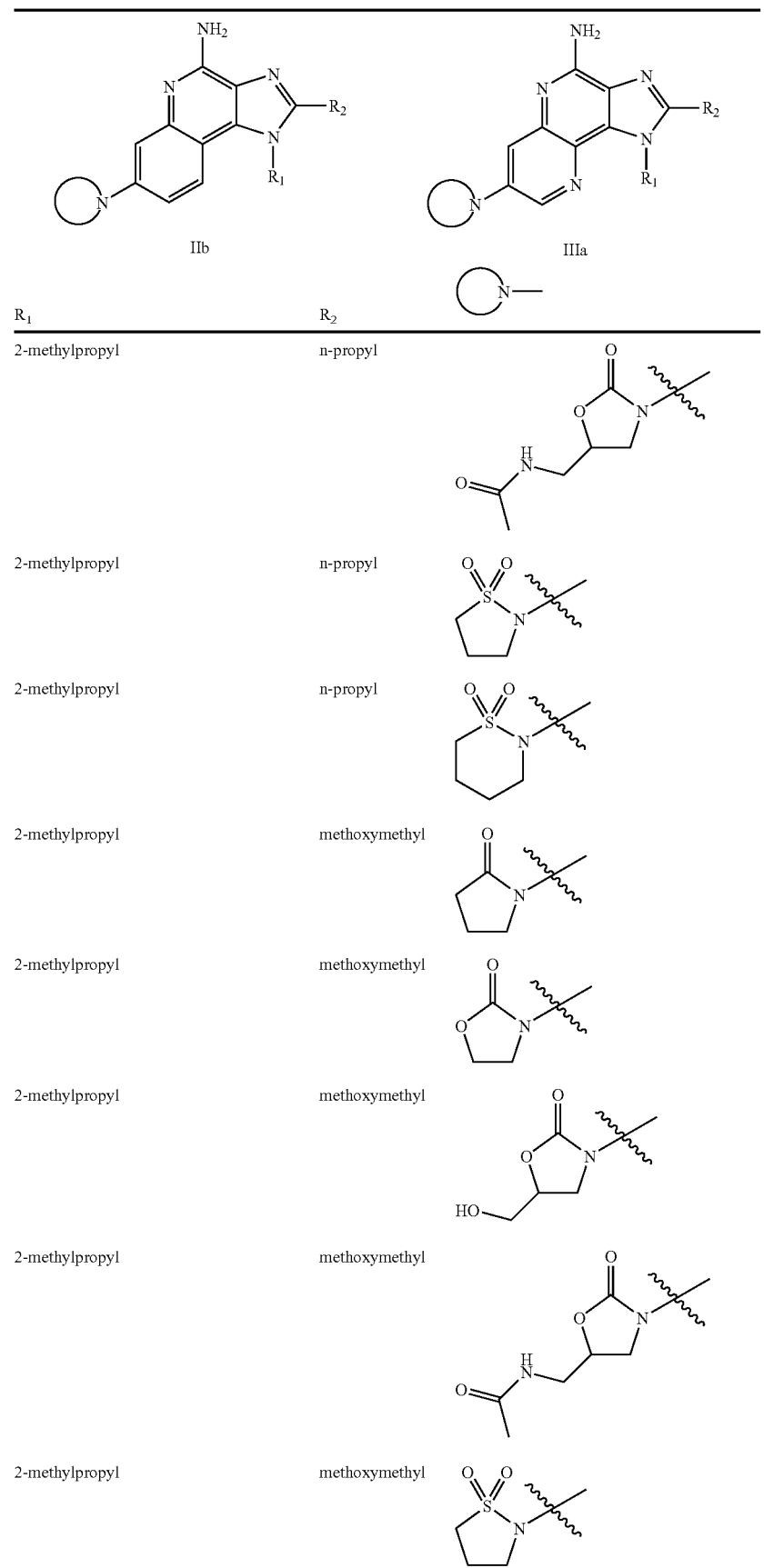

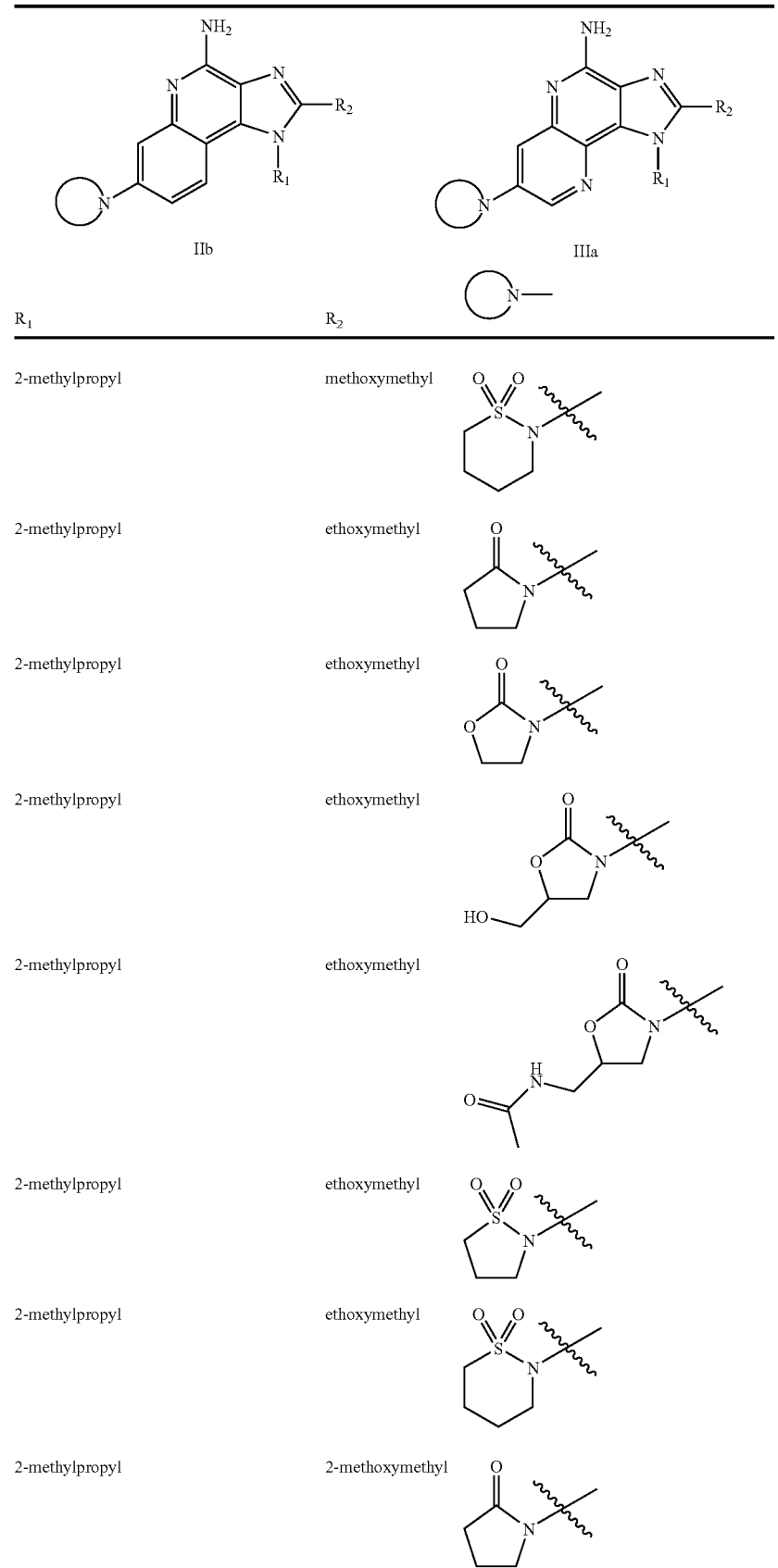

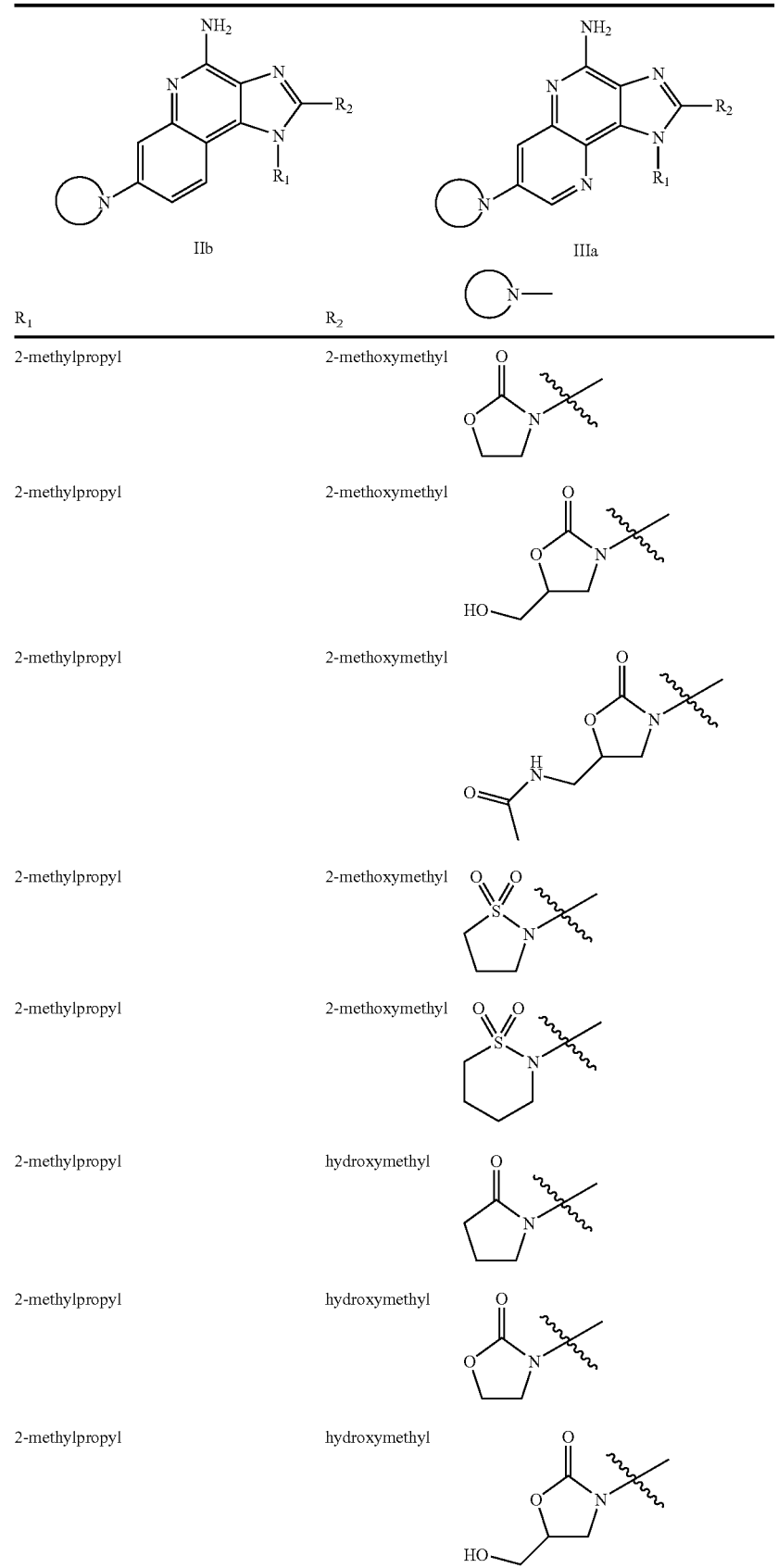

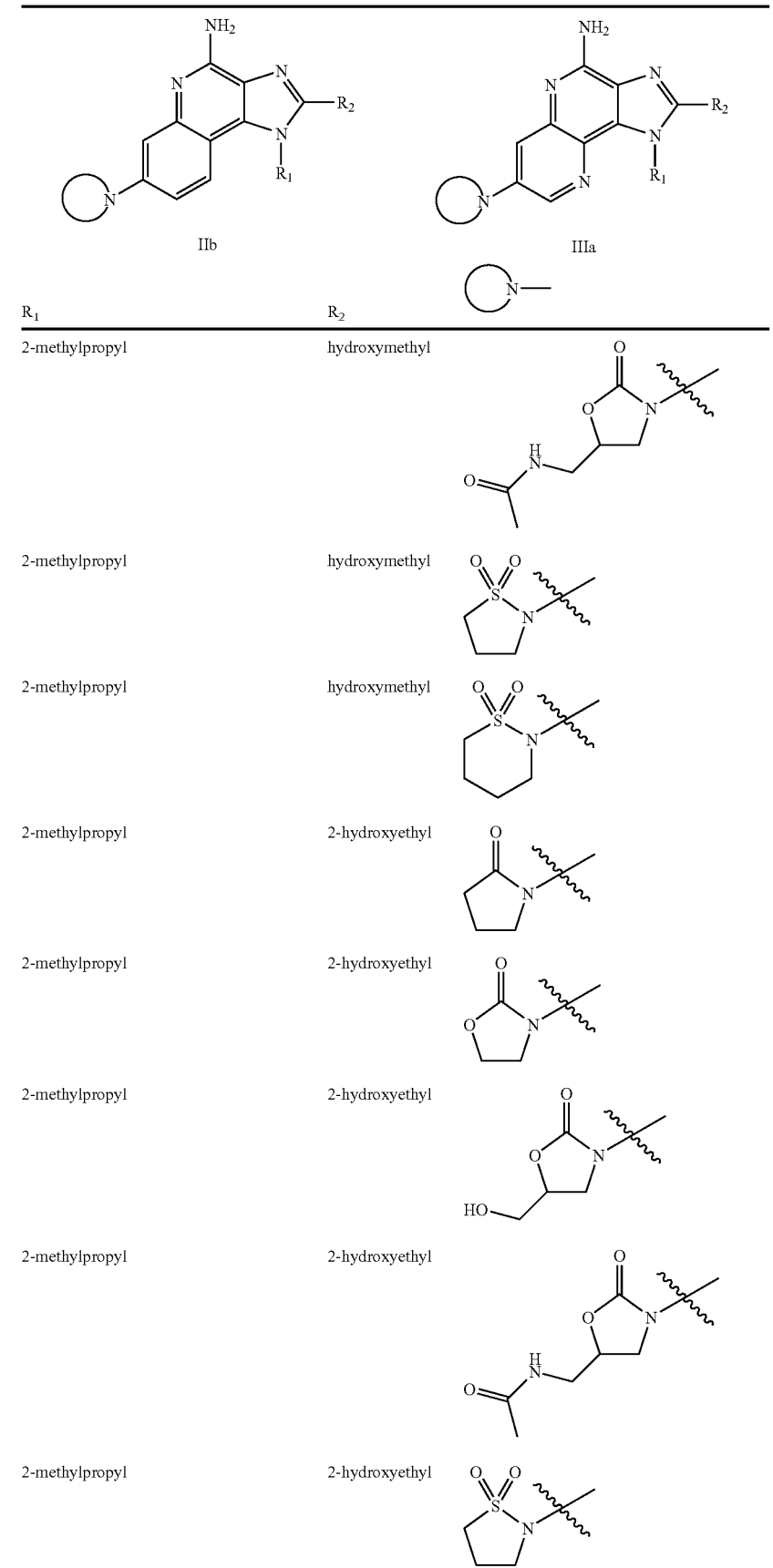

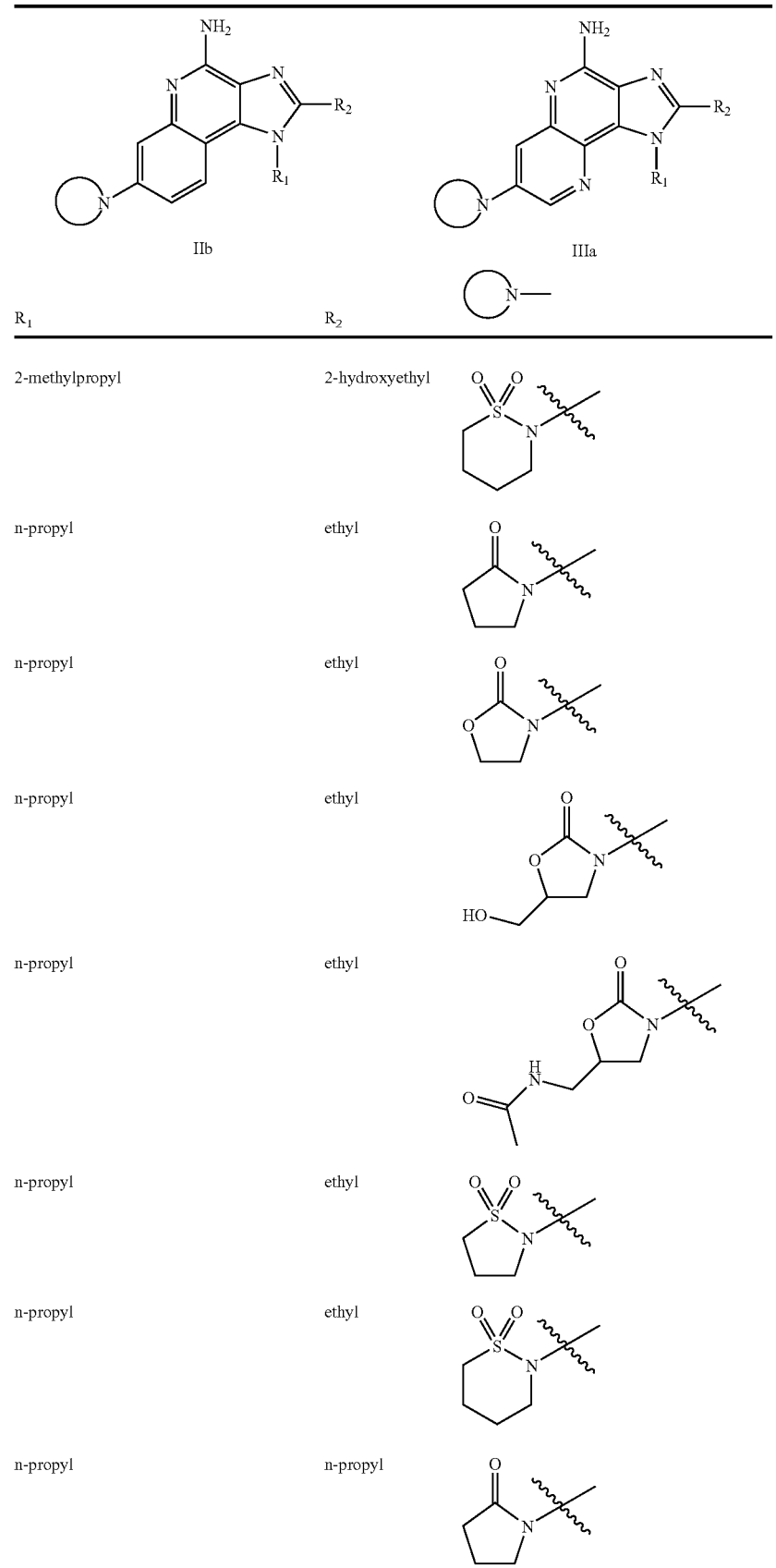

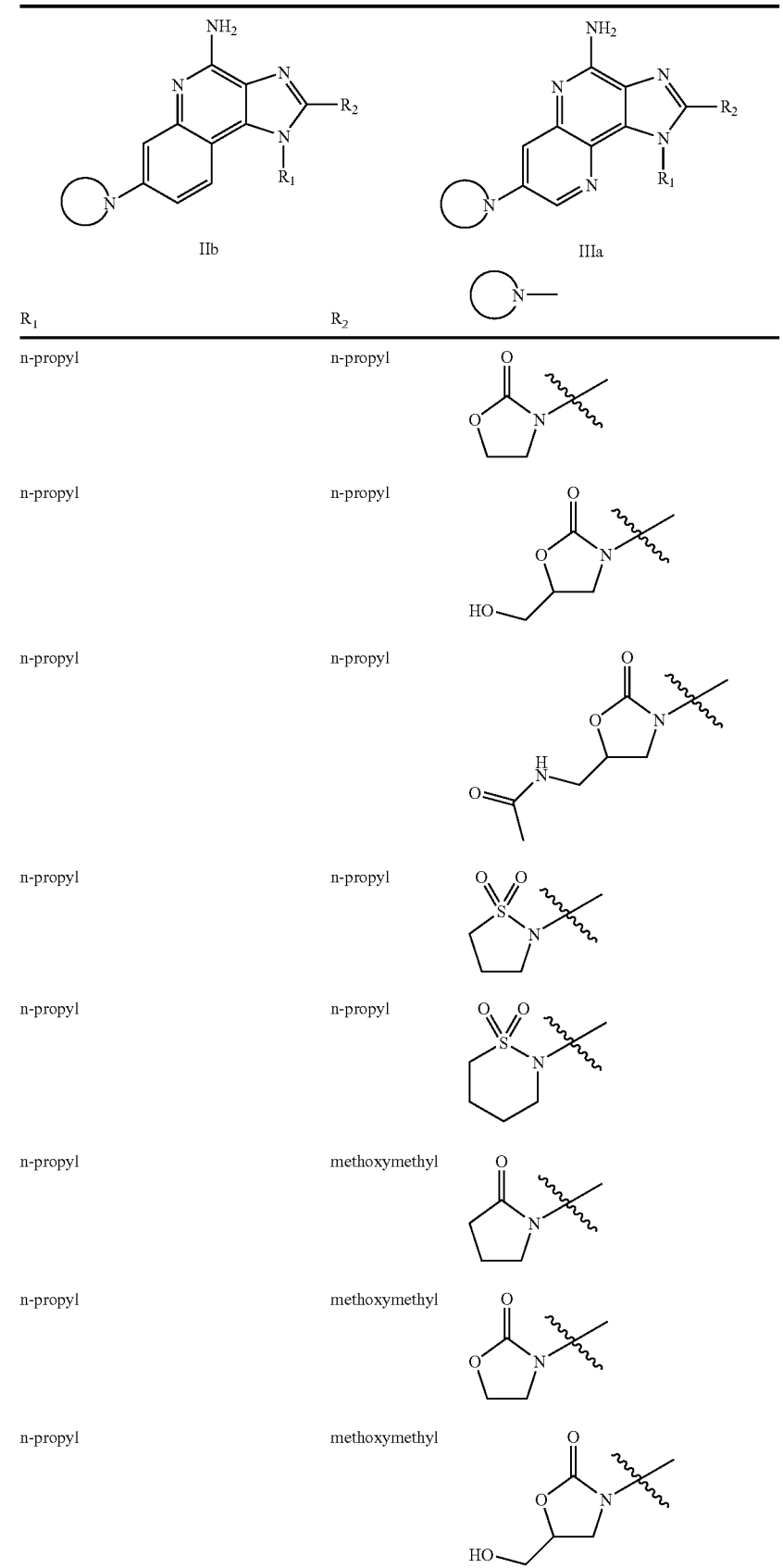

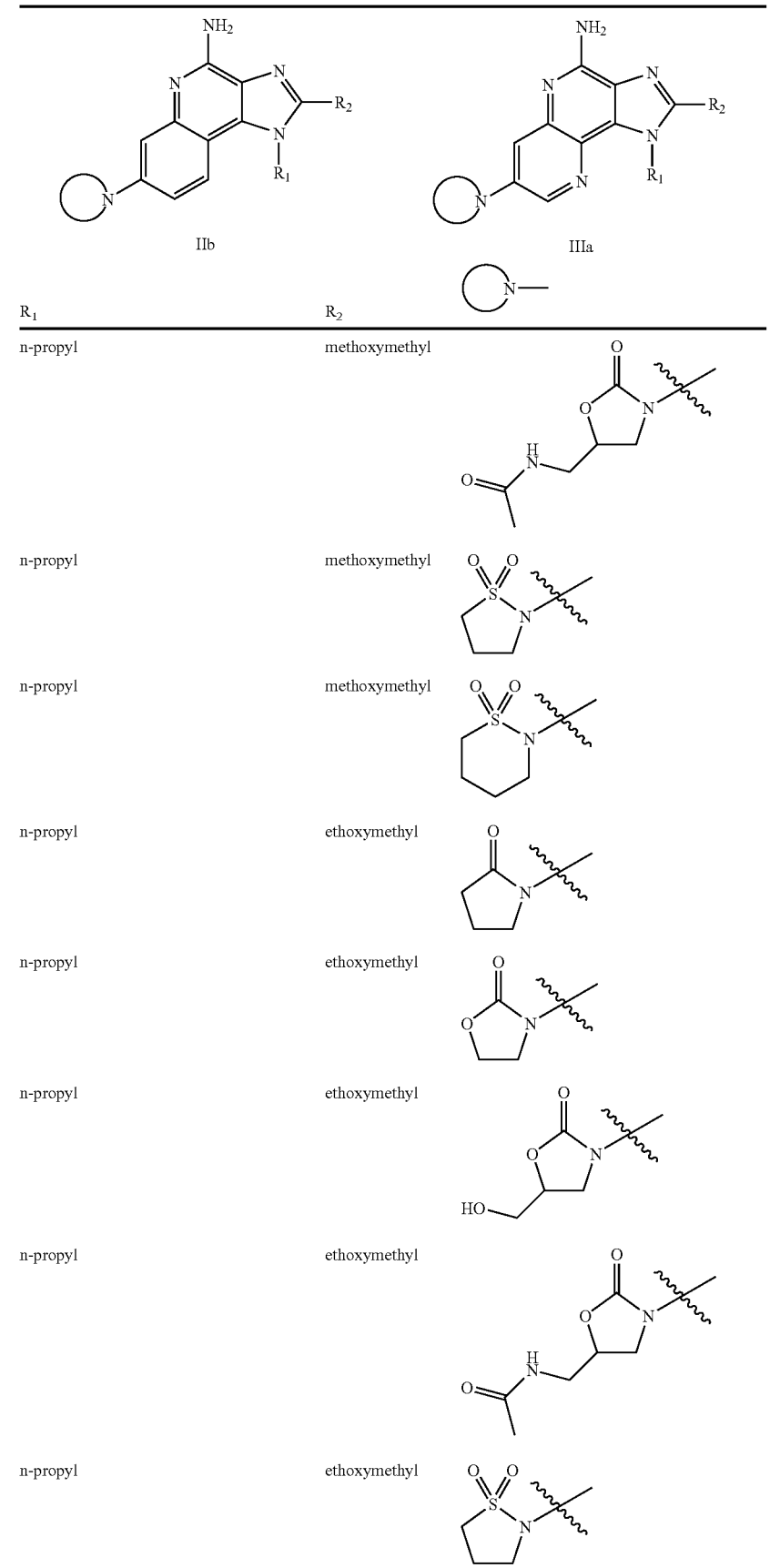

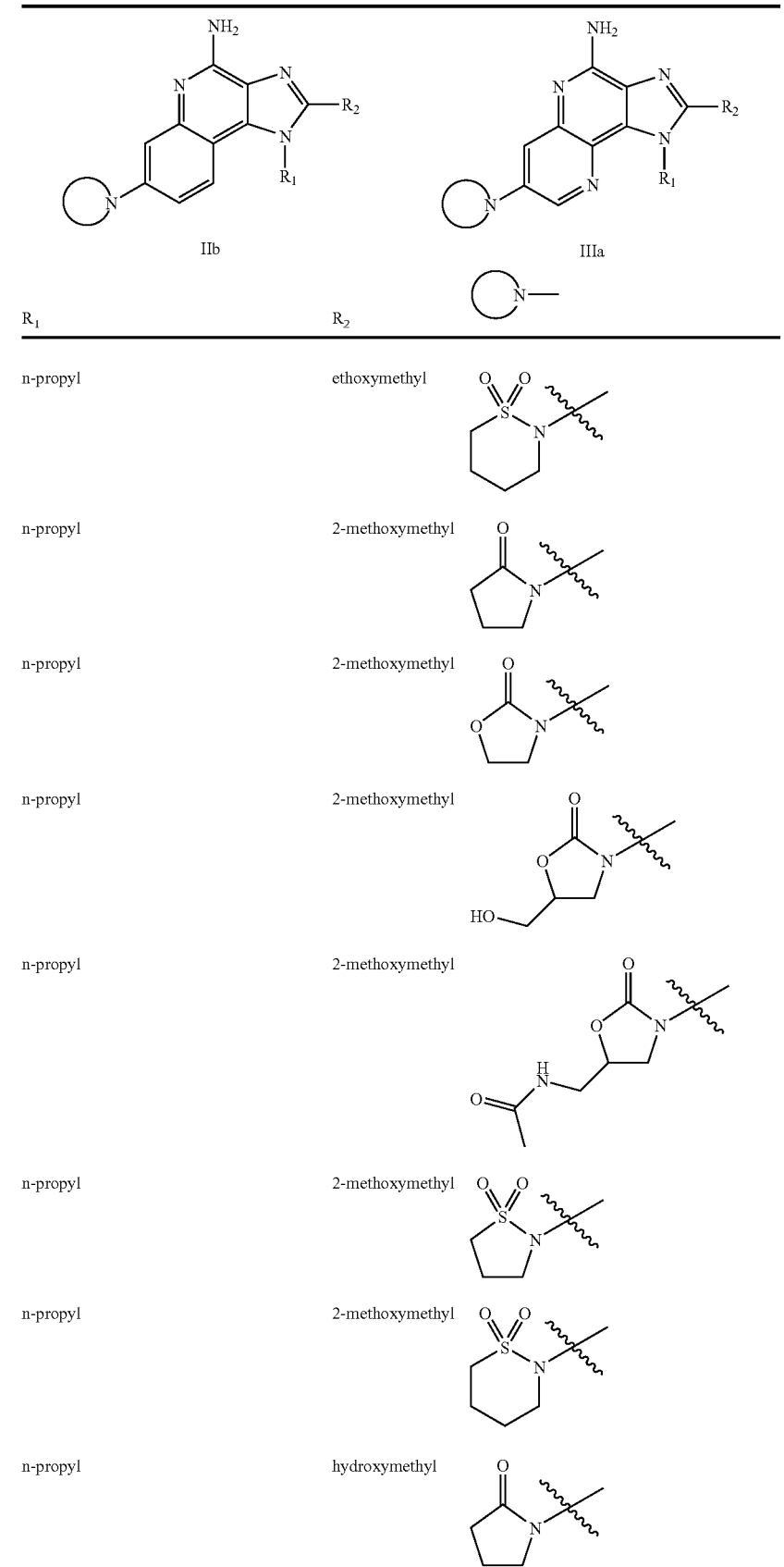

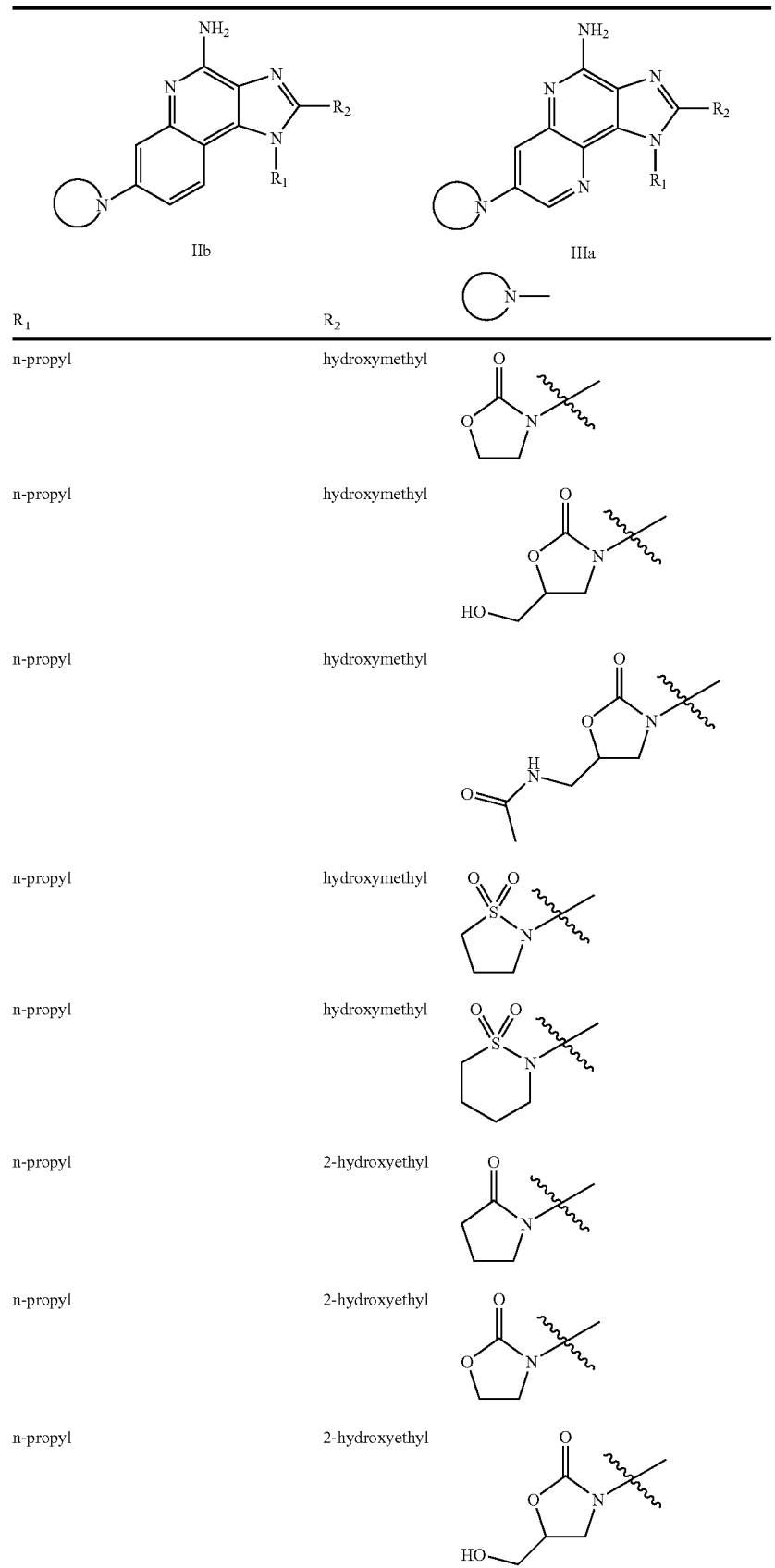

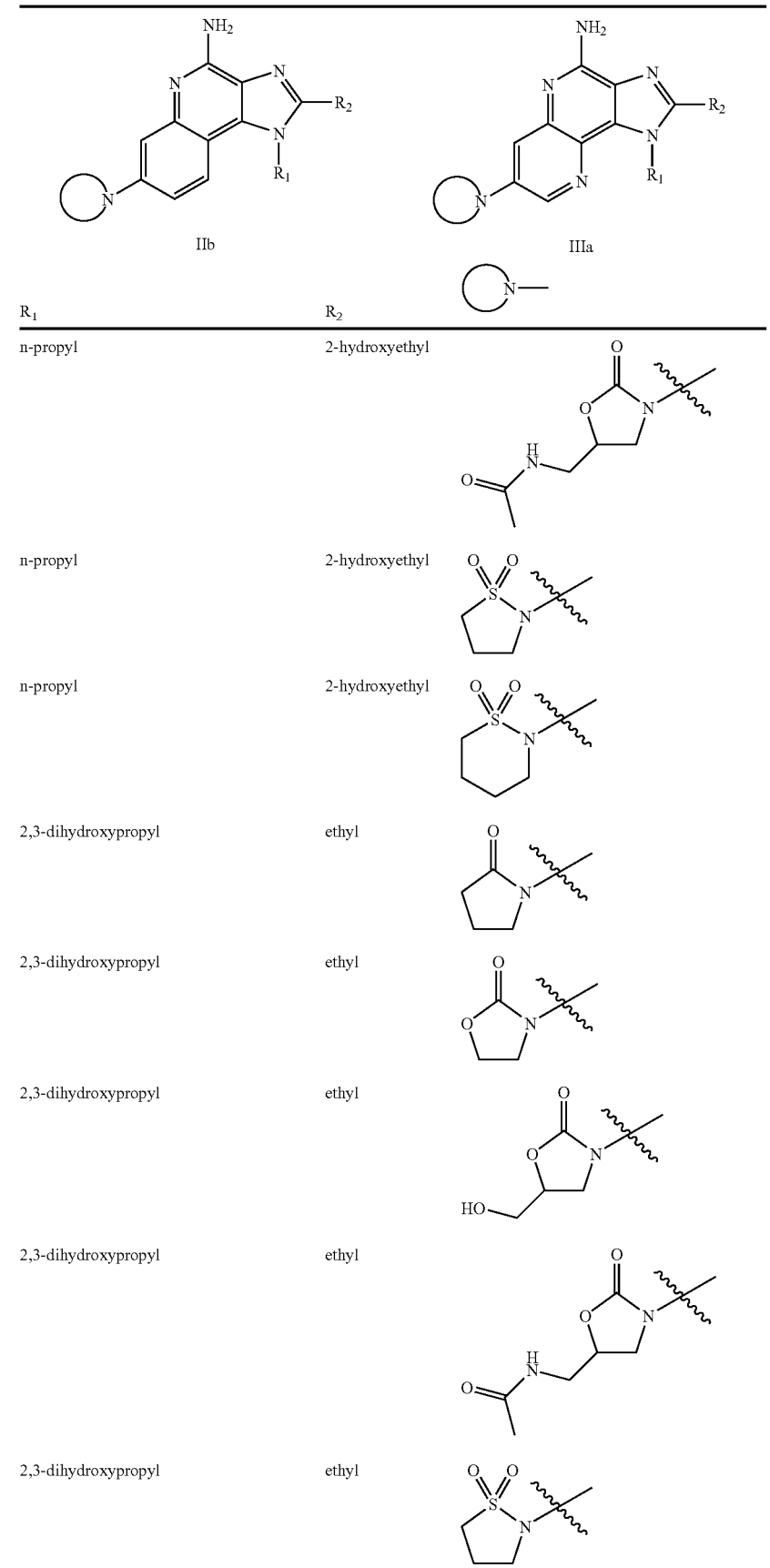

-continued

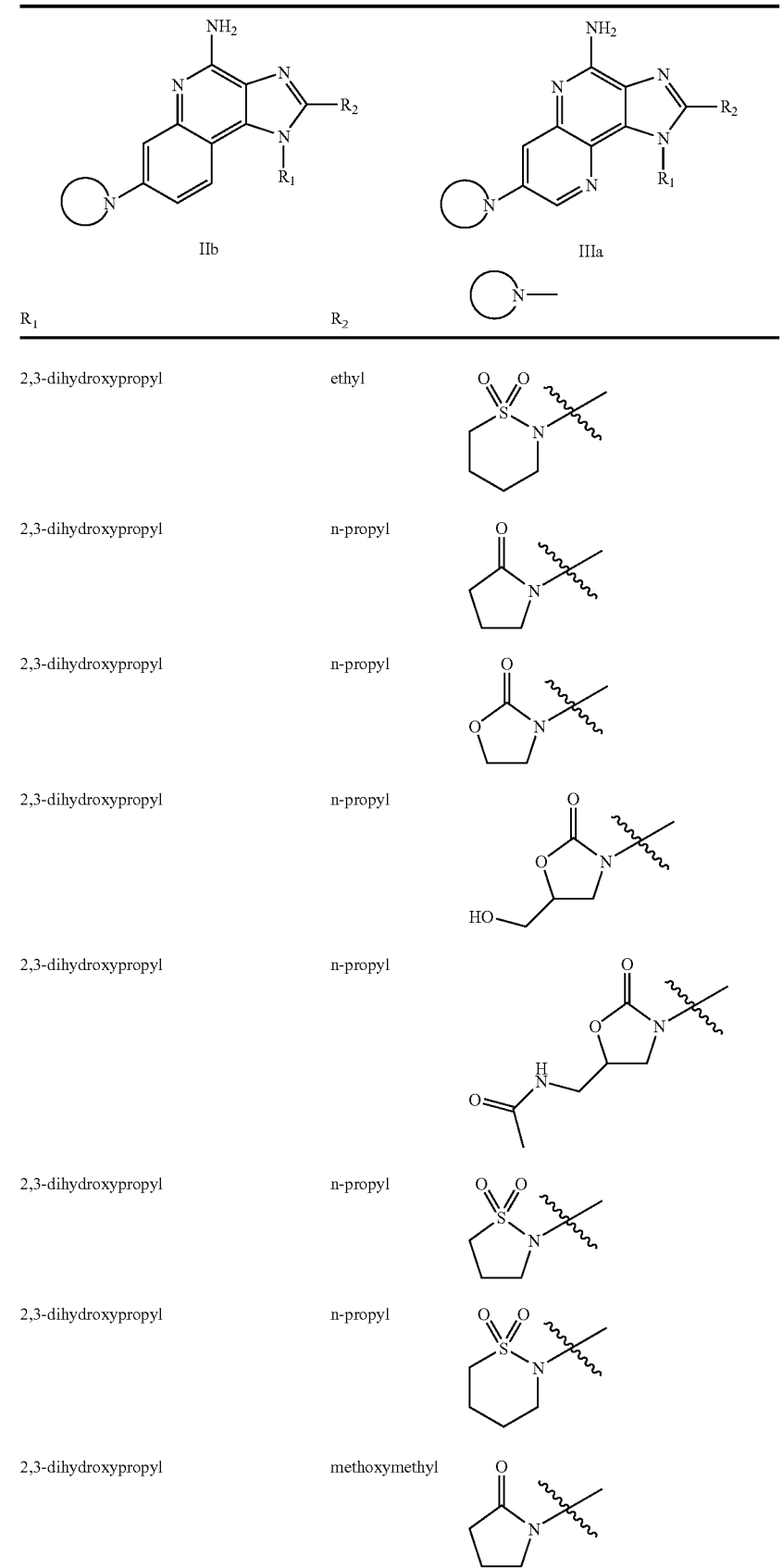

| R₁ | R₂ | |
|---|---|---|
| 2,3-dihydroxypropyl | ethyl | (1,2-thiazinane 1,1-dioxide) |
| 2,3-dihydroxypropyl | n-propyl | (2-pyrrolidinone) |
| 2,3-dihydroxypropyl | n-propyl | (oxazolidin-2-one) |
| 2,3-dihydroxypropyl | n-propyl | (5-(hydroxymethyl)oxazolidin-2-one) |
| 2,3-dihydroxypropyl | n-propyl | (5-(acetamidomethyl)oxazolidin-2-one) |
| 2,3-dihydroxypropyl | n-propyl | (isothiazolidine 1,1-dioxide) |
| 2,3-dihydroxypropyl | n-propyl | (1,2-thiazinane 1,1-dioxide) |
| 2,3-dihydroxypropyl | methoxymethyl | (2-pyrrolidinone) |

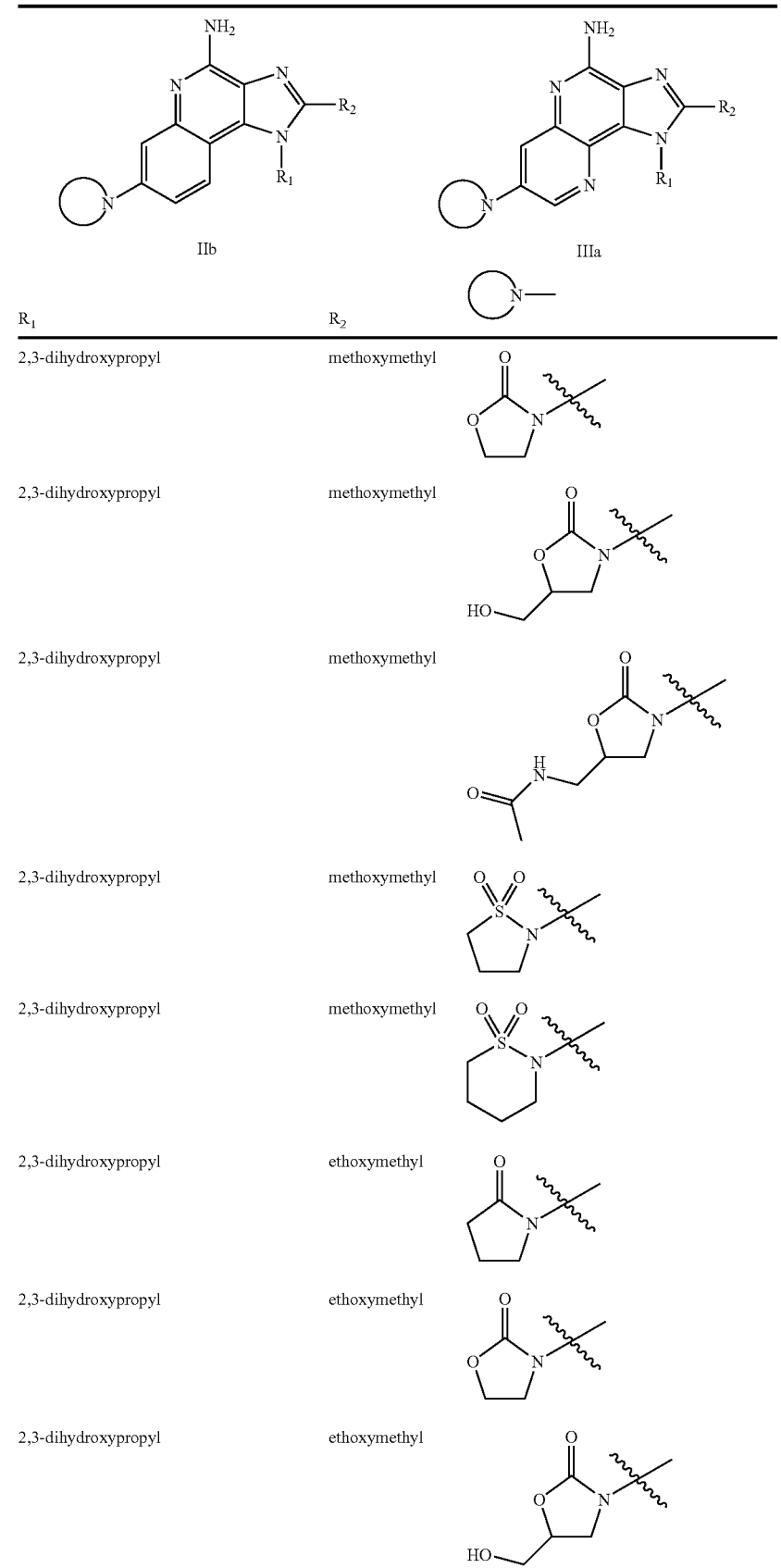

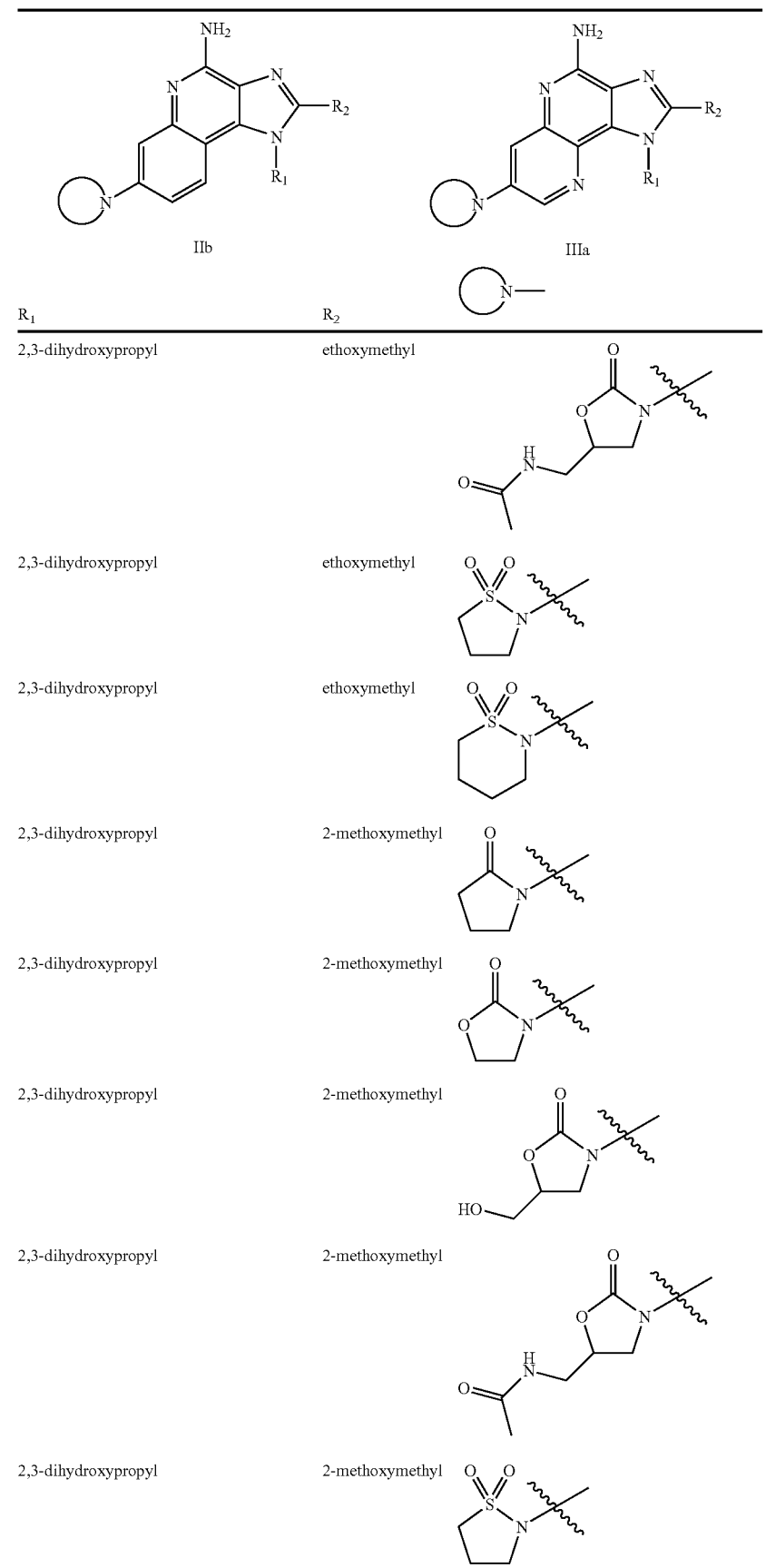

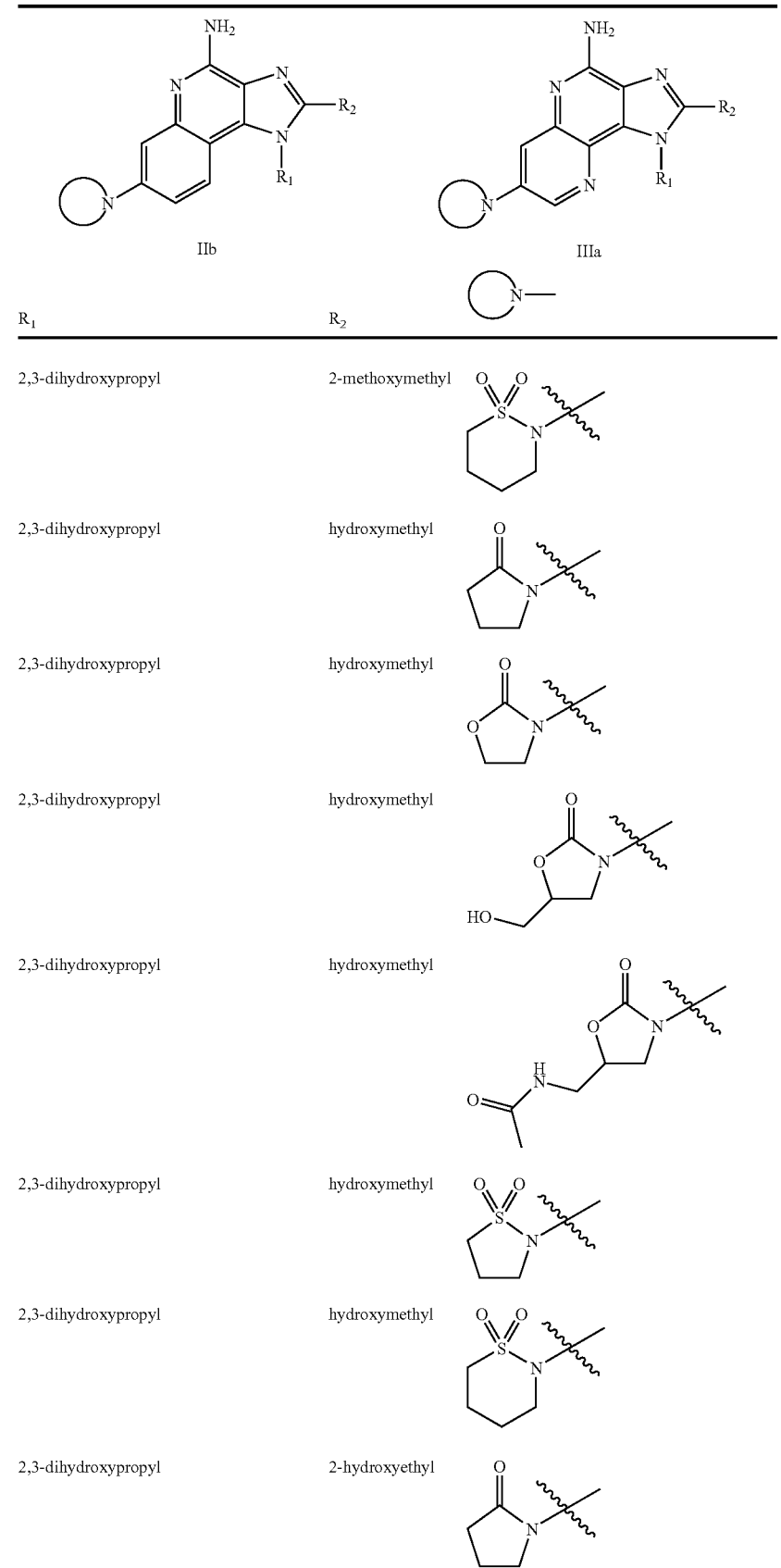

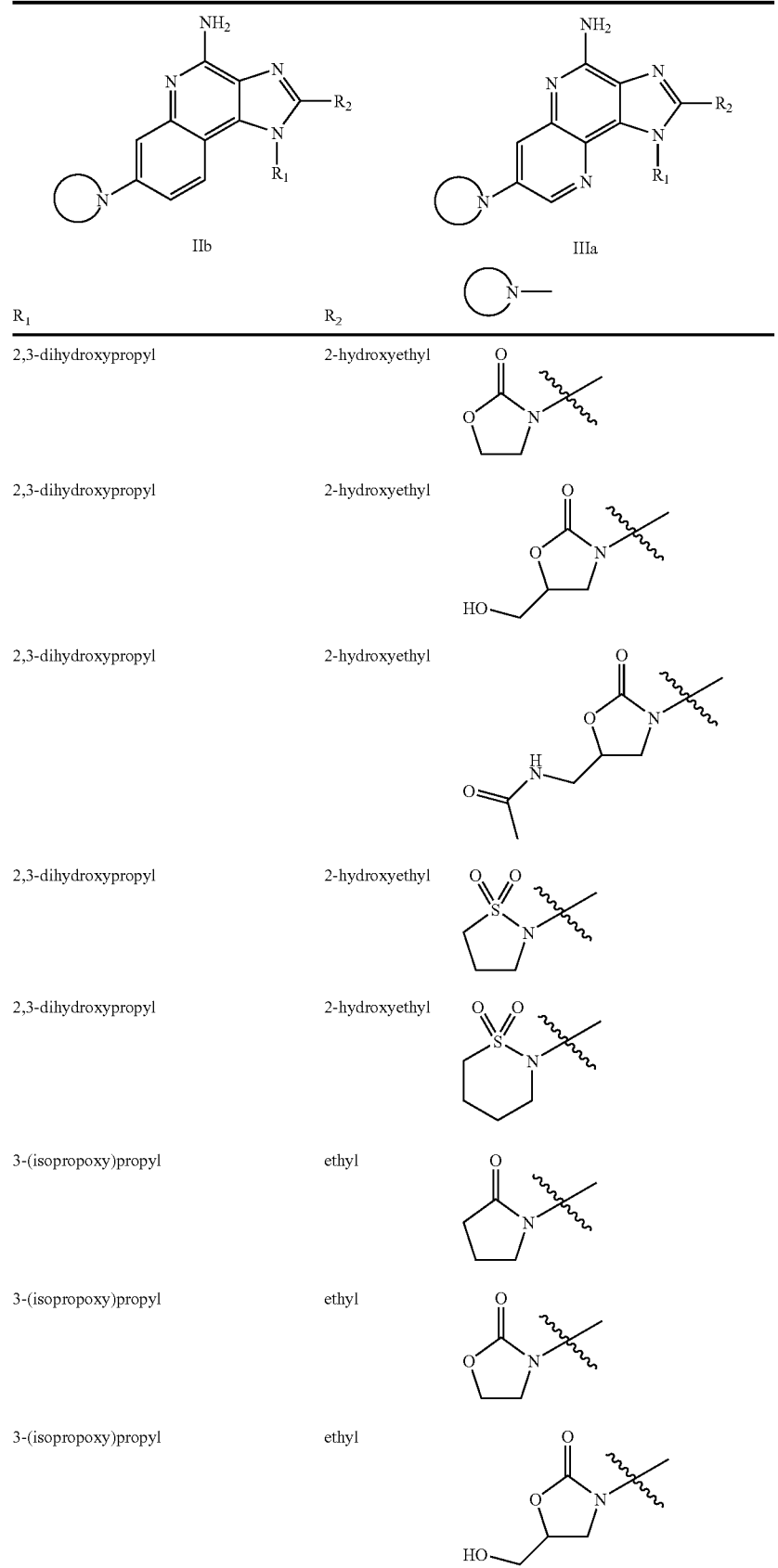

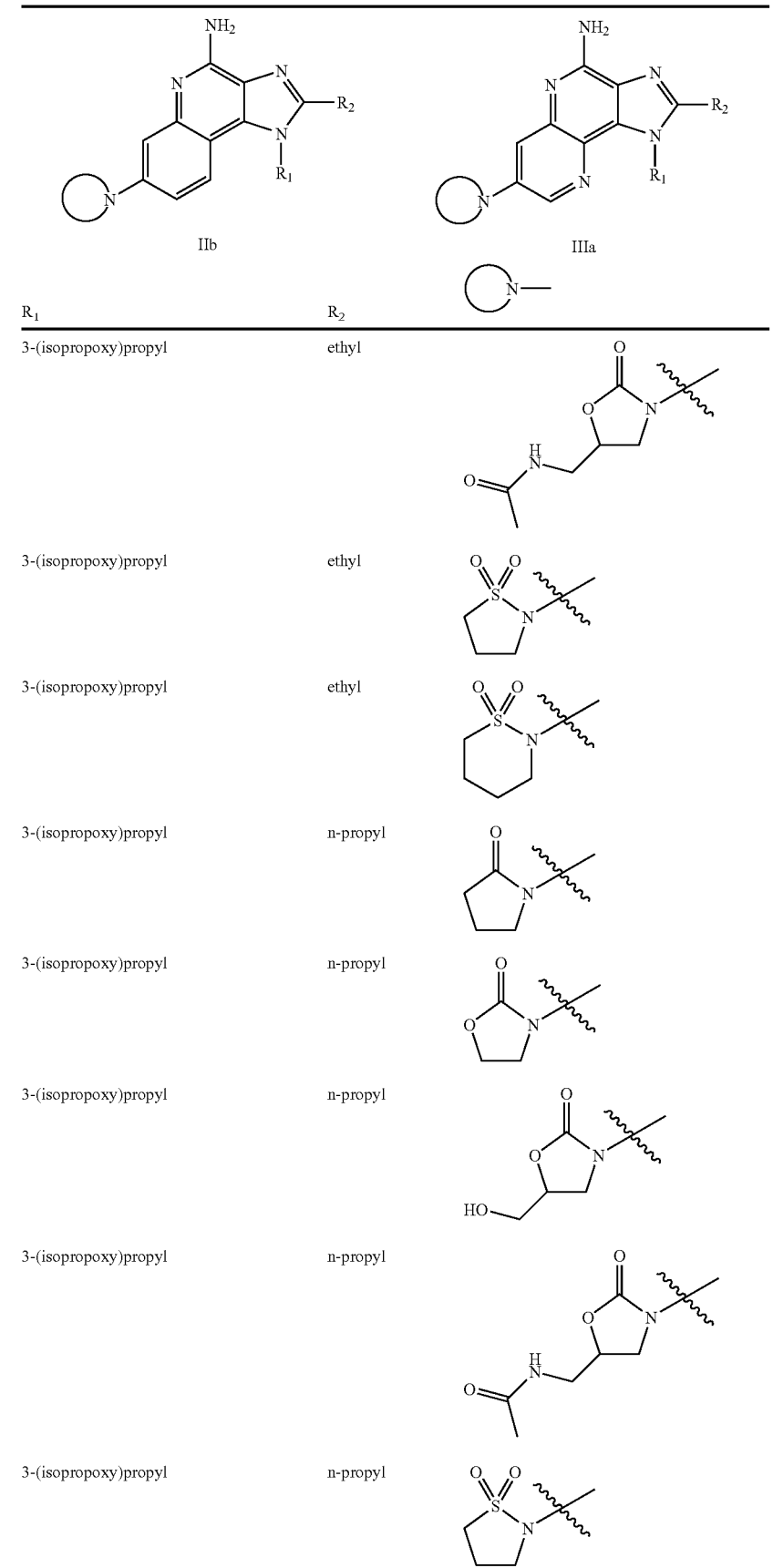

-continued
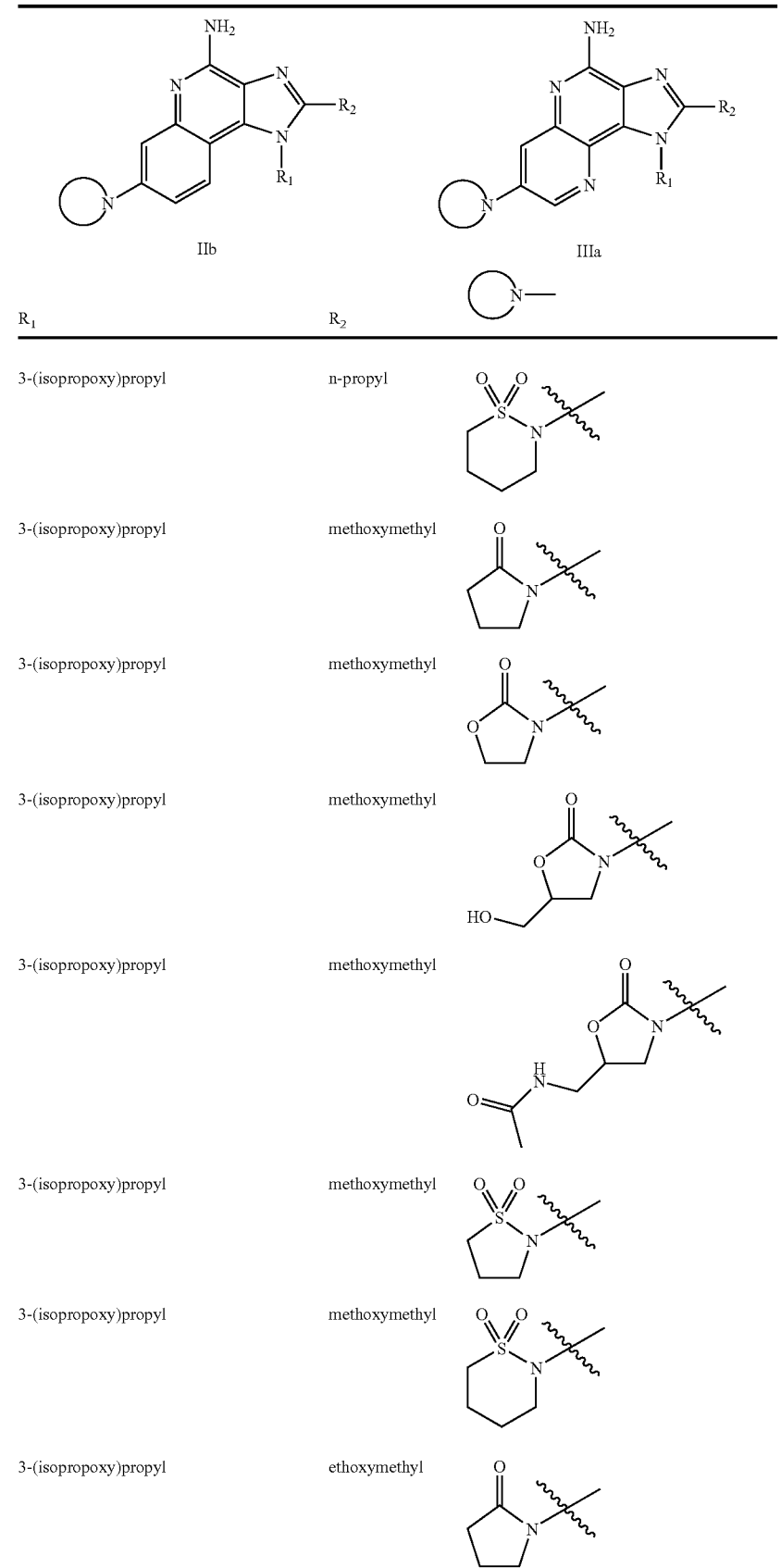

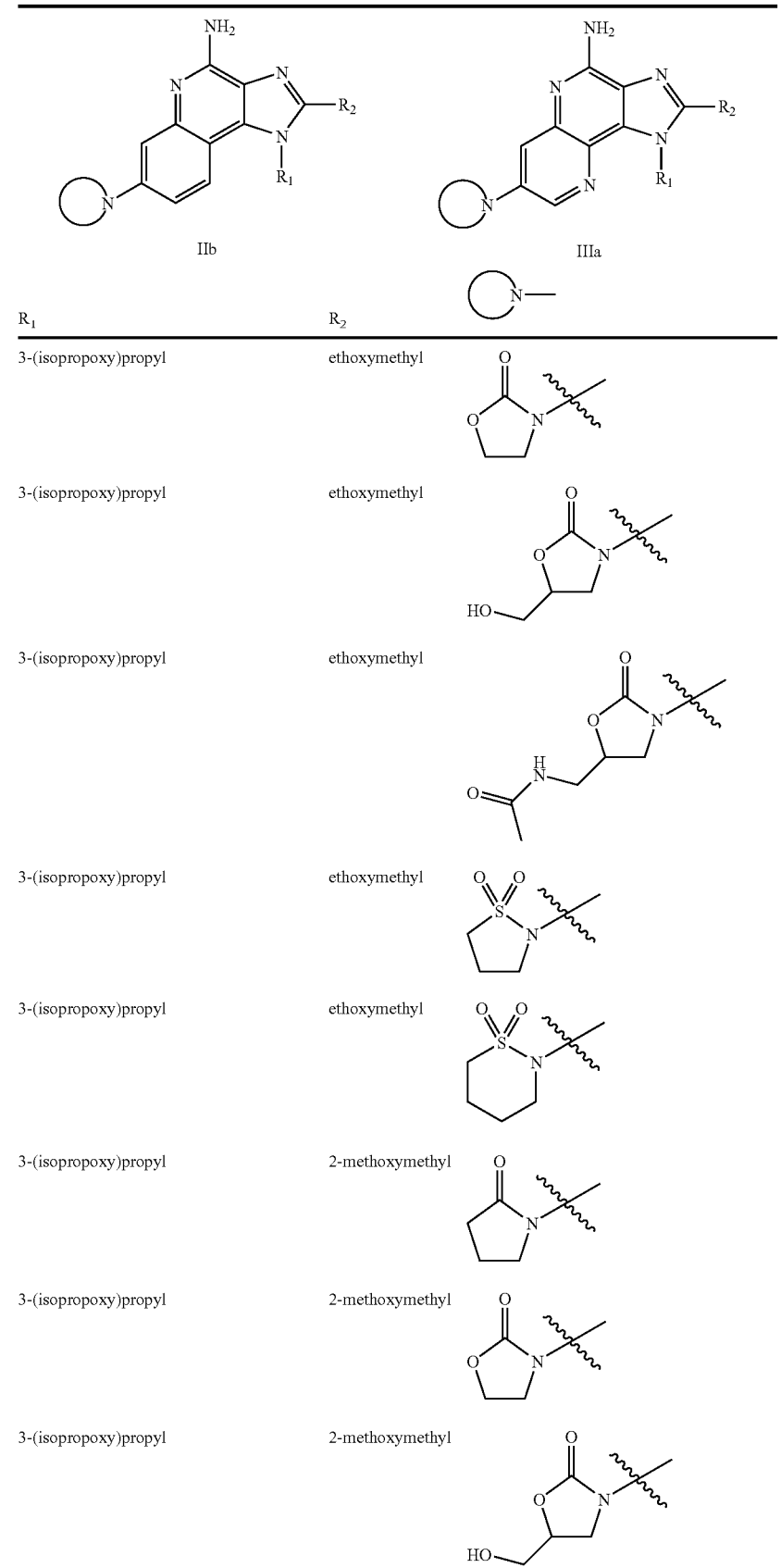

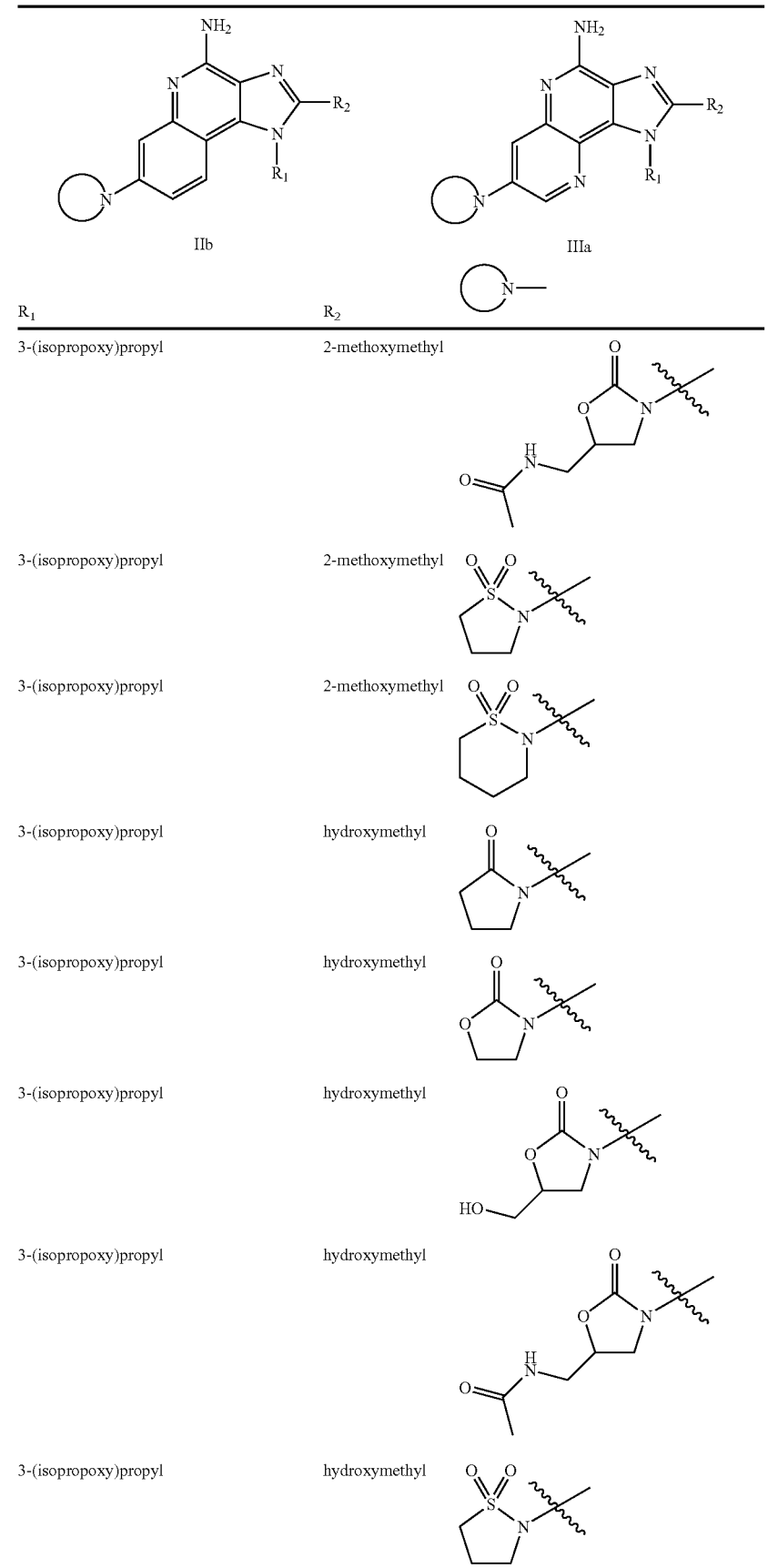

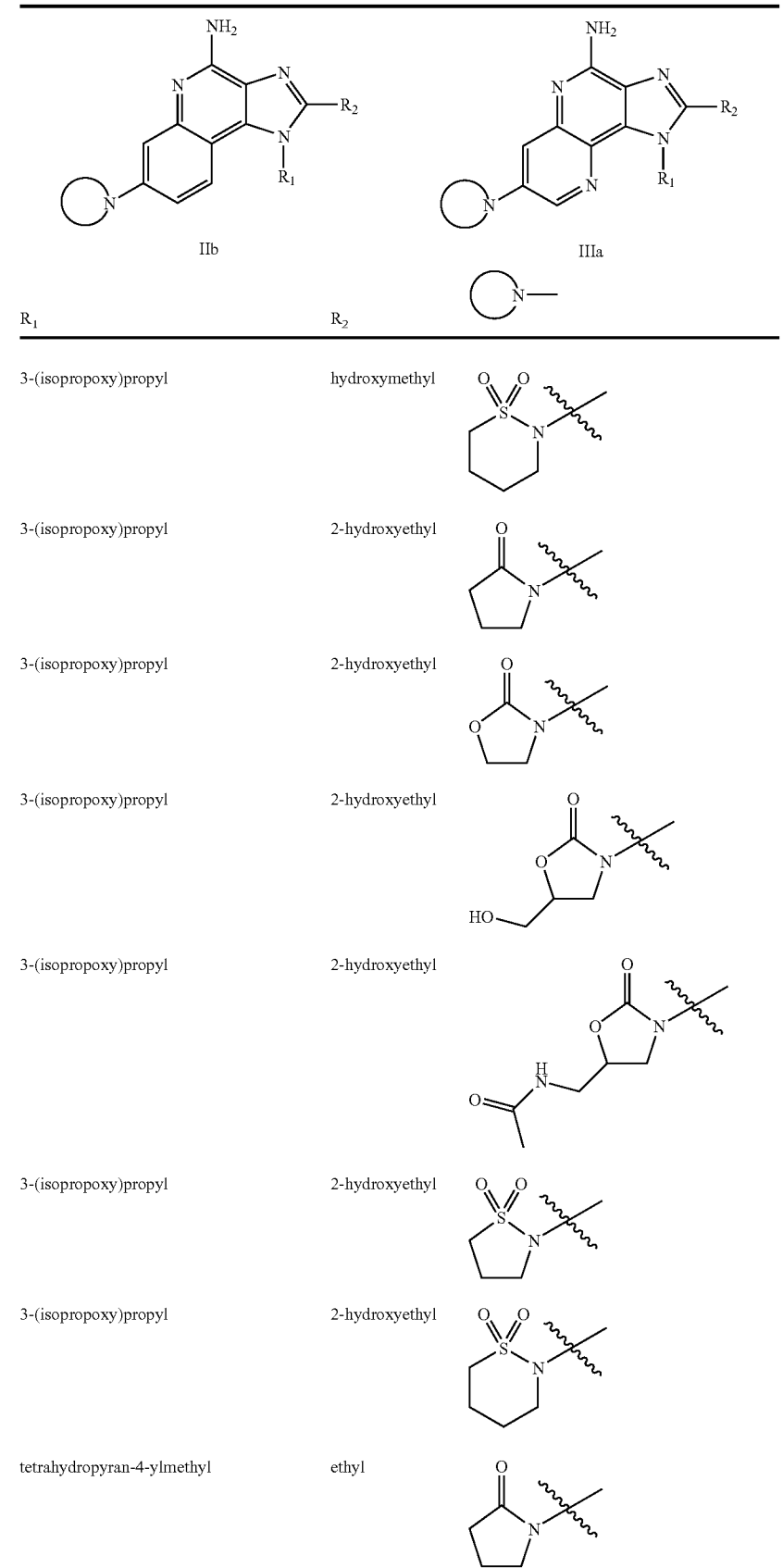

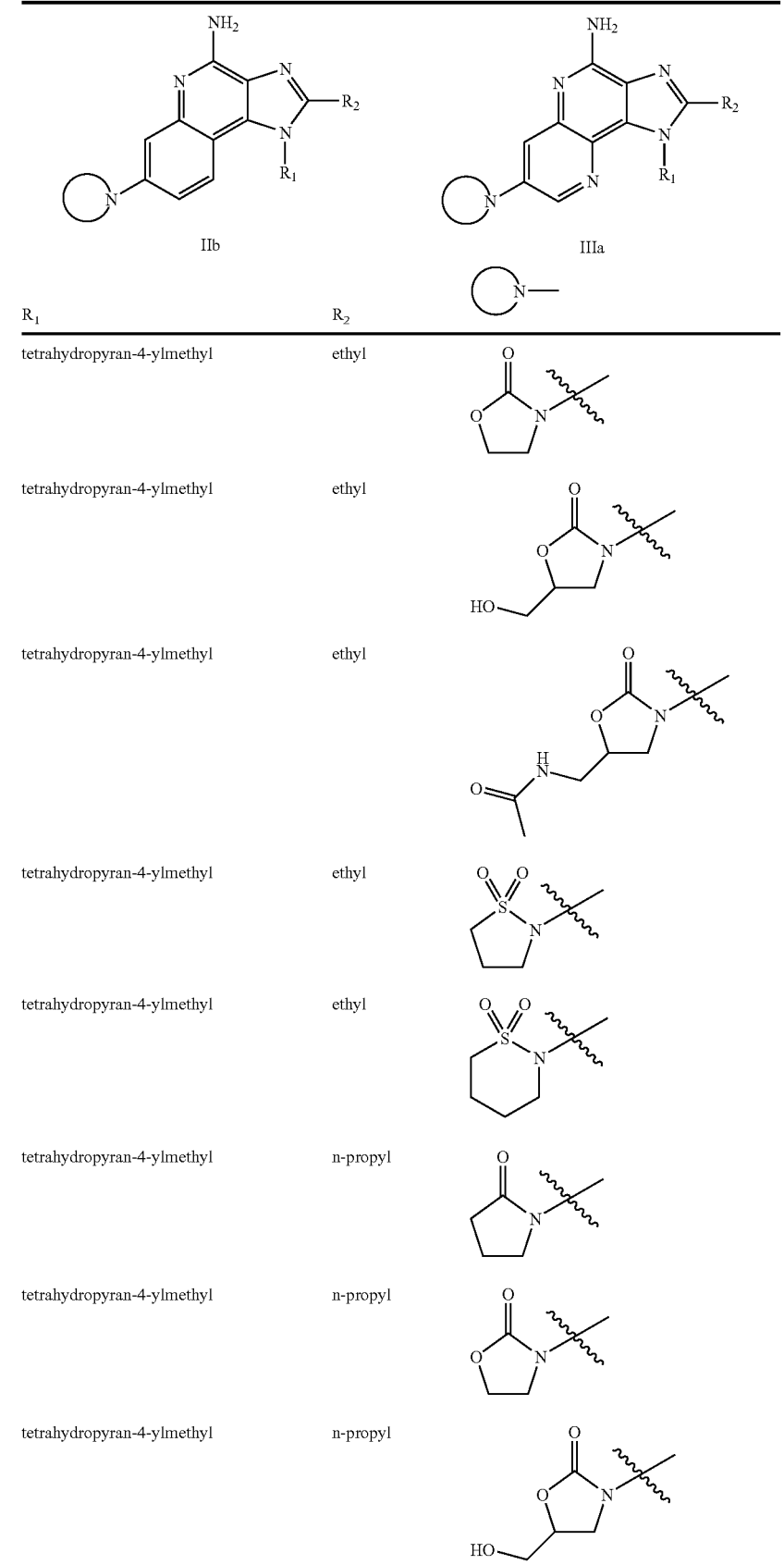

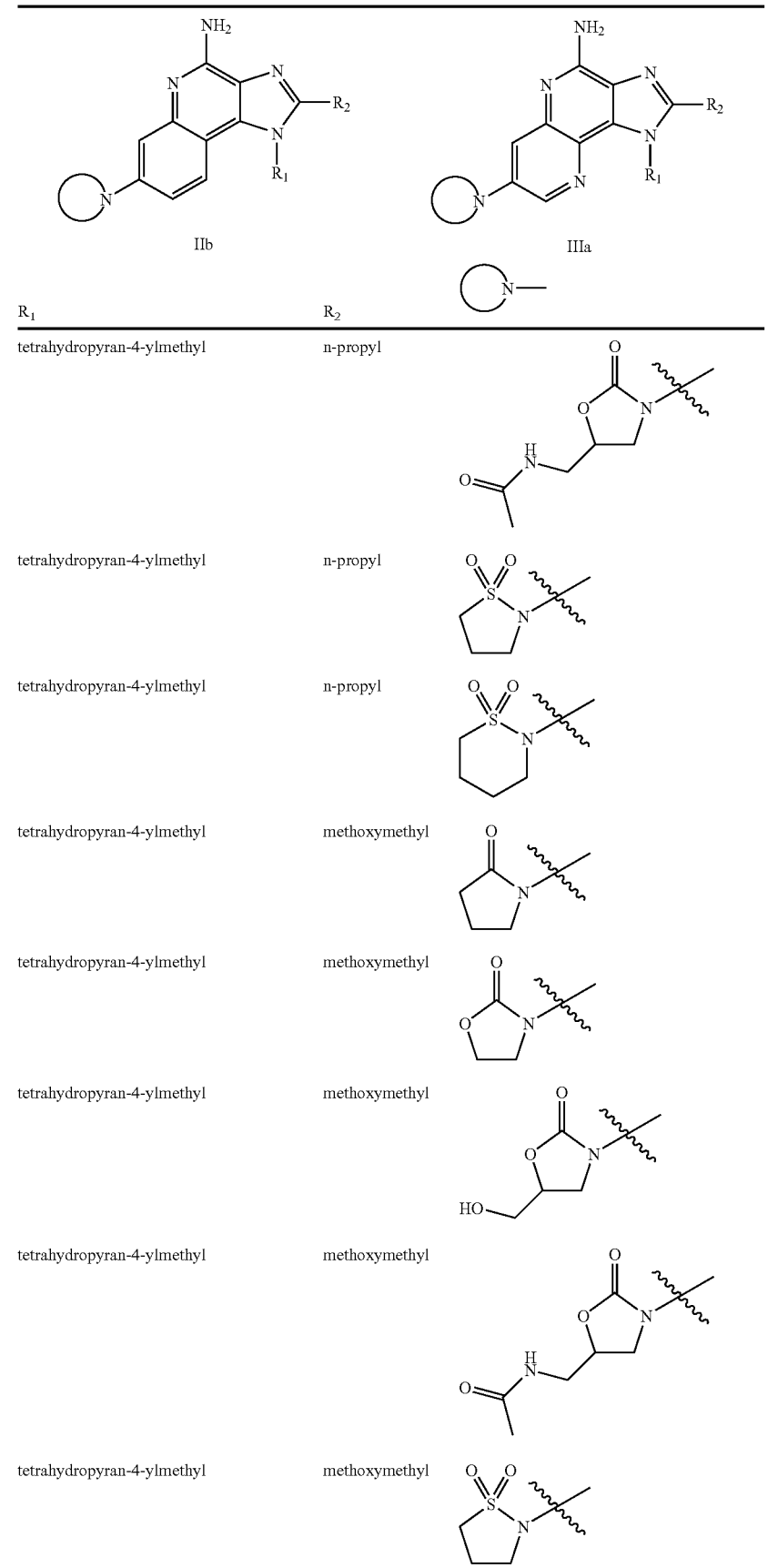

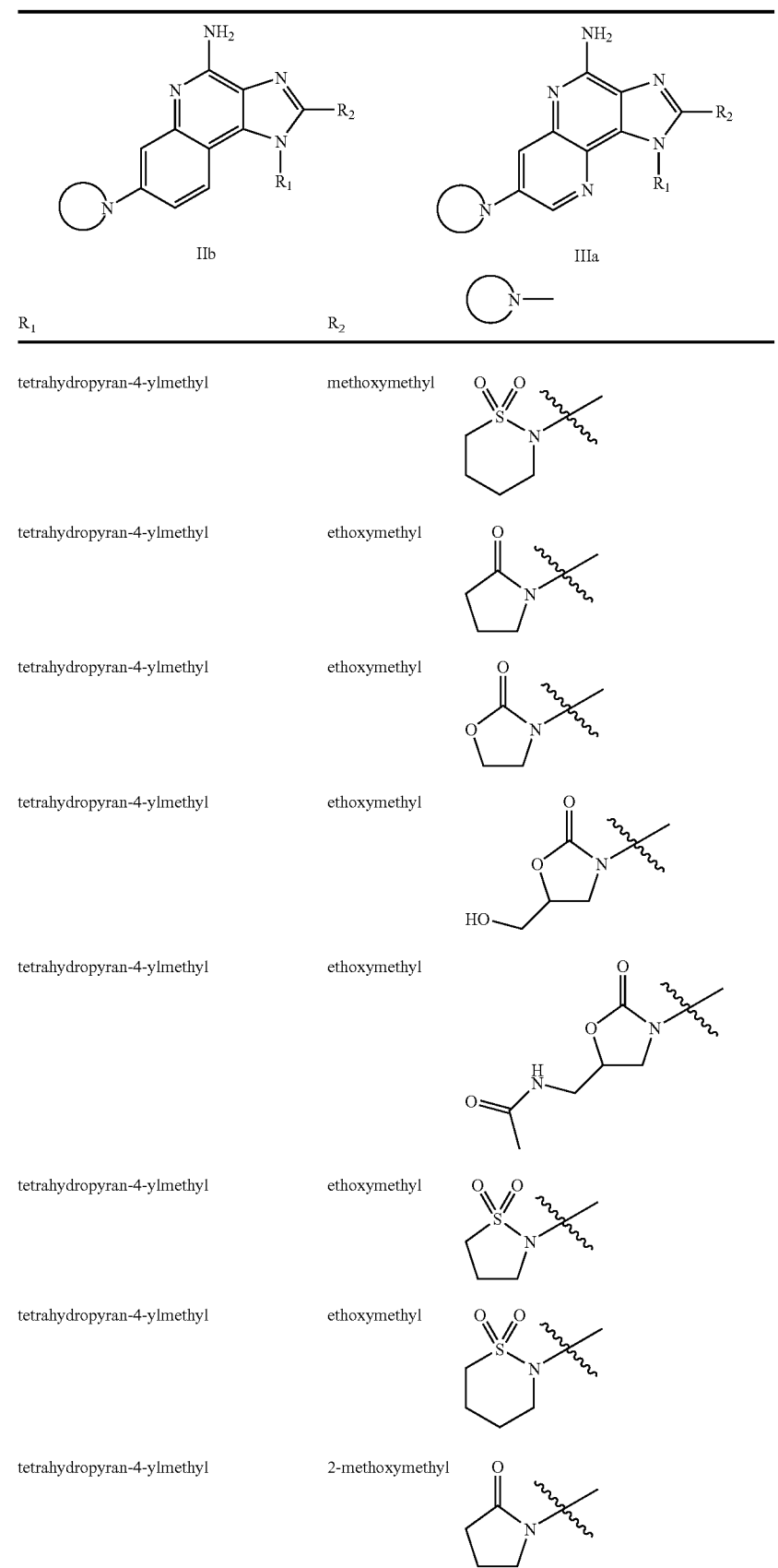

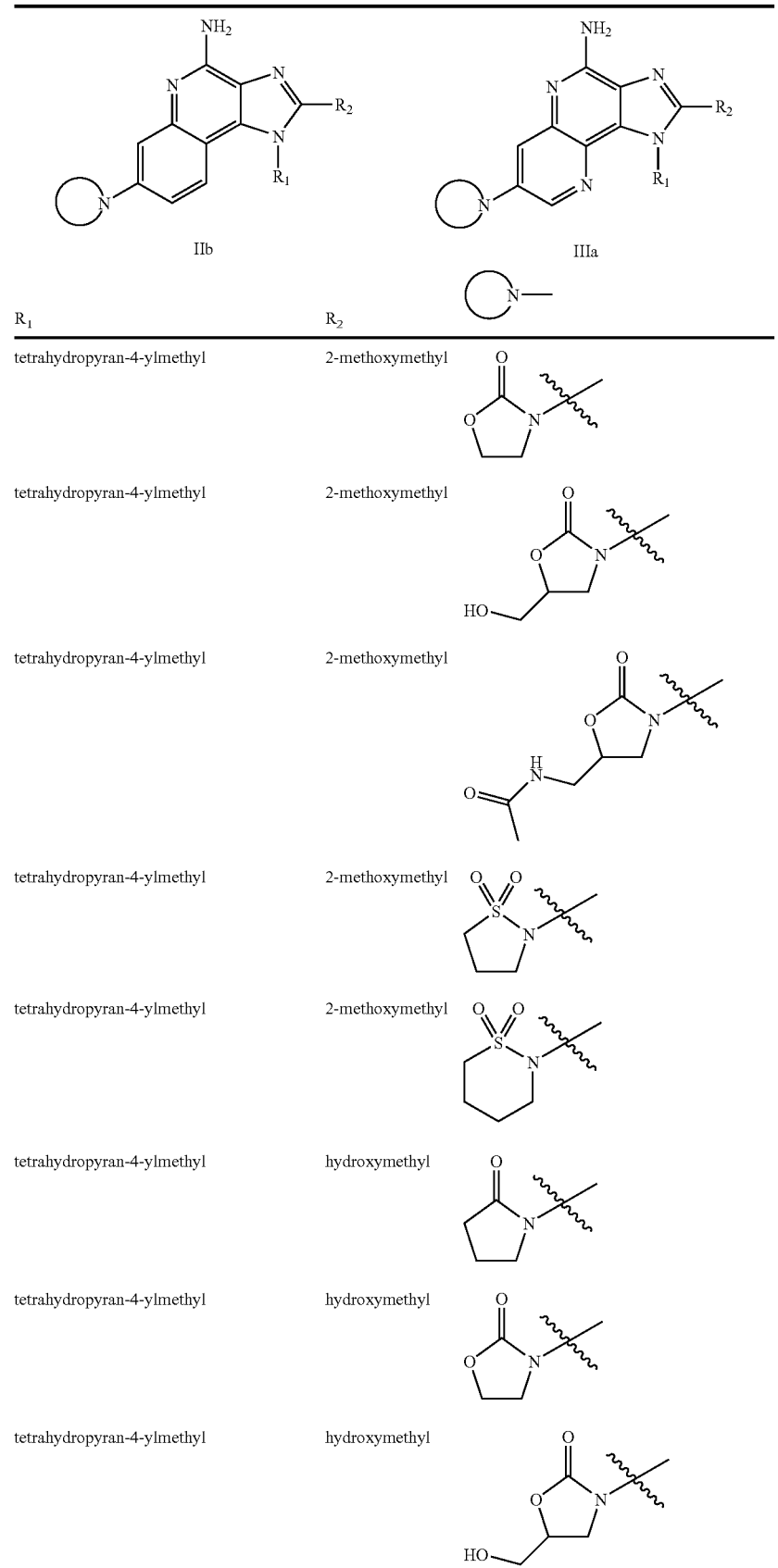

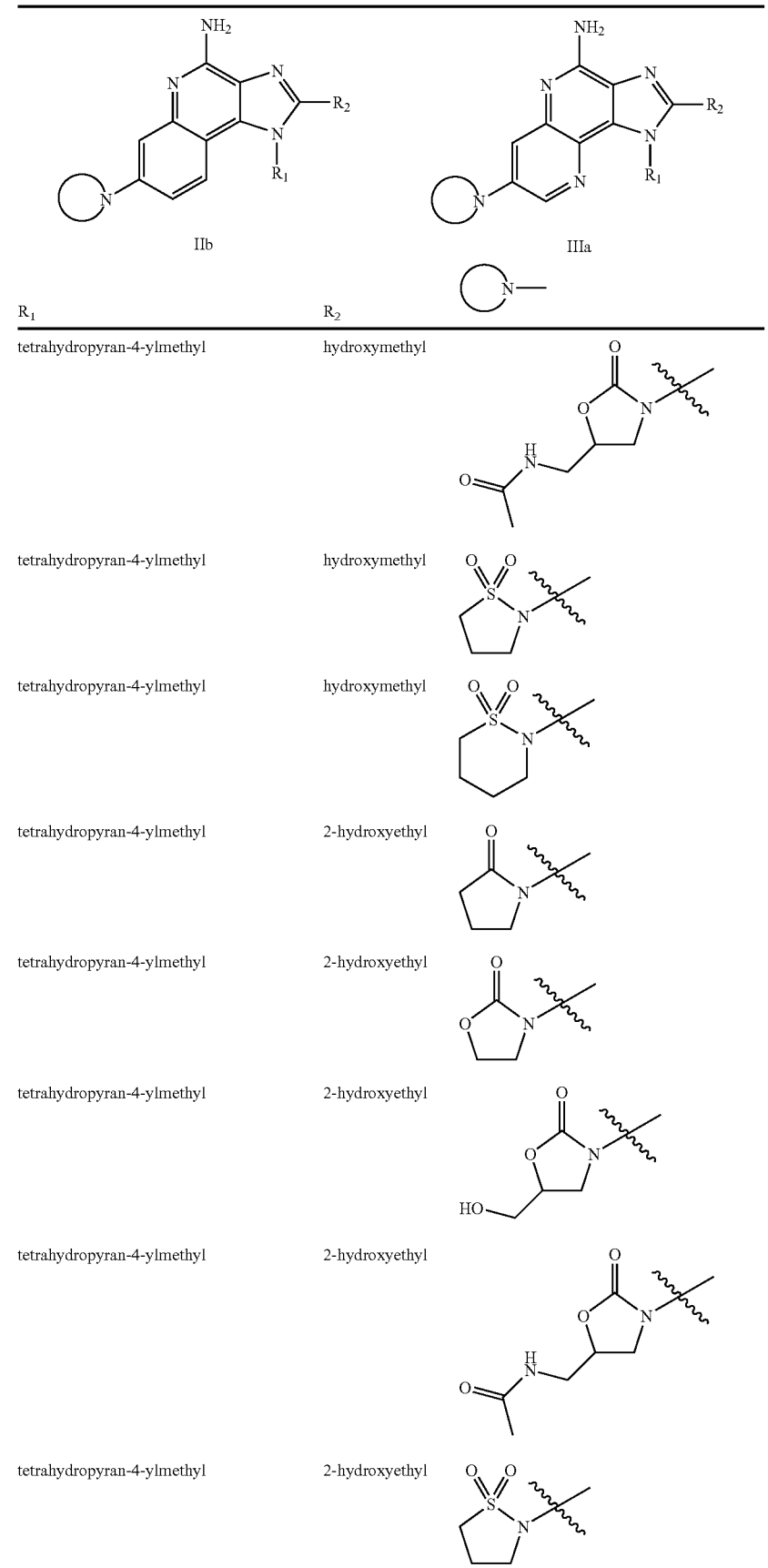

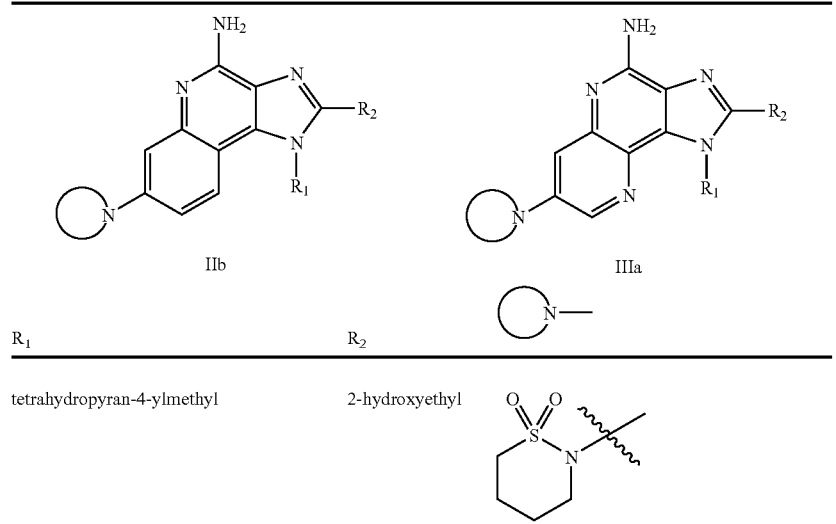

Compounds of the invention have been found to modulate cytokine biosynthesis by inducing the production of interferon α and/or tumor necrosis factor α in human cells when tested using the methods described below.

Cytokine Induction in Human Cells

An in vitro human blood cell system is used to assess cytokine induction. Activity is based on the measurement of interferon (α) and tumor necrosis factor (α) (IFN-α and TNF-α, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4\times10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM. Controls include cell samples with media only, cell samples with DMSO only (no compound), and cell samples with reference compound.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (usually 30-0.014 μM). The final concentration of PBMC suspension is $2\times10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype calorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*" and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

CYTOKINE INDUCTION IN HUMAN CELLS

High Throughput Screen

The CYTOKINE INDUCTION IN HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 μM. Controls include cell samples with media only, cell samples with DMSO only (no compound), and cell samples with a reference compound 2-[4-amino-2-ethoxymethyl-6,7,8,9-tetrahydro-α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 μM) than the final tested concentration range.

Incubation

Compound solution is then added to the wells containing the PBMC suspension bringing the test compound concentrations to the desired range (usually 30-0.014 μM) and the DMSO concentration to 0.4%. The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (SD, Gaithersburg, Md.). The cell-free culture supernatants are removed and transferred to the MSD plates. Fresh samples are typically tested, although they may be maintained at −30 to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-α F (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemoluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α- dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

TNF-α Inhibition in Mouse Cells

Certain compounds of the invention may modulate cytokine biosynthesis by inhibiting production of tumor necrosis factor α (TNF-α) when tested using the method described below.

The mouse macrophage cell line Raw 264.7 is used to assess the ability of compounds to inhibit tumor necrosis factor-α (TNF-α) production upon stimulation by lipopolysaccharide (LPS).

Single Concentration Assay:
Blood Cell Preparation for Culture

Raw cells (ATCC) are harvested by gentle scraping and then counted. The cell suspension is brought to $3 \times 10^5$ cells/mL in RPMI with 10% fetal bovine serum (FBS). Cell suspension (100 μL) is added to 96-well flat bottom sterile tissues culture plates (Becton Dickinson Labware, Lincoln Park, N.J.). The final concentration of cells is $3 \times 10^4$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 5 μM. LPS (Lipopolysaccharide from *Salmonella typhimurium*, Sigma-Aldrich) is diluted with colorless RPMI to the $EC_{70}$ concentration as measured by a dose response assay.

Incubation

A solution of test compound (1 μl) is added to each well. The plates are mixed on a microtiter plate shaker for 1 minute and then placed in an incubator. Twenty minutes later the solution of LPS (1 μL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

Dose Response Assay:
Blood Cell Preparation for Culture

Raw cells (ATCC) are harvested by gentle scraping and then counted. The cell suspension is brought to $4 \times 10^5$ cells/mL in RPMI with 10% FBS. Cell suspension (250 μL) is added to 48-well flat bottom sterile tissues culture plates (Costar, Cambridge, Mass.). The final concentration of cells is $1 \times 10^5$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 0.03, 0.1, 0.3, 1, 3, 5 and 10 μM. LPS (Lipopolysaccharide from *Salmonella typhimurium*, Sigma-Aldrich) is diluted with colorless RPMI to the $EC_{70}$ concentration as measured by dose response assay.

Incubation

A solution of test compound (200 μl) is added to each well. The plates are mixed on a microtiter plate shaker for 1 minute and then placed in an incubator. Twenty minutes later the solution of LPS (200 μL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:
1. A compound of formula (IIa):

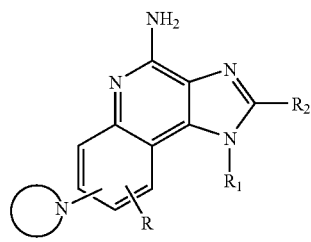

wherein:

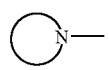

is a heterocyclic ring system selected from the group consisting of:

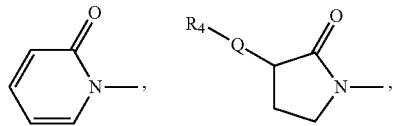

-continued

[structures]

wherein the heterocyclic ring system is unsubstituted or substituted by one or more substituents selected from the group consisting of:
alkoxy,
hydroxy,
nitro,
oxo,
hydroxyalkyl,
alkyl,
phenyl optionally substituted by one or more halogens,
benzyl optionally substituted by one or more halogens,
—N(R$_8$)-Q-R$_4$,
—X—N(R$_8$)-Q-R$_4$,
—X—O-phenyl, wherein phenyl is optionally substituted by one or more substituents selected from the group consisting of alkoxy and halogen,
—X-pyrrolidinyl, —X-piperidinyl, —X-morpholinyl, and —X-piperazinyl, wherein pyrrolidinyl, piperidinyl, morpholinyl, and piperazinyl are unsubstituted or substituted by one or more substituents selected from the group consisting of alkyl, hydroxy, hydroxyalkyl, acetyl, and acetamido;
R$_1$ is selected from the group consisting of alkyl, alkoxyalkylenyl, and hydroxyalkylenyl;
R$_2$ is selected from the group consisting of hydrogen, alkyl, alkoxyalkylenyl, and hydroxyalkylenyl;
X is alkylene,
R$_4$ is alkyl;
Q is selected from the group consisting of a bond and —C(R$_6$)—;
R$_6$ is selected from the group consisting of =O and =S;
R$_8$ is selected from the group consisting of hydrogen and alkyl; and
R is selected from the group consisting of hydrogen, alkyl, alkoxy, trifluoromethyl, chloro, fluoro, and hydroxy; or a pharmaceutically acceptable salt thereof.

2. The compound or salt of claim 1 wherein

[structure]

is attached at the 7 position.

3. The compound or salt of claim 1 wherein R$_1$ is selected from the group consisting of propyl, 2-methylpropyl, 2-hydroxy-2-methylpropyl, 2,3-dihydroxypropyl, and 3-isopropoxypropyl.

4. The compound or salt of claim 1 wherein

[structure]

is selected from the group consisting of:

[structures]

-continued

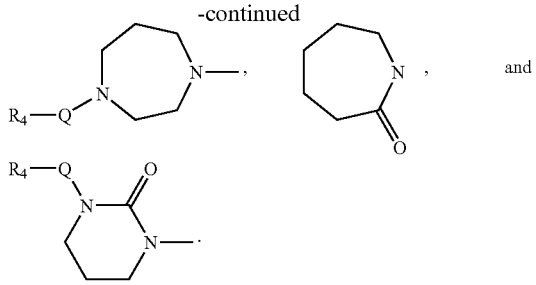

5. A pharmaceutical composition comprising a therapeutically effective amount of a compound or salt of claim 1 and a pharmaceutically acceptable carrier.

6. The compound or salt of claim 1, wherein $R_2$ is selected from the group consisting of hydrogen, $C_{1-4}$alkyl, $C_{1-4}$alkyl-O—$C_{1-4}$alkylenyl, and HO—$C_{1-4}$alkyleneyl.

7. The compound or salt of claim 6, wherein $R_2$ is selected from the group consisting of hydrogen, methyl, ethyl, n-propyl, n-butyl, ethoxymethyl, methoxymethyl, 2-methoxyethyl, hydroxymethyl, and 2-hydroxyethyl.

8. The compound or salt of claim 1, wherein R is hydrogen.

9. The compound or salt of claim 4 wherein

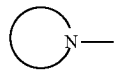

is attached at the 7 position.

10. The compound or salt of claim 4 wherein $R_1$ is selected from the group consisting of propyl, 2-methylpropyl, 2-hydroxy-2-methylpropyl, 2,3-dihydroxypropyl, and 3-isopropoxypropyl.

11. A pharmaceutical composition comprising a therapeutically effective amount of a compound or salt of claim 4 and a pharmaceutically acceptable carrier.

12. The compound or salt of claim 4, wherein $R_2$ is selected from the group consisting of hydrogen, $C_{1-4}$alkyl, $C_{1-4}$alkyl-O—$C_{1-4}$alkylenyl, and HO—$C_{1-4}$alkyleneyl.

13. The compound or salt of claim 12, wherein $R_2$ is selected from the group consisting of hydrogen, methyl, ethyl, n-propyl, n-butyl, ethoxymethyl, methoxymethyl, 2-methoxyethyl, hydroxymethyl, and 2-hydroxyethyl.

14. The compound or salt of claim 4, wherein R is hydrogen.

* * * * *